US009797895B2

(12) United States Patent
Margraf et al.

(10) Patent No.: US 9,797,895 B2
(45) Date of Patent: Oct. 24, 2017

(54) STABILIZING COMPOSITIONS FOR IMMOBILIZED BIOMOLECULES

(75) Inventors: Stefan Margraf, Frankfurt (DE); Anja Breuer, Babenhausen (DE); Martin Scholz, Oberursel (DE); Jens Altrichter, Kavelstorf (DE)

(73) Assignee: Leukocare AG, Munich (DE)

( * ) Notice: Subject to any disclaimer, the term of this patent is extended or adjusted under 35 U.S.C. 154(b) by 1194 days.

(21) Appl. No.: 13/262,542

(22) PCT Filed: Mar. 31, 2010

(86) PCT No.: PCT/EP2010/054391
§ 371 (c)(1),
(2), (4) Date: Dec. 8, 2011

(87) PCT Pub. No.: WO2010/115835
PCT Pub. Date: Oct. 14, 2010

(65) Prior Publication Data
US 2012/0107829 A1 May 3, 2012

(30) Foreign Application Priority Data
Mar. 31, 2009 (EP) .................... 09004734

(51) Int. Cl.
G01N 33/53 (2006.01)
G01N 33/543 (2006.01)

(52) U.S. Cl.
CPC .............. G01N 33/54393 (2013.01)

(58) Field of Classification Search
None
See application file for complete search history.

(56) References Cited

U.S. PATENT DOCUMENTS

| | | | | | |
|---|---|---|---|---|---|
| 4,340,589 A | * | 7/1982 | Uemura | ............... | A61K 47/02 424/94.63 |
| 5,494,807 A | * | 2/1996 | Paoletti | ............... | C07K 14/005 424/199.1 |
| 5,547,794 A | * | 8/1996 | Demizu | ............... | G03G 9/0804 430/108.1 |
| 5,730,933 A | | 3/1998 | Peterson | | |
| 5,780,295 A | * | 7/1998 | Livesey et al. | ............. | 435/307.1 |
| 5,863,542 A | * | 1/1999 | Paoletti | ............... | C07K 14/005 424/188.1 |
| 6,197,291 B1 | * | 3/2001 | Terao | ............... | A61K 38/2053 424/85.2 |
| 6,309,647 B1 | * | 10/2001 | Paoletti | ............... | C07K 14/005 424/186.1 |
| 6,737,405 B2 | * | 5/2004 | Roemisch et al. | ......... | 424/130.1 |
| 6,770,729 B2 | * | 8/2004 | Van Antwerp | ....... | A61K 31/436 424/422 |
| 7,052,875 B1 | * | 5/2006 | Terada | ............... | A61K 48/0008 435/91.1 |
| 8,685,459 B2 | * | 4/2014 | Altrichter | ............... | C12Q 1/22 422/22 |
| 2001/0049361 A1 | * | 12/2001 | Yamashita | ........... | A61K 9/0019 514/54 |
| 2001/0055617 A1 | * | 12/2001 | Mattern | ............. | A61K 38/1816 424/489 |
| 2003/0031584 A1 | * | 2/2003 | Burgess | ................ | A61L 2/0011 422/22 |
| 2003/0118598 A1 | * | 6/2003 | Hunt | .................... | A61K 9/0019 424/184.1 |
| 2003/0138402 A1 | * | 7/2003 | Yamashita | ............. | A61K 9/146 424/85.4 |
| 2003/0138437 A1 | * | 7/2003 | Hunt | ....................... | A61K 8/02 424/184.1 |
| 2003/0138460 A1 | * | 7/2003 | Hunt | ......................... | 424/239.1 |
| 2003/0215575 A1 | * | 11/2003 | Martin et al. | .............. | 427/407.1 |
| 2003/0232198 A1 | * | 12/2003 | Lamberti | ................ | A61L 27/26 428/423.1 |
| 2004/0022792 A1 | * | 2/2004 | Klinke et al. | .............. | 424/178.1 |
| 2004/0033243 A1 | * | 2/2004 | Metcalfe | ............ | A61K 38/2207 424/400 |

(Continued)

FOREIGN PATENT DOCUMENTS

| | | | |
|---|---|---|---|
| CN | 1409758 A | 4/2003 | |
| CN | 1522155 A | 8/2004 | |
| CN | 101910202 A | 12/2010 | |
| EP | 1852443 | * 11/2007 | ............ C07K 17/02 |
| EP | 1852443 A | 11/2007 | |
| EP | 2058335 | * 5/2009 | ............ C07K 17/02 |
| EP | 2058335 A | 5/2009 | |
| JP | S62194459 A | 8/1987 | |
| JP | 2003517153 A | 5/2003 | |
| WO | 2005/083433 A | 9/2005 | |
| WO | 2007128550 A1 | 11/2007 | |

OTHER PUBLICATIONS

Cleland et al., "A specific molar ratio of stabilizer to protein is required for storage stability of a lyophilized monoclonal anibody," J. Pharm. Sci., Am. Pharm. Assoc., Mar. 1, 2001, pp. 310-321, vol. 90, No. 3.
Polifke et al., "Langzeit-Stabilisierung von Assay-Komponenten," Laborwelt, Nov. 1, 2007, pp. 35-39, vol. 8, No. 6.
Vincken et al., "Saponins, classification and occurrence in the plant kingdom," Phytochemistry, Pergamon Press, GB, pp. 275-297, vol. 68, No. 3, 2007.
Durand-Fleith, Odette, International Search Report, PCT/EP2010/054391, dated Oct. 13, 2010, European Patent Office.

*Primary Examiner* — Ann Lam
(74) *Attorney, Agent, or Firm* — Gavrilovich, Dodd & Lindsey LLP

(57) ABSTRACT

The present invention relates to the use of a composition comprising (a) at least three different amino acids, (b) at least two different amino acids and a saponin or (c) at least one dipeptide or tripeptide for stabilizing biomolecules immobilized on a solid carrier. The invention furthermore relates to a method for producing stabilized biomolecules, comprising embedding the biomolecules in the composition according to the invention and a method of producing a solid carrier having biomolecules attached thereto. The invention furthermore relates to a solid carrier producible or produced by the method of the invention and a method of diagnosing a disease using the carrier of the invention.

21 Claims, 30 Drawing Sheets

(56) References Cited

U.S. PATENT DOCUMENTS

| | | | |
|---|---|---|---|
| 2004/0131620 A1* | 7/2004 | Maeda | C07K 16/06 424/159.1 |
| 2005/0136542 A1* | 6/2005 | Todtleben et al. | 436/15 |
| 2005/0169886 A1* | 8/2005 | Brody | A61K 9/0024 424/85.6 |
| 2006/0067950 A1* | 3/2006 | Taylor | 424/239.1 |
| 2006/0110379 A1 | 5/2006 | Green et al. | |
| 2006/0160101 A1* | 7/2006 | Poulet | A61K 39/118 435/6.16 |
| 2007/0141641 A1* | 6/2007 | Fang et al. | 435/7.2 |
| 2008/0031855 A1* | 2/2008 | Okano | A61K 35/768 424/93.6 |
| 2008/0032962 A1* | 2/2008 | Heubes | A61K 9/0019 514/202 |
| 2008/0044928 A1* | 2/2008 | Char et al. | 436/524 |
| 2008/0102524 A1* | 5/2008 | Ueda | A61K 9/19 435/456 |
| 2008/0161400 A1* | 7/2008 | Virsik | A61K 31/05 514/567 |
| 2009/0093047 A1* | 4/2009 | Klapproth et al. | 435/288.7 |
| 2009/0130756 A1* | 5/2009 | Klann | A01N 1/02 435/374 |
| 2009/0226530 A1* | 9/2009 | Lassner | A61K 9/1605 514/1.1 |
| 2009/0269778 A1* | 10/2009 | Margraf | C07K 17/14 435/7.1 |
| 2009/0304628 A1* | 12/2009 | Bello Rivero | A61K 9/19 424/85.5 |
| 2010/0233671 A1* | 9/2010 | Bakaltcheva | A61K 9/0019 435/2 |
| 2010/0291665 A1* | 11/2010 | Margraf | C07K 17/14 435/287.1 |
| 2012/0093803 A1* | 4/2012 | Altrichter et al. | 424/130.1 |
| 2014/0134699 A1* | 5/2014 | Scholz | C12N 7/00 435/174 |

\* cited by examiner

Figure 34
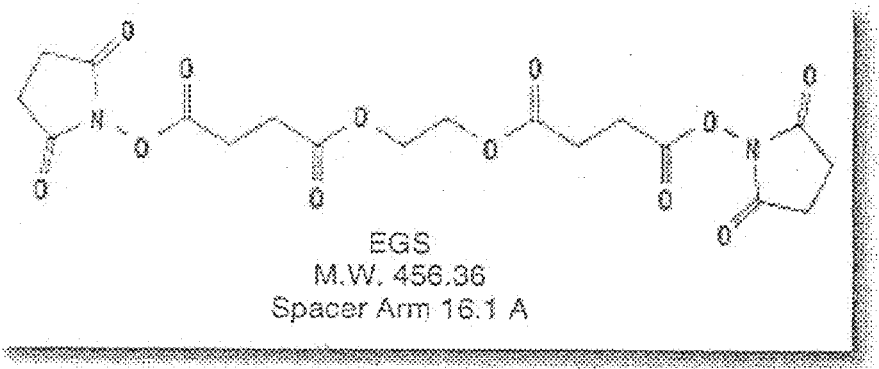
EGS (Ethylene glycol bis[succinimidylsuccinate])
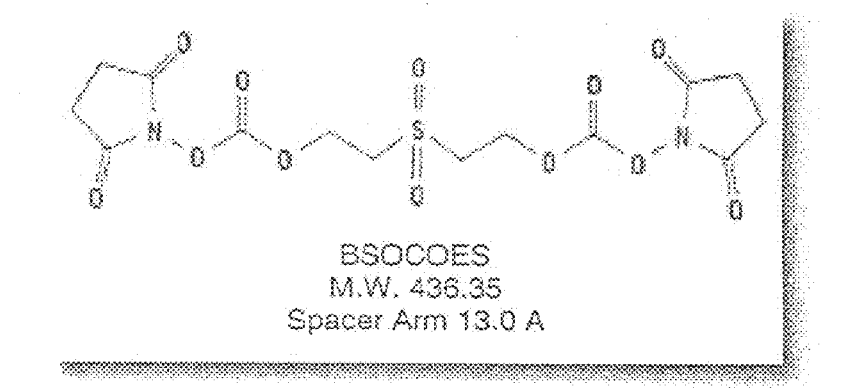
BSOCOES (Bis[2-(succinimidooxycarbonyloxy)ethyl]sulfone)
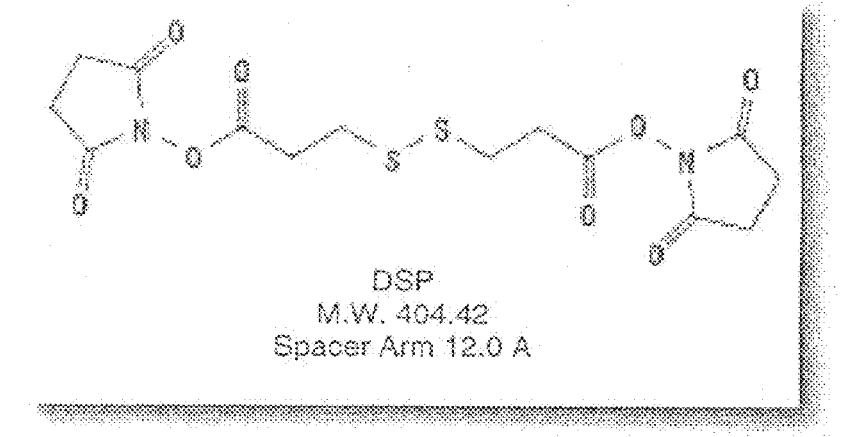
DSP (Dithiobis[succinimidylpropionate])

Figure 34 continued
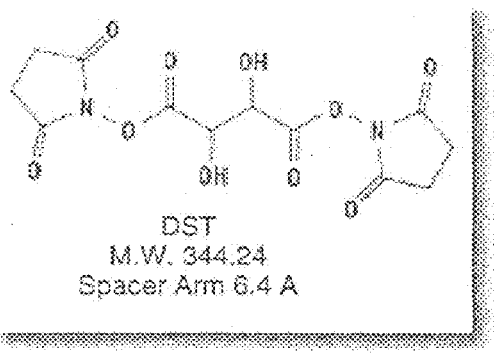
DST (Disuccinimidyl tartarate)
Succinimidyl 2-([4,4'-azipentanamido]ethyl)- 1,3'- dithiopropionate
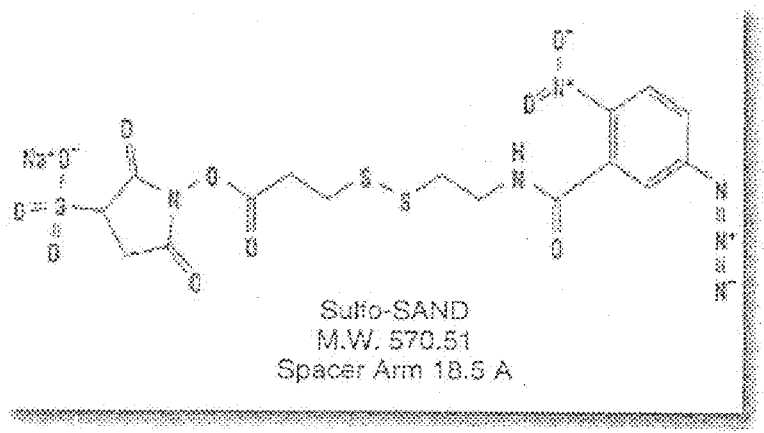
Sulfosuccinimidyl-2-(m-azido-o-nitrobenzamido)-ethyl-1,3'-proprionate

STABILIZING COMPOSITIONS FOR IMMOBILIZED BIOMOLECULES

CROSS REFERENCE TO RELATED APPLICATION

This application is a U.S. National Stage Application filed under 35 U.S.C. §371 based upon International Application No. PCT/EP2010/054391, filed Mar. 31, 2010, which application claims priority to European Application No. 09004734.1, filed Mar. 31, 2009, the disclosures of which are incorporated herein by reference in their entirety.

SUMMARY

The present invention relates to the use of a composition comprising (a) at least three different amino acids, (b) at least two different amino acids and a saponin or (c) at least one dipeptide or tripeptide for stabilizing biomolecules immobilized on a solid carrier. The invention furthermore relates to a method for producing stabilized biomolecules, comprising embedding the biomolecules in the composition according to the invention and a method of producing a solid carrier having biomolecules attached thereto. The invention furthermore relates to a solid carrier producible or produced by the method of the invention and a method of diagnosing a disease using the carrier of the invention.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

BACKGROUND

One major challenge when working with immobilized biomolecules as for example proteins like antibodies in diagnostic and therapeutic applications is to maintain the activity of the biomolecules. However, since the chemical, physical or physiological properties of bio-functional molecules are often significantly altered by variations in the compounds' surrounding environment, this is a difficult task. For example, changes in pH, ionic strength, temperature or storage can result in reversible or irreversible changes in the character of compounds. Especially biomolecules which are subjected to stress like e.g. long-term storage, transport or sterilization procedures have to be stabilized in order to prevent a loss of activity.

For clinical immunodiagnostics, a sufficient stabilization of immobilized biomolecules that are used in diagnostic assays is required for the market entry of products according to the 'EU In Vitro Diagnostics Guideline' (IVDD 98/79/EC).

Implantable medical devices containing immobilized biomolecules, for example, are exposed to a wide variety of biological agents present in the tissues of the body, e.g. acids, bases, ions and the like, depending on the location of the implant in the body. Some of these agents can degrade the bio-molecules of the device leading to damage or even device failure.

Commercially available carriers or devices containing immobilized biomolecule preparations therefore contain stabilizers like sugars (e.g. trehalose) and/or serum-derived proteins (e.g. albumin) in order to protect bio-molecules from degradation (Polifke T. & Rauch P, Laborwelt (2007) Vol. 6, pp 1-4).

Stabilizers that contain serum-derived proteins have the advantage that, in addition to their stabilizing effect, they also function as blocking agents to prevent unspecific binding. However, as albumins and the like are of human or animal origin, they may contain pathogens like for example viruses or prions. Therefore, complex cost and time intensive purification methods have to be applied in order to remove these pathogens.

Another disadvantage of conventional methods for preventing damage to immobilized biomolecules during stress like sterilization or long-term storage is that these methods require that said biomolecules be frozen (U.S. Pat. No. 5,730,933; Cleland J. L. et al., Journal of Pharmaceutical Sciences (2001) Vol. 90, No. 3, pp. 310-321). For example, U.S. Pat. No. 5,730,933 discloses a method for sterilizing antibodies, by which the activity of these antibodies can be retained by freezing them during sterilization. However, freezing can lead to conformational changes of the biomolecules that can affect their biofunctionality and constitutes a further step in the preparation of immobilized biomolecules causing additional costs. Furthermore, the stabilizing composition contains serum proteins like albumin which are of animal origin and therefore bear the risk of contaminating the biomolecules which are incubated therein.

Therefore, a need exists for improved methods and means for stabilizing and protecting immobilized biomolecules that are used in therapy and diagnosis. Thus, the object of the invention is the provision of methods and means for the stabilization of biomolecules that avoid the disadvantages of the state of the art.

DETAILED DESCRIPTION

The present invention relates to the use of a composition comprising at least two different amino acids for stabilizing biomolecules immobilized on a solid carrier.

In particular, the present invention relates to the use of a composition comprising (a) at least three different amino acids, (b) at least two different amino acids and a saponin and/or (c) at least one dipeptide for stabilizing biomolecules on a solid carrier.

A composition used according to the invention can be liquid or solid, depending on the intended use or state. A composition covering and/or embedding the biomolecules attached to a carrier according to the invention as described below is generally solid, whereas in the method of producing a carrier of the invention as also described below, the composition is usually liquid. After removal of the liquid part of the composition and/or drying, the composition covering and/or embedding the biomolecules attached to a carrier according to the invention as described below is again solid. If the composition is liquid, it is preferably aqueous.

Amino acids are defined as organic molecules that have a carboxylic and an amino functional group. They are the essential building blocks of proteins. In connection with the present invention, the term "amino acid" refers to free amino acids which are not bound to each other to form oligo- or polymers such as dipeptides, tripeptides, oligopeptides or proteins.

The amino acids that are contained in the stabilizing composition can be selected from naturally occurring amino acids as well as artificial amino acids or derivatives thereof. Naturally occurring amino acids are e. g. the 20 proteinogenic amino acids glycine, proline, arginine, alanine, asparagine, aspartic acid, glutamic acid (in connection with the present invention, the terms aspartic acid and glutamic acid also include the salts of these amino acids), glutamine, cysteine, phenylalanine, lysine, leucine, isoleucine, histidine, methionine, serine, valine, tyrosine, threonine and tryptophan. Other naturally occurring amino acids are e. g. carnitine, ornithine, hydroxyproline, homocysteine, citrulline, hydroxylysine or beta-alanine.

Derivates of amino acids are e.g. n-acetyl-tryptophan, phosphonoserine, phosphonothreonine, phosphonotyrosine, melanin, argininosuccinic acid and salts thereof or DOPA. Artificial amino acids are amino acids that have a different side chain length and/or side chain structure and/or have the amino group at a site different from the alpha-C-atom.

The term "stabilizing" in the context of the present invention relates to any effect of the composition used according to the present invention resulting in the stabilization of the structure and/or activity of a (immobilized) biomolecule, the elongation of the shelf-life of a biomolecule and/or the protection of a biomolecule against stress. This results in a biological activity of the biomolecule which is retained to a significant degree.

The term "stress" as used in connection with the present invention and as interchangeably used with the term "stress-mediated damage" relates to any environmental influence resulting in a loss of activity of a biomolecule. Exemplary stress factors are heat, drought or radiation, such as radiation induced by sterilization methods described below. Another stress factor is the chemical environment. For example gases such as ethylene oxide used in sterilization can contribute to the loss of activity of a biomolecule.

The term "biological activity" relates to a naturally occurring activity of a biomolecule. Biological activities depend on the specific biomolecule and include binding affinity to other (bio)molecules or catalytic activities. The biological activity of an antibody, for example, requires the specific binding of its antigen. The biological activity of a nucleic acid probe for example requires its ability to specifically hybridize to the nucleic acid target to which it is complementary. In this regard the term "retained to a significant degree" denotes a remaining biological activity of (immobilized) biomolecules having been exposed to stress as compared to (immobilized) biomolecules not exposed to stress of at least 50%, more preferably at least 60%, more preferably at least 70% and most preferably at least 80%.

The term "biomolecule" describes any organic molecule that can be or is produced by a living organism, including, preferably biodegradable, polymeric molecules such as proteins or peptides, carbohydrates and nucleic acids as well as small molecules such as primary metabolites, secondary metabolites, and natural products. The term "biomolecule" not only comprises native molecules as they can be isolated from a living organism but also naturally occurring or artificial molecules which are produced synthetically, semi-synthetically or recombinantly. Artificial molecules are e. g. those derived from naturally occurring molecules with alterations introduced. Biodegradable polymeric molecules other than those belonging to the above-mentioned classes are lignin and polyhydroxylalcanoates (natural polymers) and polyalkylene esters, polylactic acid and its copolymers, polyamide esters, polyvinyl esters, polyvinyl alcohols and polyanhydrides (artificial polymers). Preferred biomolecules exert properties which are relevant for pharmaceutical, diagnostic and/or scientific applications. In other words, the biomolecules applicable in the present invention preferably exert a biological activity which makes them preferably useful and applicable as pharmaceutically active agent(s), diagnostic agent(s) and/or research tool(s).

For the person skilled in the art, it is understood that the term "biomolecules" as applied in the present invention also comprises biomolecules as described above which are comprised in or on structures such as eukaryotic or prokaryotic cells, tissues, viruses as well as fragments thereof (e.g. organelles, membranes or capsids). In this embodiment of the present invention, the biomolecules can be attached to the solid carrier in isolated form or comprised in or on said eukaryotic or prokaryotic cells, tissues, viruses or fragments thereof. Alternatively, the structures comprising the biomolecules, preferably on their surface, may serve as carriers according to the present invention.

The term "polypeptide" interchangeably used with the term "protein" as used herein describes a group of molecules which comprises the group of polypeptides, consisting of more than 30 amino acids. In contrast thereto, a molecule consisting of up to 30 amino acids is designated "peptide". Also in line with the definition the term "peptide" describes fragments of proteins of a length of 30 amino acids or less. Polypeptides or peptides may further form dimers, trimers and higher oligomers, i.e. consisting of more than one polypeptide or peptide molecule. Polypeptide or peptide molecules forming such dimers, trimers etc. may be identical or non-identical. The corresponding higher order structures are, consequently, termed homo- or heterodimers, homo- or heterotrimers etc. The terms "polypeptide", "protein" and "peptide" also refer to naturally modified polypeptides/proteins and peptides, wherein the modification is effected e.g. by glycosylation, acetylation, phosphorylation and the like. Such modifications are well known in the art.

The term "nucleic acid" or "nucleic acid molecule", in accordance with the present invention, includes DNA, such as cDNA or genomic DNA, and RNA such as antisense RNA or siRNA. Further included are nucleic acid mimicking molecules known in the art such as synthetic or semi-synthetic derivatives of DNA or RNA and mixed polymers. Such nucleic acid mimicking molecules or nucleic acid derivatives include phosphorothioate nucleic acid, phosphoramidate nucleic acid, 2'-O-methoxyethyl ribonucleic acid, morpholino nucleic acid, hexitol nucleic acid (HNA), locked nucleic acid (LNA) and peptide nucleic acid (PNA) (see Braasch and Corey, Chem Biol 2001, 8: 1). LNA is an RNA derivative in which the ribose ring is constrained by a methylene linkage between the 2'-oxygen and the 4'-carbon. Nucleic acid molecules may contain additional non-natural or derivative nucleotide bases, as will be readily appreciated by those skilled in the art. Nucleic acid molecules further include ribozymes, aptamers, plasmids and chromosomes. Nucleic acid molecules may be used in accordance with the present invention in isolated form or in complex with other biomolecules such as proteins, e. g. histone proteins or proteins of the ribosome.

The term "carbohydrate" relates to an organic compound that is an aldehyde or ketone with a number of hydroxyl groups added, usually one on each carbon atom that is not part of the aldehyde or ketone functional group. Depending on the length of the molecule, carbohydrates are termed mono-, oligo- or polysaccharides. As soon as carbohydrates are bound to non-carbohydrate molecules, the resulting molecules are termed glycosides. Modified carbohydrates have for example N-acetylester, carboxyl- or sulfate-side chains and may contain glucuronic acid, iduronic acid, galactosamine, glucosamine.

Preferred biomolecules are proteins, peptides, nucleic acids and their derivatives, carbohydrates and their derivatives as well as lipids and fatty acids, polyalcohols and combinations or modifications thereof. Examples of proteins are antibodies or fragments thereof which retain their binding specificity, enzymes, receptors, membrane proteins (optionally without their transmembrane domain), growth factors, albumins, globulins, cytokines, transport proteins, blood coagulation factors and protein hormones. Exemplary carbohydrates are amylopectin, glycogen, starch, alpha- and beta-glucan, dextran, and glycosaminoglycans like hyaluronic acid, heparin, heparan sulfate, chondroitin sulfate and derivatives thereof such as glycosides.

Especially preferred proteins are antibodies or fragments thereof which retain their binding specificity. Antibodies applicable in the present invention can be, for example, polyclonal or monoclonal. The term "antibody" also comprises derivatives of antibodies which still retain their binding specificity. Fragments of antibodies comprise, inter alia, Fab fragments, F(ab')$_2$ or Fv fragments. Techniques for the production of antibodies and fragments thereof are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1998. These antibodies can be used, for example, for immunoprecipitation of molecules of interest or for removing unwanted molecules from body liquids of a patient.

The term "antibody" also includes embodiments such as synthetic, chimeric, single chain and humanized antibodies or derivatives or fragments thereof which still retain their binding specificity. Various procedures are known in the art and may be used for the production of such antibodies and/or fragments. Further, techniques described for the production of single chain antibodies can be adapted to produce single chain antibodies specifically binding to a molecule of interest or fragments thereof. Also, transgenic animals may be used to express humanized antibodies. Most preferably, the antibody is a monoclonal antibody. For the preparation of monoclonal antibodies, any technique that provides antibodies produced by continuous cell line cultures can be used. Examples for such techniques include the hybridoma technique (Kohler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of a biomolecule of interest (Schier, Human Antibodies Hybridomas 7 (1996), 97-105; Malmborg, J. Immunol. Methods 183 (1995), 7-13). It is also envisaged in the context of this invention that the term "antibody" comprises antibody constructs that may be expressed in cells, e.g. antibody constructs which may be transfected and/or transduced via, amongst others, viruses or plasmid vectors. Once the antibody or fragment thereof has been obtained, the antibody itself or the DNA encoding it can be sequenced providing for the information to recombinantly produce the antibody or fragment thereof in small or large scale. Methods of the production of a recombinant antibody are known to the person skilled in the art.

The antibody or derivative or fragment thereof can be further chemically modified as is well known in the art.

The antibody may be of any class of antibody. It is most preferred that the antibody is monoclonal and of the IgG, IgM or IgY class. IgY antibodies represent the analogs of IgG antibodies in chicken.

The term "immobilized" or "immobilizing" as interchangeably used with the term "attached" or "attaching" relates to the fixation of the biomolecules on the carrier. Said immobilization or attachment or fixation may be irreversible or reversible. Fixation may be due to covalent or non-covalent bonds formed between the material of the carrier and the biomolecules. Exemplary non-covalent interactions include those leading to adsorption. The fixation of the biomolecule(s) to the carrier can be performed by any technique known in the state of the art (see for example, Hermanson, G. T., Bioconjugate Technique (2008), $2^{nd}$ edition):

The fixation may for example be effected via a direct binding of the biomolecules to the solid carrier. Alternatively, the fixation may be effected via an indirect binding via a third compound such as spacer and linker molecules, e.g. silanes or proteins such as biotin, avidin or streptavidin, covering the solid carrier. The term "covering" as used throughout the present invention comprises full coverage as well as partial coverage of the solid carrier. In both alternatives, the binding can be a binding via a covalent or a non-covalent bond. A covalent bond can be achieved e.g. by a chemical reaction between the bio-molecules and a carrier material or between the spacer/linker molecule and the biomolecules. Examples for non-covalent binding comprise weak bonds such as van-der-Waal's bonds or other polar bonds. Such non-covalent bonds occur e.g. between polypeptides or peptides and a solid carrier with a polyethylene surface.

In a preferred embodiment, the biomolecules are reversibly attached on said solid carrier.

The term "reversibly attached" defines that the biomolecules, when attached to the carrier, can be released from said carrier with suitable means. Depending on the kind of attachment, e. g. of whether the attachment is covalent or non-covalent, different means of releasing the biomolecules are applicable. Examples are cleavage by proteases in the case of proteins as biomolecules, a pH change or a change in temperature. The biomolecules are attached to the carrier until needed and only then released from the carrier.

The techniques mentioned above are only examples for immobilizing or reversibly attaching biomolecules on solid carriers. It is emphasized that the present invention is not limited to these examples. Instead, any conventional method known in the state of the art can be applied to immobilize or reversibly attach the biomolecule(s) on a solid carrier.

The reversible attachment of the biomolecule is chosen in such a way that the biomolecule can be quickly released from the carrier. In this regard, the term "quickly" means that more than 50% of said biomolecule, such as 60%, 70% or 80%, can be released within 2 hours or less, such as 1 hour, 30 minutes or 20 minutes, in any combination such as 60% in 30 minutes or 20 minutes, 70% in 30 minutes or 20 minutes or 80% in 30 minutes or 20 minutes, preferably more than 85% within 10 minutes or less and most preferably more than 98% within 1 minute. This can be achieved e. g. by applying one of the methods described below. Furthermore, the reversible attachment of the biomolecules is preferably chosen in such a way that the biomolecules are released immediately before the clinical application.

Reversible attachment, like irreversible attachment, can be covalent or non-covalent.

Preferably, the non-covalent bonds are non-covalent bonds with high affinity and specificity. Examples for such non-covalent bonds are those formed by the streptavidin-biotin or the avidin-biotin system. In this example, streptavidin/avidin is coupled covalently to a suitable carrier. The biotinylated biomolecule then is bound non-covalently but with high affinity to the streptavidin/avidin. By adding excess biotin, the binding is competitively suppressed and the biotinylated biomolecule is released.

The biomolecule may be attached via a linker, preferably a cleavable linker. Suitable linkers can be selected, but are not limited to
a) linkers with disulfide-bridges like SDAD (NHS-SS-Diazirine), SulfoSAND, DSP that can easily be cleaved by the addition of reagents with —SH groups like thiols, mercaptanes, cysteine, mecaptoethanol or dithiothreitol.
b) linkers with peptide bonds which can be cleaved with a specific protease, preferably a human enzyme
c) linkers which are cleavable via ultrasound
d) linkers with ester bonds like EGS that can be cleaved by e.g. hydroxylamine
e) linkers with Sulfons like BSOCOES that can be cleaved at higher ph (e.g. pH 11.6)
d) linkers with cis-Diols like DST that can be cleaved by sodium-meta-periodate.

Alternatively, the biomolecules may be reversibly attached by drying as indicated above and as described in detail further below in connection with the methods of the invention. In this embodiment, reversible attachment is achieved in that the biomolecules and the molecules used as a stabilizer (i. e. amino acids, optionally in connection with a saponin and/or optionally in connection with at least one di- and/or tripeptide as described) and the solid carrier stick together after drying. Release of the biomolecules takes place upon addition of a liquid to the above compounds thus dissolving/solubilising the biomolecules and the stabilizing molecules from the carrier.

The term "solid carrier" defines in the context of the invention a carrier of solid material. The material of the carrier may be either of compact or porous structure. As described herein below, it is preferred that the carrier is of a material selected from the group consisting of glass, medical grade stainless steel, metal alloys (e.g. chrome cobalt molybdenum, titan nitride oxide), hydroxyapatite, silicone, polystyrene, poly-L-lactic acid; polyurethane, polyester, polysulfone, polyethylene, polypropylene, polyacryl, polyacrylnitrile, polyamide, PMMA, fleece wadding, open porous foam plastic or glass and reticular plastic or glass and structures derived from marine sponges (porifera).

In the course of the present invention, it was surprisingly found that biomolecules immobilized on a solid carrier can be stabilized by applying a composition comprising (a) at least three different amino acids, (b) at least two different amino acids and a saponin or (c) at least one dipeptide. This composition covers or embeds the biomolecules and shields them from adverse influences. Analogous to the term "covering", the term "embedding" as used throughout the present invention comprises partial or complete embedding of the biomolecules by the composition used according to the invention. As shown in the appended examples, immobilized biomolecules covered by or embedded in the composition used according to the invention show a marked increase in resistance to stress such as ageing or sterilization while essentially retaining their biological activity.

A major advantage of the stabilizing composition of the present invention is that amino acids and not serum-derived proteins like e.g. albumins, are used as stabilizers. Unlike the latter that are derived from humans or animals, the amino acids of the stabilizing composition used according to the present invention can be produced synthetically. Therefore, the risk of contamination by pathogens like viruses or prions is reduced or avoided.

Besides its protective effect on biomolecules, the stabilizing composition also was found to have the additional effect of blocking free binding sites on the solid carrier having biomolecules attached thereto.

Furthermore, as confirmed in the appended examples, the stabilizing composition used according to the invention is universally applicable: it is suitable for the protection of different molecules such as antibodies (e.g. IgM, IgG), enzymes (e.g. DNAse) or nucleic acids.

The method for stabilizing biomolecules of the present invention has the further advantage that, unlike conventional stabilization methods, it does not require the freezing of the biomolecules. Thus, conformational changes that can occur during the freezing process can be avoided. Therefore, the stabilization method of the present invention is especially suitable for instable or labile biomolecules, like e.g. antibodies, especially the complex structure of IgM molecules.

Further surprisingly, it was found that by incubating biomolecules such as antibodies in the stabilizing composition of the present invention, the ability of these biomolecules to exert their biological activity, e. g. in the case of antibodies to bind their antigen, can be retained to at least 65% when being sterilized by irradiation with 25 kGy as compared to untreated controls.

That is, with the stabilizing composition of the present invention, a significant increase of retention of functionality of the embedded biomolecules can be achieved compared to conventional stabilizers as e.g. disclosed in U.S. Pat. No. 5,730,9333 when being irradiated with 25 kGy.

The composition used according to the present invention preferably does not contain proteins or fragments of proteins which are not amino acids, dipeptides and/or tripeptides. Accordingly, in this preferred embodiment of the present invention, the composition does not contain proteins or fragments thereof consisting of more than three amino acids, nor hydrolysed proteins that are of human or animal origin. Such a composition has the advantage that there is no risk of contaminating the bio-molecules embedded therein. It is furthermore a cost effective alternative to known stabilizing compositions.

In a preferred embodiment of the present invention, the stabilizing composition comprises between 2 and 18 different amino acids, more preferably 2 to 10, even more preferably 2 to 8 and most preferably 2 to 5 or 5 to 8 different amino acids. Alternatively, the composition comprises at least 2, at least 3, at least 4, at least 5, at least 6, at least 7 or at least 8 different amino acids or more such as at least 9, at least 10, at least 11, at least 12, at least 13, at least 14, at least 15, at least 16, at least 17, at least 18, at least 19 or at least 20 different amino acids. The number of different amino acids comprised in the composition preferably does not exceed 18.

As apparent from the appended examples, the composition according to the invention when used for stabilizing immobilized biomolecules exerts its advantageous effects already when two or three different amino acids are present. The effect then gradually increases and the maximum effect is reached when five to eight different amino acids are present in the stabilizing composition. Depending on the procedure applied for testing the stabilizing effect, the maximum effect is reached when 5 different amino acids are present (such as for enhanced ageing) or when eight different amino acids are present (such as for sterilization). The advantageous effects do not or do not essentially decrease with the addition of further different amino acids to the stabilizing composition used according to the invention but are preferably retained. Accordingly, also compositions comprising at least 9, at least 10, at least 11 such as at least 12, at least 13, at least 14, at least 15, at least 16, at least 17, at least 18, at least 19 or at least 20 different amino acids can be used for stabilizing immobilized biomolecules.

In a preferred embodiment, the composition comprises at least 4 or at least 5 amino acids.

As apparent from the examples, the composition according to the invention, when comprising at least 4 or at least 5 amino acids has an even more advantageous effect on the stability of biomolecules immobilized on a solid carrier. Depending on the combination of amino acids, the residual biological activity after stress exposure amounts to up to 87%.

In a further preferred embodiment, the composition comprises at least one amino acid of each group of (a) an amino acid with non polar, aliphatic R groups; (b) an amino acid with polar, uncharged R groups; (c) an amino acid with positively charged R groups; (d) an amino acid with negatively charged R groups; and (e) an amino acid with aromatic R groups.

The naturally occurring amino acids can be classified into the above characteristic groups (Nelson D. L. & Cox M. M., 'Lehninger Biochemie' (2005), pp. 122-127) from each of which at least one amino acid is selected for the composition according to the invention. Also other than naturally occurring amino acids such as artificial amino acids can be classified accordingly. Whereas more than one amino acid of each group such as at least two or at least three can be comprised in the composition according to the invention, it is presently preferred that only one amino acid is selected from each group. The skilled person further understands that not the same number of amino acids of each group has to be present in the composition used according to the invention. Rather, any combination of amino acids can be chosen as long as at least one amino acids of each group is present.

In a preferred embodiment, the composition comprises less than 1%, preferably less than 0.5% by dry weight cysteine within the mixture of at least two or at least three amino acids. This also applies to compositions comprising at least 4, at least 5, at least 6, at least 7, at least 8, at least 9 or at least 10 amino acids or even more such as at least 11, at least 12, at least 13, at least 14, at least 15, at least 16, at least 17, at least 18, at least 19 or at least 20 different amino acids.

Due to the SH group comprised in cysteine, compositions comprising cysteine may be subjected to oxidation taking place e. g. at the SH groups and resulting in displeasing odors and/or possible the composition changing color to shades of brown. In order to minimize these undesired effects, in particular when the composition is used in connection with medical devices, the amount of cysteine comprised in the composition should be reduced as described above. However, even if these effects are undesired, they do not affect the suitability of compositions of the invention comprising a higher percentage of cysteines or otherwise exerting brownish colors or a displeasing odor.

In an especially preferred embodiment, the amino acids comprised in the composition are alanine, glutamic acid, lysine, threonine and tryptophan. Whereas in certain embodiments of the present invention, the composition according to the invention comprises more than the above 5 amino acids, in a further preferred embodiment no other amino acids than alanine, glutamic acid, lysine, threonine and tryptophan are comprised in the composition.

In an alternative preferred embodiment, the amino acids comprised in the composition are aspartic acid, arginine, phenylalanine, serine, valine. Similarly, to the above, whereas in certain embodiments of the present invention, the composition according to the invention comprises more than the above 5 amino acids, in a further preferred embodiment no other amino acids than aspartate, arginine, phenylalanine, serine, valine are comprised in the composition.

In another preferred embodiment, the amino acids comprised in the composition are proline, serine, asparagine, aspartic acid, threonine and phenylalanine; or tyrosine, isoleucine, leucine, threonine and valine; or arginine, glycine, histidine, alanine, glutamic acid, lysine and tryptophan. The last combination of amino acids, i. e. arginine, glycine, histidine, alanine, glutamic acid, lysine and tryptophan, has been shown to be especially advantageous with regard to its properties after sterilization, in particular after irradiation. Said combination of amino acids was shown not to exert any displeasing odor or discoloration after irradiation.

Again, whereas in certain embodiments of the present invention, the composition according to the invention comprises more than 5 or 6 or 7 amino acids, in a further preferred embodiment no other amino acids than those of the combinations listed in this preferred embodiment are comprised in the composition.

In another preferred embodiment, the composition further comprises less than 1%, more preferably less than 0.3% Tween, preferably Tween 80.

Tween is a generic term for polysorbates which are a class of emulsifiers and surfactants used in some pharmaceuticals and food preparations. They are often used to solubilize oily ingredients into water-based products. Polysorbates are oily liquids derived from PEG-ylated sorbitan (a derivative of sorbitol) esterified with fatty acids. Examples for polysorbates are polysorbate 20 (Tween 20 or polyoxyethylene (20) sorbitan monolaurate), polysorbate 40 (Tween 40 or polyoxyethylene (20) sorbitan monopalmitate), polysorbate 60 (Tween 60 or polyoxyethylene (20) sorbitan monostearate), and polysorbate 80 (Tween 80 or polyoxyethylene (20) sorbitan monooleate). Tween 80 is most preferred in the compositions used in the present invention.

In the course of the present invention, it has been found that the addition of less than 1 Tween (preferably related to the dry mass of biomolecules and amino acids) avoids foaming during handling of the liquid composition according to the invention.

As indicated above, the present invention also relates to the use of a composition comprising at least one di- and/or tripeptide for stabilizing biomolecules immobilized on a solid carrier. The definitions given above and the preferred embodiment described above, where applicable, mutatis mutandis apply to this embodiment of the present invention. Accordingly, the composition may be comprised of at least two, at least three, at least four, at least five, at least six, at least seven, at least eight, at least nine or at least ten different di- and/or tripeptides. Exemplary dipeptides are glycylglutamine (Gly-Gln, displaying an enhanced stability as compared to glutamine alone), glycyltyrosine (Gly-Tyr), alanylglutamine (Ala-Gln, the latter two displaying an increased solubility in water as compared to tyrosine alone) and glycylglycine. Further naturally occurring dipeptides are Carnosine ((beta-alanyl-L-histidine), Anserine (beta-alanyl-N-methyl histidine), Homoanserine (N-(4-Aminobutyryl)-L-histidine), Kyotorphin (L-tyrosyl-L-arginine), Balenine (or ophidine) (beta-alanyl-N tau-methyl histidine), Glorin (N-propionyl-γ-L-glutamyl-L-ornithine-δ-lac ethyl ester) and Barettin (cyclo-[(6-bromo-8-en-tryptophan)-arginine]). Further artificial dipeptides are Aspartame (N-L-a-aspartyl-L-phenylalanine 1-methyl ester) and pseudoproline. Exemplary tripeptides are Glutathione (γ-glutamyl-cysteinyl-glycine) and its analogues Ophthalmic acid (L-γ-glutamyl-L-α-aminobutyryl-glycine) and Norophthalmic acid (γ-glutamyl-alanyl-glycine). Further tripeptides are Isoleucine-Proline-Proline (IPP), Glypromate (gly-pro-glu), Thyrotropin-releasing hormone (TRH, thyroliberin or protirelin) (L-pyroglutamyl-L-histidinyl-L-prolinamide), Melanostatin (prolyl-leucyl-glycinamide), Leupeptin (N-acetyl-L-leucyl-L-leucyl-L-argininal) and Eisenin (pGlu-Gln-Ala-OH). It is preferred that the at least one tripeptide and more preferred all tripeptides used as a stabilizer, when used in connection with medical applications according to the invention (see below) do not exert any pharmacological properties. The composition according to this embodiment of the invention preferably does not contain proteins or fragments of proteins which are not amino acids, dipeptides or tripeptides. Accordingly, in this preferred embodiment of the present invention, the composition does not contain proteins or fragments thereof consisting of more than three amino acids. Instead, the composition according to this embodiment preferably further comprises at least one amino acid, preferably at least two, more preferably at least three, even more preferably at least four, at least five, at least six, at least seven, at least eight, at least nine, at least ten different amino acids or more such as at least eleven, at least 12, at least 13, at least 14, at least 15, at least 16, at least 17, at least 18, at least 19 or at least 20 different amino acids.

In a preferred embodiment, the composition used in accordance with the invention comprises a saponin.

Saponins are a class of chemical compounds forming secondary metabolites which are found in natural sources, derive from natural sources or can be chemically synthesized. Saponins are found in particular abundance in various plant species. Saponins are amphipathic glycosides grouped phenomenologically by the soap-like foaming they produce when shaken in aqueous solutions, and structurally by their composition of one or more hydrophilic glycoside moieties combined with a lipophilic triterpene derivative. Examples of saponins are glycyrrhicic acid, glycyrrhetinic acid, glucuronic acid, escin, hederacoside and digitonin. It is preferred that the saponin used as a stabilizer, when used in connection with medical applications according to the invention (see below) do not exert any pharmacological properties.

In a more preferred embodiment, a saponin is comprised in a composition comprising any number of different amino acids comprised in the above list of minimum numbers of amino acids, such as in a composition comprising at least 3, at least 4, at least 5, at least 6, at least 7, at least 8, at least 9 or at least 10 different amino acids or even more, such as at least eleven, at least 12, at least 13, at least 14, at least 15, at least 16, at least 17, at least 18, at least 19 or at least 20 different amino acids.

In a more preferred embodiment, the saponin is glycyrrhizic acid (also: glycyrrhicic acid), also known as glycyrrhizin or glycyrrhizinic acid or a derivative thereof.

Derivatives of glycyrrhizic acid are well-known in the art and include those produced by transformation of glycyrrhizic acid on carboxyl and hydroxyl groups, by conjugation of amino acid residues into the carbohydrate part or the introduction of 2-acetamido-β-D-glucopyranosylamine into the glycoside chain of glycyrrhizic acid. Other derivatives are amides of glycyrrhizic acid, conjugates of glycyrrhizic acid with two amino acid residues and a free 30-COOH function and conjugates of at least one residue of amino acid alkyl esters in the carbohydrate part of the glycyrrhizic acid molecule. Examples of specific derivatives can be found e. g. in Kondratenko et al. (Russian Journal of Bioorganic Chemistry, Vol 30(2), (2004), pp. 148-153).

In the course of the present invention, it has surprisingly been found that upon addition of glycyrrhizic acid to the above described composition, biomolecules retain even more of their biological activity than by using compositions comprising only amino acids as stabilizing agents. In this regard, it is particularly remarkable that glycyrrhizic acid alone does not exert any stabilizing or protective effect on immobilized biomolecules.

In another preferred embodiment, the stabilizing composition further comprises a polyalcohol, preferably a sugar or sugar alcohol which is selected from xylose, mannose, glucose, fructose, lactose, maltose, sucrose, trehalose, raffinose, dextran, mannitol, sorbitol or inositol.

In an additional preferred embodiment, the liquid embodiment of the composition is a preferably buffered, preferably aqueous solution but can also be water or a non buffered, preferably aqueous, salt solution. The buffer to be used depends, inter alia, on the biomolecule which is to be covered/embedded. Buffers generally suitable for the contact with biomolecules are e.g. phosphate, citrate, acetate, borate, carbonate, lactate, ammonium, glycine, barbiturate, HEPES, MOPS, MES, TRIS. Exemplary buffers suitable for antibodies are described further below.

In another embodiment, the present invention relates to a method for stabilizing biomolecules or for producing stabilized biomolecules, comprising (a) attaching the biomolecules to a solid carrier and (b) embedding the biomolecules in the composition according to the invention. Possible ways of immobilizing have been described above and can be applied in the present method. Preferably, in step b), the biomolecules are covered or embedded partially or completely in the composition.

The detailed procedure of embedding is described further below in connection with the method of the invention of producing a solid carrier, in particular step (b) thereof, but optionally also steps (c), (d) and/or (e).

The present invention furthermore relates to a method of producing a solid carrier having biomolecules attached thereto, comprising the steps of (a) attaching the biomolecules to the solid carrier; and
(b) incubating the carrier of step (a) in the composition described according to the invention.

The terms "attaching" and "immobilizing" in connection with the biomolecules have been defined and the details of the procedure have been described above. Said definition and description equally apply to the methods of the present invention and other embodiments described below. In particular, the attachment of the biomolecules can be reversible or irreversible as defined above.

The term "incubating" refers to an incubation under conditions that allow the compounds recited in step (a) to attach to the carrier and the biomolecules attached to the solid carrier in step (a) to be embedded in the stabilizing composition recited in step (b). In this embodiment, the composition to be used for incubation with the solid carrier is liquid and preferably an aqueous solution. The composition may have been originally a solid composition. In this embodiment, the originally solid composition is dissolved in a preferably aqueous medium and thus is comprised in a preferably aqueous solution.

Thereby a postcoating layer is formed above and/or around the biomolecules which stabilizes the biomolecules, inter alia, by reducing their accessible surface and by associating with complementary areas of their tertiary structure. Whereas the composition is liquid upon application to the biomolecules, its is later dehydrated resulting in a solid composition embedding or covering the biomolecules. The biomolecules can be embedded partially or completely in the composition in step b). The skilled person understands that incubation conditions need to be adapted to the biomolecules attached to the solid carrier.

Incubation conditions include those where incubations are effected from 20 minutes to 12 hours depending on the step and the temperature. Antibodies, for example, can be incubated for 1 hour at 37° C., which is the maximum temperature where IgM antibodies are stable. IgG antibodies can be incubated to up to 50° C. The temperature range may be from 4° C. to 50° C., preferably 20° C. to 37° C., depending on the step and the incubation time.

In a preferred embodiment, incubation in step (b) is effected for 1 hour at room temperature. It is understood that in order to expedite the procedure or to improve the results, the incubation times and temperatures can be varied according to the substances used in the incubation. The skilled artisan is aware that the term "room temperature" can imply different temperatures depending on the location and the outside temperature. It usually ranges between 17° C. and 23° C.

Preferably, the liquid composition in step (b) is buffered and more preferably of low salt content. A low salt content according to the present invention is defined as a salt concentration of 0.9% (w/w) or less, preferably less than 0.2% (w/w). Generally, but not exclusively, for antibodies such as IgG and IgY antibodies, a more alkaline buffer, e.g. made of 15 mM sodium carbonate and 35 mM sodium hydrogencarbonate in water (pH 9), is useful whereas for the attachment of IgM a more neutral buffer (pH 7.0 to 7.4), e.g. a phosphate buffer like PBS, is favorable.

A solid carrier resulting from step (a), that is a solid carrier onto which biomolecules are attached, is also termed 'coated' carrier in the context of the present invention.

A solid coated carrier resulting from step (b), that is a solid carrier which is incubated with the composition according to the invention covering and/or embedding the attached biomolecules, is also termed 'postcoated' carrier in the context of the present invention.

In a preferred embodiment, the method further comprises a step (c):
(c) removing the composition applied in step (b).

Steps (a), (b) and (c) are carried out in the above described order.

The term "removing" refers to the qualitative or quantitative removal of the liquid composition after step (b). Thus, the composition is removed at least to a degree where the remaining amount of the composition does not significantly change the quality of a solution used in a subsequent step of the method of the invention. Quantitative removal results in drying of the carrier. The removal may be effected e.g. by suction, e.g. by using a conventional pump to which a pipette may be attached, and the like, compression or blowing. Optionally, such steps are combined and may be further combined with air drying. Preferably, the solution is removed in volume to at least 95% such as at least 98% or at least 99%, 99.5% or 99.8%.

Accordingly, in a more preferred embodiment, where quantitative removal is effected, the method of the invention comprises step (c):

(c) subjecting the solid carrier to drying.

Drying can be effected using well-known techniques such as air-drying, spray-drying, lyophilisation and precipitation. Further suitable techniques comprise crystallization and microcrystallization. In the case of beads or nanoparticles as a carrier, drying can be effected by lyophilisation whereas for other carriers other drying techniques are preferred.

In an alternative preferred embodiment of the invention, the method further comprises a step (c) after step (b):
(c) drying the carrier until the residual liquid content is <20% (w/w).

In accordance with this preferred embodiment of the invention the residual liquid content may be calculated in a manner as known for the determination of the water content of wood. In the case of wood, the percentage of water content of wood (x) is determined by the calculation of the ratio between the mass of the water in the sample ($m_w$) and the mass of the water containing wood sample ($m_u$), multiplied with 100. The mass of a water in the sample ($m_w$) can be determined by subtraction of the mass of the sample after its desiccation from the mass of the water containing wood sample ($m_u$). Accordingly, the percentage of water content of wood is calculated by the following formula:

$$X(\%) = \frac{m_w}{m_u} * 100$$

The residual water content of a preparation of carriers can be determined in analogy, wherein $m_w$ is the mass of the water in the sample of carriers and $m_u$ is the mass of the sample of carriers after the complete desiccation of the sample. In case of a spongiform carrier, $m_w$ is determined after squeezing the excess water out of the pores.

In another preferred embodiment of the invention, the method further comprises a step (a') after step (a):
(a') drying the carrier until the residual liquid content of the composition is less than 10%, preferably less than 5%, more preferably less than 2% such as less than 1%, 0.5% or 0.2 of the originally applied composition. Preferred drying methods are described above and include also methods which are used for removing the composition. It is most preferred that drying is effected by air-drying, spray-drying, lyophilisation, precipitation, crystallization or microcrystallization.

The method of the invention may further comprise a step (a") subsequent to step (a) and prior to step (b) and optionally after step (a'):
(a") incubating the carrier in a buffered aqueous solution comprising a blocking agent and removing the aqueous solution.

A blocking agent may be used in the method for the production of a solid carrier in order to prevent unspecific binding of material added in subsequent steps of the method. This blocking may also have a positive effect on the conformation stability of the biomolecules before the incubation of the carrier in the liquid composition according to the invention in step (b).

In this regard, the composition according to the invention can be used as blocking agent. Other blocking agents in line with the present invention comprise but are not limited to human serum and proteins of such sera (e.g. albumin), milk, egg proteins, plant derived proteins (e.g. soya, wheat) including hydrolysates of said proteins (e.g. gelatin, collagen).

In another preferred embodiment, the method of the invention further comprises a step (e) of sterilizing the solid carrier after step (b), (c) or (d). The ability to sterilize the solid coated carrier produced by the method of the invention allows, inter alia, the production of the solid coated carriers under non-sterile or semi-sterile conditions, wherein the so produced carriers may still be used in the method of the invention described below which involves the contact of the solid coated carrier with a body liquid in vivo, ex vivo or in vitro. This represents a further superior feature of the method and the so produced carrier of the invention since, due to that feature, the costs for the production of the solid carrier can be reduced compared to costs for the production of carriers which may not be sterilized. This is because, in the production process, sterile conditions are not required. As it is well known, conventionally prepared carriers are not suitable for sterilization and must be produced under completely sterile conditions. Moreover, a cost contributing feature is that said carriers may be recycled after their use by sterilization. The recycled carriers may subsequently be used in a further treatment of the same or a different patient or in a further or the same method for diagnosing. Preferably, the sterilization or recycling of the carrier is effected by ethylene oxide (EO), beta radiation, gamma radiation, X-ray, heat inactivation, autoclaving or plasma sterilization depending on the carrier material. It is most preferred that the carrier is sterilized by β- or γ-radiation. Suitable in this embodiment is β-radiation with a dose of 25 kgray using an electron accelerator with 10 MeV. To a certain extent sterilization with ethylene oxide can be applied to the carrier of the invention. In general, the method of sterilization has to be chosen in order not to harm the desired activity of the biological material attached to/immobilized on the solid carrier. This can be effected with the biomolecules as defined above, in isolated form, in complex with each other or other biomolecules or present on higher order structures such as cells or fragments of cells. For living cells of any kind, suitable means of sterilization are not known to date. Thus, embodiments where living cells are used as the biological material and the carrier is sterilized are not part of this invention.

After step (b), (c), (d) or (e), the carrier may be stored until needed.

In another embodiment, the present invention relates to a solid carrier producible or produced by the method of the invention.

In a further embodiment, the present invention relates to a solid carrier having biomolecules attached thereto, wherein said biomolecules are partially or completely covered by/embedded in the composition according to the invention. One embodiment of such a solid carrier, also termed "post-coated carrier", comprising embedded biomolecules is exemplified in the cross-section depicted in the scheme of FIG. 1.

In connection with the present invention the terms "partially covered" or partially embedded" preferably denote that at least 20% of the biomolecules are covered or embedded in the composition according to the invention, preferably at least 30%, at least 40%, at least 50%, at least 60%, at least 70%, at least 80%, more preferred at least 90%, at least 95%, at least 98% or at least 99%.

Definitions and explanations given in connection with the composition according to and the methods of the invention and, inter alia, relating to biomolecules, carrier materials attachment and incubation procedures or sterilization mutatis mutandis apply to the solid carrier of the invention. Also, the particular superior features of the solid carrier of the present invention have been described herein above in the context of the characterization of the method of the invention.

According to a preferred embodiment of the solid post-coated carrier of the invention, the biomolecules that are attached to the solid carrier are e.g. proteins, peptides, nucleic acids, carbohydrates, lipids, fatty acids, polyalcohols and combinations or modifications thereof as described above. Proteins are preferably antibodies, more preferably antibodies of the IgG, IgY or IgM class. Other preferred proteins are cytokines, proteinaceous agonists or antagonists other than antibodies such as enzymes, growth factors, albumins or globulins, receptors, hormones, membrane proteins, albumins, globulins, transport proteins or blood coagulation factors.

In another more preferred embodiment, the biomolecules specifically bind to a marker protein indicative for a disease, a pathogen, preferably a non-cellular pathogen, a cell or a toxin. The term "specifically binds", interchangeably used with "specifically interacts with", in accordance with the present invention means that the biomolecule does not or essentially does not cross-react with other structures or epitopes than those of the pathogen or marker protein indicative for a disease. Preferred biomolecules of this embodiment are antibodies as described above. Cross-reactivity of a panel of antibodies under investigation may be tested, for example, by assessing binding of said panel of antibodies under conventional conditions to the structure/epitope of interest as well as to a number of more or less (structurally and/or functionally) closely related structures/epitopes. Only those antibodies that bind to the structure/epitope of interest in its relevant context (e.g. a specific motif in the structure of a protein indicative for a disease) but do not or do not essentially bind to any of the other structures/epitopes are considered specific for the structure/epitope of interest and thus to be antibodies to be used in accordance with this invention. Corresponding methods are described e.g. in Harlow and Lane, 1988 and 1999, loc cit.

Examples for diseases for which marker proteins exist comprise severe hyperlipidemia of various origin, homozygous familial hypercholesterolemia, heterozygous familial hypercholesterolemia, defective Apo B-100, isolated Lipoprotein (a) elevation, systemic lupus erythematosus (SLE), Sjögren's syndrome, mixed connective tissue disease, dilated cardiomyopathy (DCM), diseases associated with inhibitors to coagulation factors, idiopathic thrombocytopenic purpura (ITP), thrombotic thrombocytopenic purpura (TTP), autoimmune hemolytic anemia, hyperviscosity syndrome in hypergammaglobulinemia, myasthenia gravis, Guillain-Barré syndrome, chronic inflammatory demyelinating polyneuropathy (CIDP), dysproteinemic polyneuropathies, bone marrow transplantation, endocrine orbitopathy, diabetes mellitus type I (IDDM), Goodpasture's syndrome, nephropathies due to immunoglobulin or immune complex deposits, cryoglobulinemia, pemphigus, atopic dermatitis, graft-versus-host (GvH) diseases, host-versus-graft (HvG) diseases, and various forms of vasculitis.

Well-known marker proteins for specific diseases are e. g. pro-calcitonin, cytokines such as TNFα or IL6, and c-reactive protein.

The pathogens to which the biomolecules may bind include those causing infectious diseases, such as bacteria or fungi. Non-cellular pathogens causing infectious diseases include viruses and prions.

Examples for such pathogens are HIV, HBV, HCV, Herpesviruses such as e.g. the Herpes simplex, the Cytomegalo- and the Varicella zoster viruses, gram-positive bacteria e.g.

Streptococci, Staphylococci, gram-negative bacteria e.g. *E. coli, Pseudomonas aeruginosa.*

Also toxins may be indicative of a disease or a certain state of the body. A toxin is a poisonous substance, preferably produced by living cells or organisms. Toxins can be e.g. small molecules, peptides, or proteins that are capable of causing a disease on contact with or absorption by body tissues interacting with biological macromolecules such as enzymes or cellular receptors. Toxins vary greatly in their severity, ranging from usually minor and acute (as in a bee sting) to almost immediately deadly (as in botulinum toxin).

In another preferred embodiment of the present invention, the solid post-coated carrier is sterilized as described above for the use and the method of the invention, e.g. by beta or gamma irradiation. Suitable is e.g. beta-irradiation with a dose of 25 kGy using an electron accelerator with 10 meV.

The solid carriers according to the present invention can be used in therapy and diagnosis.

A further aspect of the invention relates to the use of the composition according to the invention for stabilizing solid carriers having biomolecules attached thereto for long-term storage and/or sterilization.

A major challenge in the long-term storage and sterilization of biomolecules is to avoid irreversible changes to biomolecules having a desired biological activity. These changes can result in molecular modifications of biomolecules that occur when the latter are subjected to stress, further resulting in a loss of the desired biological activity of said biomolecules, in their reduced stability upon storage or in new immunological/antigenic properties which might put the recipients of such products at risk of allergic reactions upon administration or application. This is especially important for proteins which are of complex structure and/or quite labile, like e.g. many therapeutic proteins and monoclonal antibodies.

Researchers have attempted to avoid irreversible changes that can occur to active compounds during sterilization by using ethylene oxide. However, ethylene oxide often reacts with proteins. In addition, because of the known tissue toxicity and the carcinogenic potential of the by-products of ethylene oxide, the Food and Drug Administration has set maximum residue limits for ethylene oxide and its major reaction products ethylene glycol and ethylene chlorohydrin. One advantage of the present invention is that biomolecules are protected by the composition according to the invention so that sterilization can also be effected using ethylene oxide.

Unlike ethylene oxide, radiation sterilization has the advantages of high penetration ability, relatively low chemical reactivity, and instantaneous effects without the need to control temperature, pressure, vacuum or humidity. Radiation sterilization is widely used in industry for a variety of products and both dosage levels and its biological effects are well known. It is generally agreed that electron-beam and gamma sterilization are equally effective in killing microbial organisms.

While sufficient to effectively kill microorganisms, the radiation generally alters the structure of biomolecules like proteins, DNA, RNA etc. as to render them biologically inactive, if they are not protected or stabilized. Therefore, there has been a significant need for a simple way to effectively and safely sterilize biologically active compounds without deleteriously affecting their chemical, physical or physiological properties. This has been achieved in accordance with the present invention.

The introduction of new or modified products to the medical marketplace requires the assurance that they can be stored for an extended period (from one to five years) without any decrease in performance that may affect safety and efficacy when the products are used. Because full-period, ambient-aged samples usually do not exist for such products, it is generally necessary to conduct 'accelerated-aging' tests to provide experimental data in support of performance and shelf-life claims for these products until full-period samples become available.

The primary reason for using accelerated-aging techniques in the qualification testing of a medical device is to bring the product to market at the earliest possible time. The goal is to benefit both the patient—for example, through early availability of a life-enhancing device—and the company—by generating additional sales and market shares—without exposing either to any undue risk.

Accelerated aging can be defined as a procedure that seeks to determine the response of a device or material under normal-usage conditions over a relatively long time, by subjecting the product for a much shorter time to stresses that are more severe or more frequently applied than normal environmental or operational stress. A significant enhancement in test plan efficiency can be achieved using excessive environmental stress such as heat, oxygen, chemicals, or radiation.

A simplified approach for accelerated aging is based on testing at a single accelerated temperature and then employing the rule stating that the rate of a chemical reaction will increase by factor $Q_{10}$ for every 10° C. increase in temperature. The typical relationship selected for commonly used medical polymers is $Q_{10}=2$; that is, a doubling of the reaction rate for each 10° C. increase in the temperature above use or storage temperature.

In order to achieve a sufficient shelf life for biomolecules that are used for diagnosis or therapy, these biomolecules have to be frozen in order to prevent their denaturation (Cleland et al., (2001), Journal of Pharmaceutical Sciences Vol. 90, pp. 310-321). Furthermore, the biomolecules of interest have to be incubated in stabilizing solutions containing so-called lyoprotectants such as sugars (e.g. sucrose, trehalose, mannitol) or salts. However, due to the risk that biomolecules are denatured by freezing, a need exists for storage methods at 4° C. or at room temperature, especially for unstable biomolecules like e.g. IgM antibodies.

Surprisingly it was found that by incubating biomolecules, e.g. antibodies, immobilized on a solid carrier in the stabilizing composition according to the present invention, these biomolecules can be stored up to 7 days at 45° C. without significant loss of their biological activity. According to the rule described earlier, this 'accelerated aging' equals to a storage of 16 weeks at 5° C. Furthermore, the biomolecules can be sterilized without significant loss of their biological activity (see appended examples).

In another embodiment, the present invention relates to medical and diagnostic products and devices comprising the carrier of the invention.

In a further alternative embodiment, the present invention provides the use of a solid carrier of the invention for the preparation of medical or diagnostic products and/or devices. Such devices being a combination of the biological component comprising the biomolecules stabilized according to the invention and a non-biological part are also termed biological-device combination product.

Solid carriers having biomolecules attached thereto that are embedded in/covered by the stabilizing composition according to the present invention can be used in a variety of diagnostic and medical/therapeutic applications. Therapeutic applications or devices include medical implants, catheters, stents, tubings, alone or in combination with other components, matrices capable of eluting the attached biomolecules upon wetting with a liquid such as a body liquid, e. g. wound dressings, or medical devices used in extracorporeal circulation. Diagnostic applications comprise for example immunoassays like ELISA (enzyme linked immunosorbent assays), protein chips, multi-analyte assays, western blots, dot blots, immunohistochemistry, receptor-ligand assays and immuno-PCR.

The therapy approaches may comprise in vivo as well as ex vivo applications of the carrier of the invention in the context of a medical device. Accordingly, a device comprising the solid post-coated carrier can be implanted into a patient for an in vivo application. For an ex vivo application a device comprising the solid coated carrier can be connected with the circulation of a body liquid to be treated. Blood derived from an artery or a vein of a patient may be e.g. led through such device and subsequently piped back into the patient (connection with the blood stream). Alternatively, samples of a body fluid may be incubated with the carrier in vitro. In a subsequent step of the latter treatment the body fluid can be reintroduced into the body of a patient.

One embodiment of the medical device is suitable to enable a contacting, filtering or cleaning of body fluids like e.g. blood, lymph or liquor cerebrospinalis of a patient e.g. by connecting the device with the circulation of the body fluid of a patient and thereby treating a patient as described herein above.

Moreover, the device may be suitable for the qualitative or quantitative detection of compounds as well as for trapping certain cells or cell populations, e.g. stem cells, fetal cells or tumor cells, in a sample of a body fluid of a patient as also described in part herein below. Stem cells comprise pluripotent, multipotent or totipotent stem cells. In general, different cell lines, cell species or developmental stages of cells can be distinguished by the presence of different antigens on the cell surface. This enables for selective trapping of the desired cells by choosing a biomolecule such as an antibody or fragment thereof attached to the carrier of the invention, wherein said biomolecules specifically binds to one of said antigens. In the case of trapping fetal cells, application of the device of the invention avoids potentially dangerous techniques such as amniocentesis in that a blood sample obtained from the mother is used for trapping fetal cells without endangering the fetuses' life. Furthermore, the diagnosis of a cancerous disease and its characterization is facilitated by the provision of enriched tumor cell samples.

The term "patient" as used throughout the present invention comprises ill or diseased as well as healthy subjects. A patient in accordance with the present invention is any person who receives medical attention, care, or treatment. The person is most often but not always ill or injured and, if so, in need of treatment by a physician or other medical professional. In other terms, the term "patient" is interchangeably used with "subject" which may or may not be ill. The subject can be an animal, preferably a mammal, most preferably a human. In accordance with the above, a patient is also, for example, a healthy human who is, on an acute or routine basis, diagnosed for a disease or health status. In other terms, the invention may be used to find out whether a patient suffers from a certain disease (or a combination of diseases), is prone to develop such a disease or combination thereof or not.

One embodiment of the device includes transient or permanent implants characterized by a surface which corresponds, at least in part, to a solid coated carrier of the invention or to which solid coated carriers of the invention are attached.

This includes osteosynthesis devices, materials used for reconstructive surgery etc. as well as novel classes of stents. Such novel classes of stents may have catalyzing features (e.g. stimulatory, inhibitory or eliminating features). In this regard, an exemplary stimulatory feature could be a carrier-bound antibody or fragment thereof that cross-links receptors on a cell surface and that can activate cells such as leukocytes. An exemplary inhibitory feature is a carrier-bound antibody or fragment thereof which binds to receptors on the cell surface and which can inactivate cells by either inducing inactivating signals (e. g. effecting leukocytes) or by preventing the binding of an activating molecule. An example for an eliminating feature is a carrier-bound antibody or fragment thereof which can bind soluble factors and thus reduce their concentration in the solution, e. g. deplete said factors (e. g. Ig-Therasorb® or LDL-Therasorb®).

Moreover, further alternative embodiments of the medical or diagnostic device are devices the interior walls of which are solid coated carriers of the invention or to which solid coated carriers of the present invention are attached. Such devices include, but are not limited to ex vivo vaccination containers, apheresis devices, stem cell isolation devices, purging devices, syringes and devices for transient or permanent blood storage (e.g. in blood banks, but also laboratory equipment in routine research laboratories). An example for a diagnostic (medical) device is an ELISA plate wherein the surface of the plate (or at least of the reaction wells) corresponds, at least in part, to a solid coated carrier of the invention or has attached thereto solid coated carriers of the present invention.

The present invention also relates to a sterilized container, comprising a carrier, at least one biomolecule reversibly attached to the carrier, the stabilizing composition according to the invention which partially or completely covers the attached biomolecules; and optionally a lid. The biomolecules attachable to the carrier have been described above.

In a preferred embodiment, the at least one biomolecule is attached to the carrier such that it can be quickly released from the carrier, preferably immediately prior to use. Depending on the kind of attachment, covalent or non-covalent, a quick release can e. g. be obtained by proteolytic cleavage, changes in the pH value or temperature.

In a preferred embodiment, the carrier is solid, more preferably porous. In another preferred embodiment, the carrier is semi-solid and preferably comprises a hydrogel or a gelatinous protein mixture. In yet another preferred embodiment, the carrier is soluble and preferably comprises proteinaceous and/or carbohydrate structures that dissolve in aqueous, optionally buffered solutions.

The present invention further relates to a method for producing a sterilized container for biomolecules, comprising: (a) inserting a carrier into a container; (b) reversibly attaching at least one biomolecule to said carrier; (c) incubating the carrier with the at least one reversibly attached biomolecule in the liquid stabilizing composition according to the invention, such that the at least one biomolecule is partially or completely covered by said stabilizing composition; (d) sealing the container; and (e) sterilizing the container.

In an alternative embodiment, the present invention relates to a method for producing a sterilized container for biomolecules, comprising: (a) reversibly attaching at least one biomolecule to a carrier, (b) inserting the carrier with the at least one attached biomolecule into a container, (c)

incubating said carrier with the at least one reversibly attached biomolecule in the liquid stabilizing composition according to the invention, such that the at least one biomolecule is partially or completely covered by said stabilizing composition, (d) sealing the container; and (e) sterilizing the container.

In a further alternative embodiment, the present invention relates to a method for producing a sterilized container for biomolecules, comprising: (a) reversibly attaching at least one biomolecule to a carrier, (b) incubating the carrier with the at least one reversibly attached biomolecule in the liquid stabilizing composition according to the invention, such that the at least one biomolecule is partially or completely covered by said stabilizing composition, (c) inserting the carrier with the at least one reversibly attached biomolecule into a container, (d) sealing the container; and (e) sterilizing the container.

The above methods may further comprise a step of drying or removing the liquid part of the composition after incubation as described above.

In a different embodiment, the present invention relates to a container produced by the method of the present invention.

Furthermore the invention relates to the use of a container of the invention for diagnostic or therapeutic applications as described above.

In a further embodiment the invention provides a method for diagnosing a disease comprising the steps of:
(a) contacting a sample obtained from a patient with a solid carrier of the invention under suitable conditions to allow specific binding of the biomolecules attached to the carrier which specifically bind a marker protein indicative for a disease, a, preferably non-cellular pathogen, a cell or a toxin to said pathogen or marker protein or cell or toxin; and
(b) detecting whether said marker protein indicative for the disease, said preferably non-cellular pathogen, said cell or said toxin has been bound to the biomolecules.

Samples include body liquids or fluids such as blood, plasma, serum, saliva, urine, bronchoalveolar fluid, stomach and intestine secretion, cerebrospinal fluid, ascites, pleural effusion, exudate from wounds.

Suitable conditions to allow specific binding of the biomolecules attached to the carrier which specifically bind a pathogen or marker protein indicative for a disease to said pathogen or marker protein include a pH value between 7.0 and 7.7 and an osmolarity of 200 to 400 mosmol/l.

Preferred biomolecules have been described above. Particularly preferred biomolecules comprise membrane bound and intracellular biomolecules such as receptors as well as soluble biomolecules or receptors or functional fragments thereof. Preferred functional fragments of membrane bound biomolecules contain the intracellular or the extracellular portion of said biomolecules thus omitting their transmembrane fraction. Preferably, the biomolecule or receptor is an antibody or a fragment or derivative thereof retaining its binding activity and specificity as described above. Most preferably, the antibody is a monoclonal antibody.

Examples for diseases to be diagnosed with the diagnostic method of the invention comprise the diseases described herein above. The recited pathogen or marker protein may e.g. be detected by the use of antibodies like e.g. anti-p24 (HIV) (see e.g. Schupbach et al., J. Aquir. Immune Defic. Syndr. (2005), Vol. 40, pp. 250-256) or anti-IgB (HCMV) (see e.g. Just-Nubling G. et al., Infection (2003), 318-323).

Suitable conditions for specific binding of a pathogen or marker protein indicative of the disease to the attached antibody may be achieved by contacting a sample of the body liquid of the patient with antibody covered solid carriers of the invention under physiological conditions. Physiological conditions include a pH value between 7.0 and 7.7 and an osmolarity of 200 to 400 mosmol/l.

Detection of whether the pathogen or marker protein indicative for the disease has been bound to the biomolecules can be effected by methods well known in the art and described above. Exemplary methods comprise ELISA and immunoprecipitation.

In a preferred embodiment, the diagnostic method of the invention comprises the step of incubating the material of a sample of the body liquid under cell culture conditions in order to enrich a non-cellular pathogen such as a virus, cells such as a bacterium, or a single cell eukaryotic pathogen prior to contacting the sample with the carrier of the invention (step (a)). Cell culture conditions include a pH value between 7.0 and 7.7 and an osmolarity of 200 to 400 mosmol/l in a culture medium at 25 to 40° C.

Moreover, the invention provides a diagnostic composition comprising a solid coated carrier that is post-coated according to the present invention. The diagnostic composition of the invention will preferably be used for the diagnosis of a disease using methods described above in the context of detection of marker proteins, preferably non-cellular, pathogens, cells and toxins.

Examples for diseases to be diagnosed with the diagnostic composition of the invention have been described herein above.

The invention also relates to a kit for the stabilization of immobilized biomolecules. The kit according to the invention includes (a) at least one stabilizing composition according to the present invention and (b) instructions for contacting immobilized biomolecules with an effective amount of the at least one stabilizing composition to produce a stabilized biomolecule composition.

In a preferred embodiment, the stabilizing components include one or more solid materials (e.g. lyophilized or powdered reagents or other compounds which are known in the state of the art).

The various components of the kit may be packaged in one or more containers such as one or more vials. The vials may, in addition to the components, comprise preservatives or buffers for storage.

With postcoatings consisting of 5 different amino acids after irradiation with 25 kGy approx. 65% of the antigen binding ability compared to the not irradiated control is maintained; after accelerated aging procedure (7 days at 45° C.) approx. 85% of the antigen binding ability compared to the untreated control is maintained.

Figure 4:
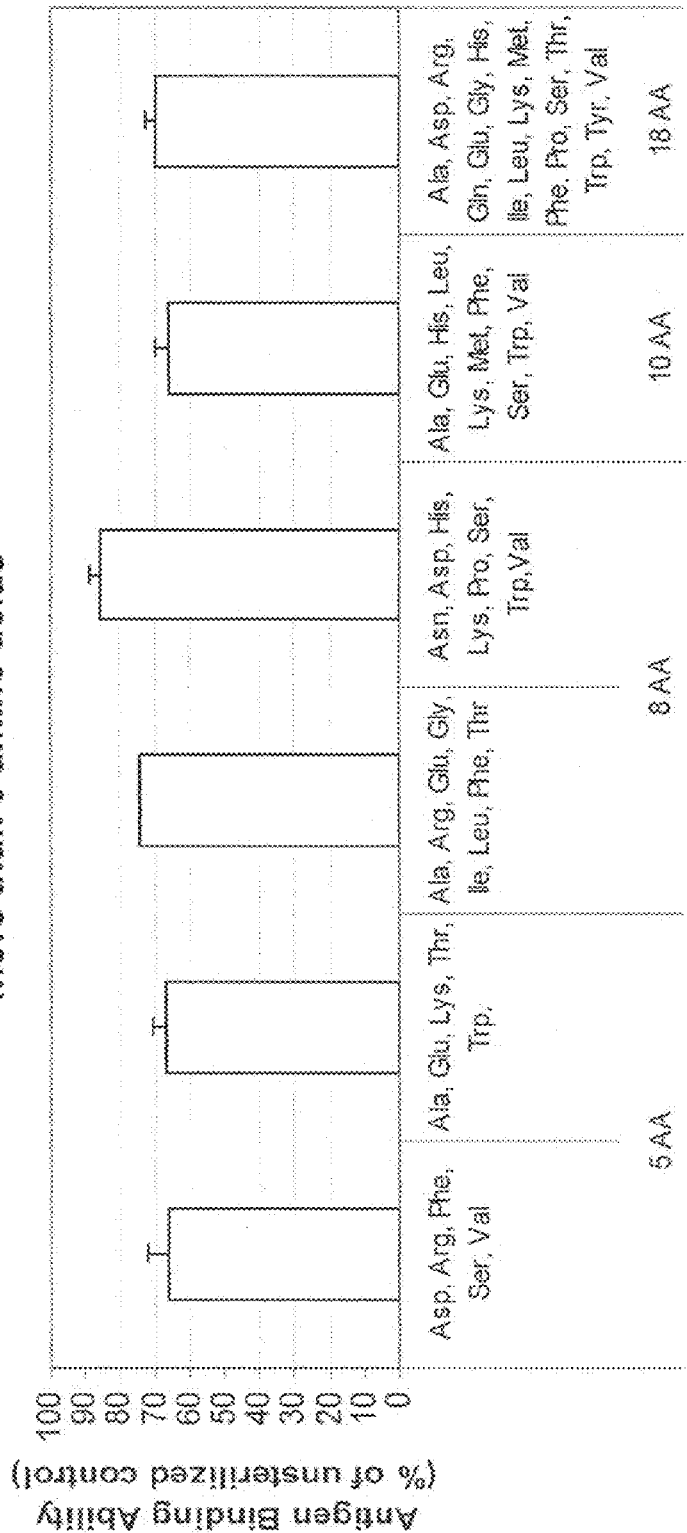
Figure 5:
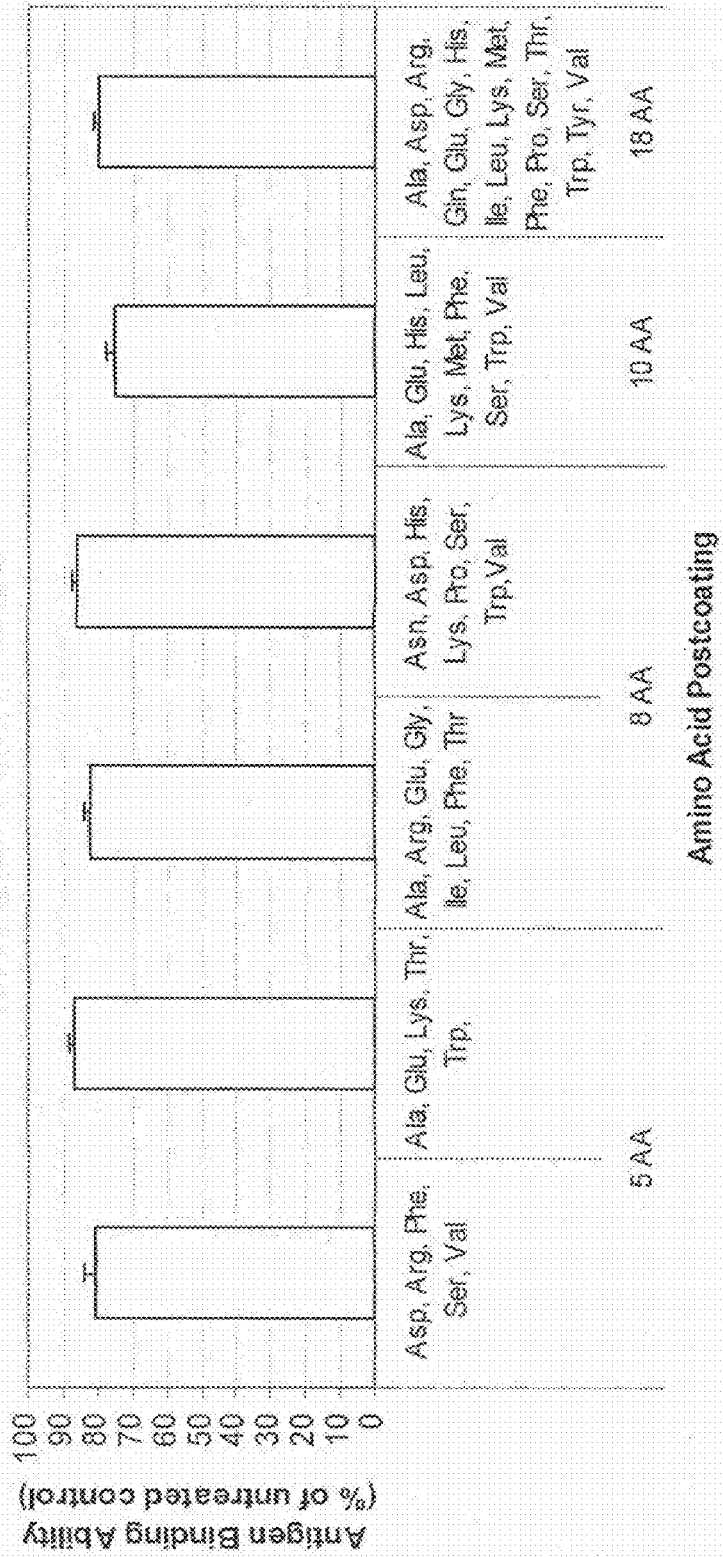

FIGS. 4 and 5: The protective effect of amino acid postcoatings cannot be further enhanced by increasing the number of amino acids above 5. After irradiation with 25 kGy about 70% antigen binding ability compared to untreated control is maintained with all postcoatings containing more than 5 amino acids; after accelerated aging (7 days at 45° C.) about 85% is maintained.

Figure 6:
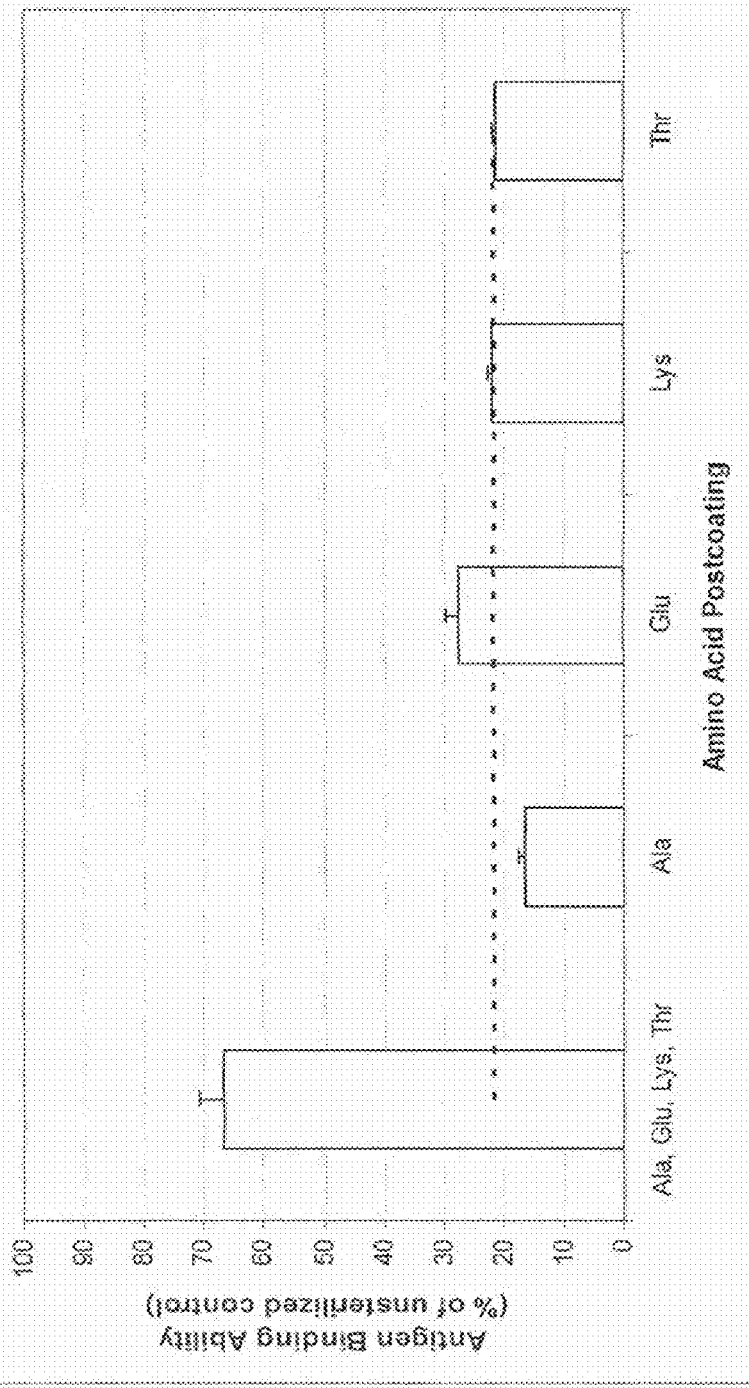
Figure 7:
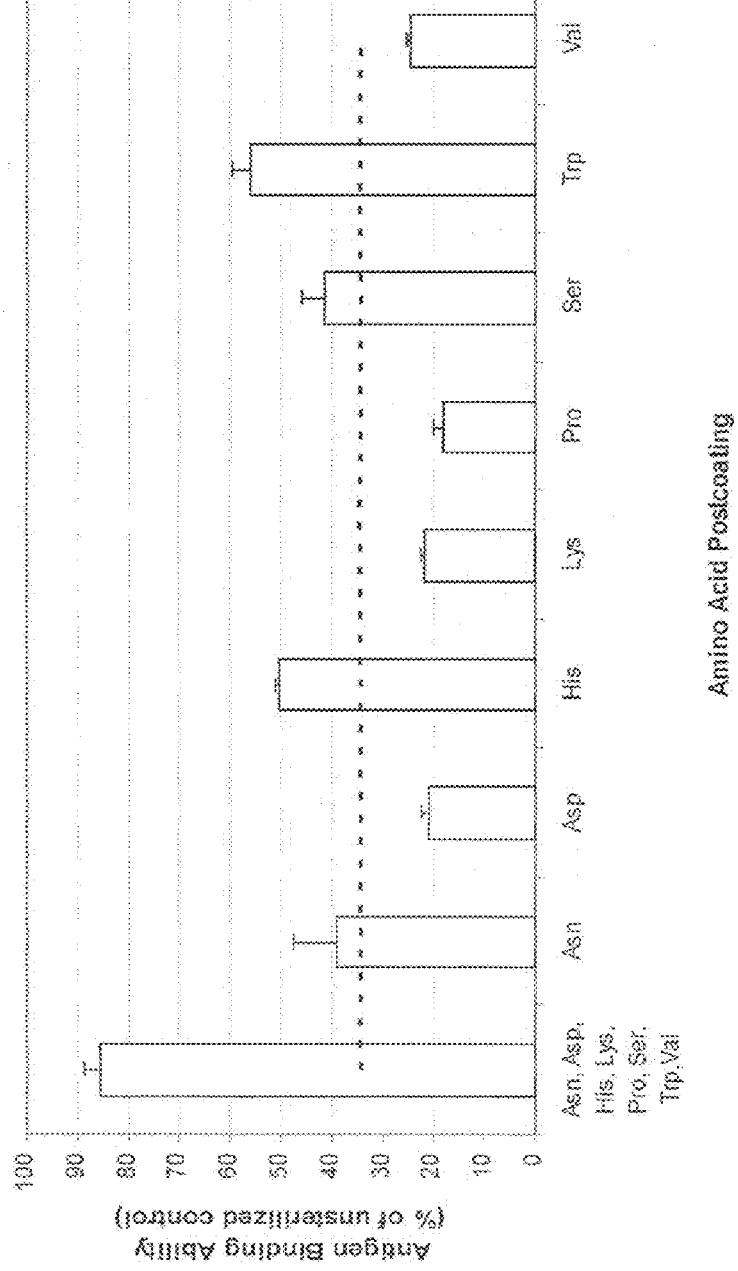

FIGS. 6 and 7: The combination of amino acids shows a protective effect of 65% (4 amino acids) respectively 85% (8 amino acids), whereas the average effect of the single amino acids is 22% (4 amino acids) respectively 33% (8 amino acids) antigen binding ability compared to the unsterilized control. The maximal effect of single amino acids is at 28% (4 amino acids) respectively 55% (8 amino acids).

Figure 8:
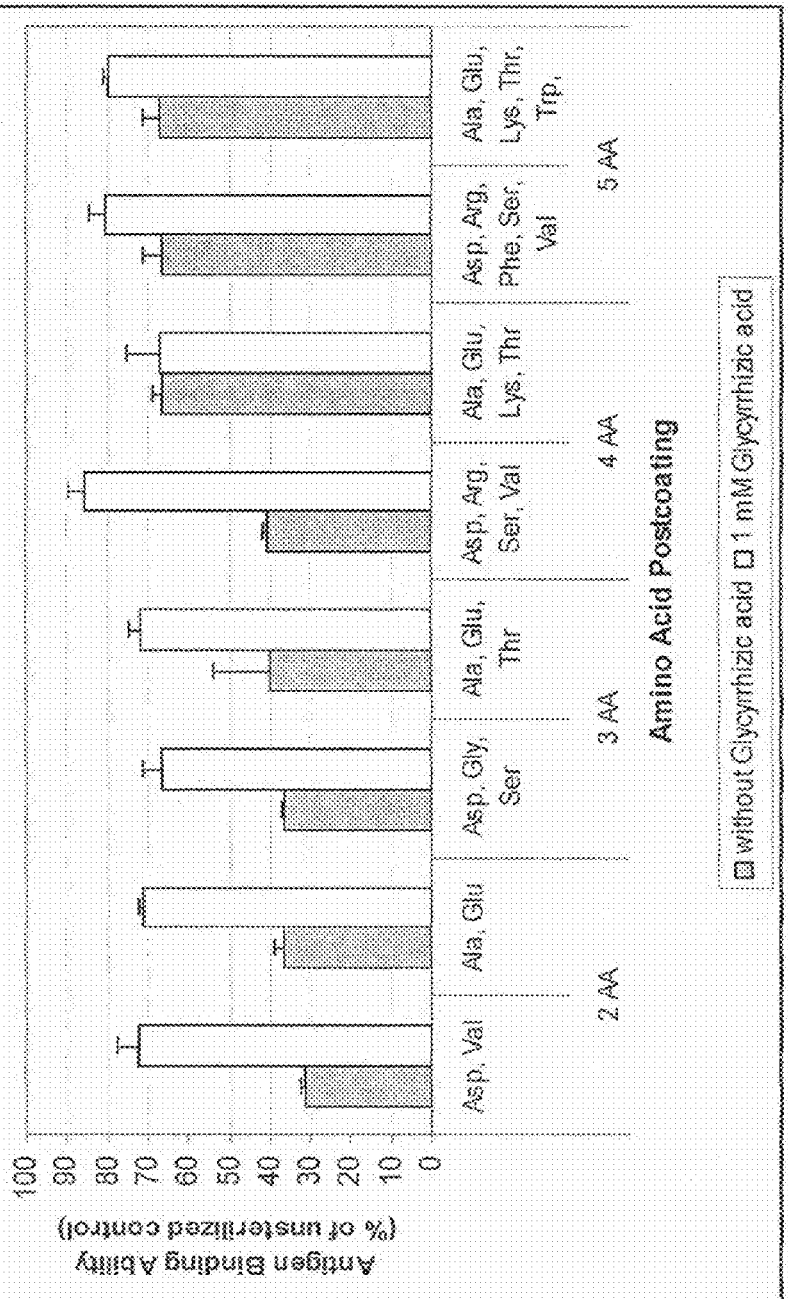

FIG. 8: The addition of 1 mM Glycyrrhizic acid to amino acid postcoatings enhances the protective effect of all postcoatings to a maximum value of 70-80% (antigen binding ability compared to not irradiated control).

Figure 9:
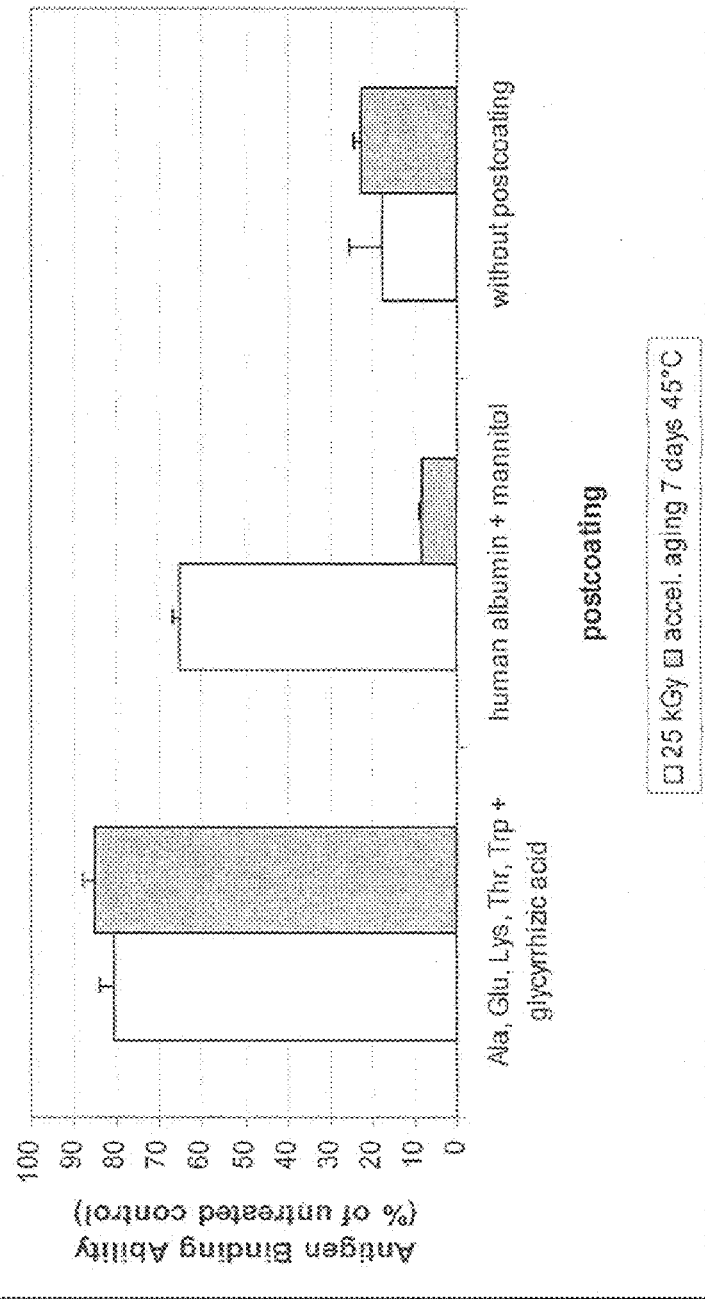

FIG. 9: An amino acid postcoating consisting of five different amino acids (200 mM) and 1 mM glycyrrhizic acid shows a protective effect of 80% antigen binding ability compared to the untreated control after irradiation (25 kGy) and 85% after accelerated aging procedure, respectively. An postcoating consisting of albumin and mannitol shows only 65% remaining activity of after irradiation (25 kGy). After accelerated aging for 7 days at 45° C. there is almost no activity remaining with albumin and mannitol, similar to the controls without any postcoating.

FIG. 10: A mixture of 18 amino acids was used to block unspecific binding to an ELISA plate without inhibiting specific antigen-antibody interactions. The blocking efficiency is comparable to standard albumin blockings.

FIG. 11: An amino acid postcoating consisting of 18 different amino acids (20 g/L) and 0.25 mM glycyrrhizic acid shows a protective effect of 83% DNAse activity compared to the untreated control after irradiation (25 kGy). An postcoating consisting of albumin and mannitol shows 95% remaining activity of after irradiation (25 kGy).

FIG. 12: An amino acid postcoating consisting of 18 different amino acids (20 g/L in PBS) shows a protective effect of 85% antigen binding ability compared to the untreated control after irradiation (25 kGy) and 90% after accelerated aging procedure, respectively. With the addition of 1 mM glycyrrhizic acid to the amino acid postcoating the protective effect is 92% antigen binding ability compared to the untreated control after irradiation (25 kGy) and 95% after accelerated aging procedure, respectively.

FIG. 13: Amino acid postcoatings consisting of 18 different amino acids (20 g/L in PBS) show a protective effect of 55-60%. Without postcoating, the amount of intact ds-DNA is reduced to 20%, with albumin and mannitol 85% are preserved.

FIG. 14: anti-Hepatitis A test (functional ELISA) of an amino acid composition used for protecting anti Hepatitis antibodies after lyophilisation and sterilization.

FIG. 15: The structural class of saponins has the potential to enhance the protective effect of amino acid combinations.

FIG. 16: Combinations of at least 3 amino acids and combinations of 2 amino acids with the addition of glycyrrhizic acid provide a maximal protection of an immobilized antibody when sterilized with 50 kGy beta irradiation.

FIG. 17: The amino acid composition provides protection under different stress conditions. The best protection is provided for beta irradiation with different doses and artificial aging under elevated temperature. The protection for gamma irradiation or ethylene oxide sterilisation is less but still relevant.

FIGS. 18 and 19: Amino acid postcoatings containing at least 5 amino acids provide protection during long time storage. For the non sterilized samples, after 62 days at 45° C. about 80% of the antigen binding ability is preserved. Sterilized samples (beta, 25 kGy) maintain about 70% of their antigen binding ability after 62 days at 45° C. Amino acid postcoatings containing only 2 amino acids maintain only about 40% antigen binding ability during the storage process, regardless of sterilization. Without postcoating only 20-30% activity is preserved.

FIGS. 20 and 21: The addition of 1 mM glycyrrhizic acid to the postcoating solutions enforces the protecting effect. Amino acid postcoatings containing at least 5 amino acids and glycyrrhizic acid provide protection during long time storage. For the non sterilized samples, after 62 days at 45° C. about 90% of the antigen binding ability is preserved. Sterilized samples (beta, 25 kGy) maintain about 80% of their antigen binding ability after 62 days at 45° C. Amino acid postcoatings containing 2 amino acids and glycyrrhizic acid maintain about 70% antigen binding ability during the storage process, regardless of sterilization. Without postcoating only 20-30% activity is preserved.

FIG. 22: Samples sterilized with gamma irradiation maintain about 85% activity when protected with an amino acid postcoating containing 18 amino acids; this effect is not further enhanced with glycyrrhizic acid; with 5 amino acids the remaining activity is 75%; with 2 amino acids only 40% are maintained. The protection with 2 amino acids is improved by the addition of glycyrrhizic acid, here the remaining activity is 65%. Samples sterilized with ETO maintain about 85% activity when protected with an amino acid postcoating containing 18 amino acids; this effect is not further enhanced with glycyrrhizic acid. Postcoatings containing 5 or 2 amino acids have only little protecting effect; the addition of glycyrrhizic acid enhances the protection marginally.

FIG. 23: Amino acid postcoating of amino acids, dipeptides or mixtures thereof, optionally together with glycyrrhizic acid.

FIG. 24

An example is shown, where the vial itself is the carrier. First, the biomolecule was attached to the carrier by drying. Subsequently, the stabilizer solution was added and also dried. The biomolecule (here interleukin 8=IL8) loses most of its biological function during subsequent sterilisation (25 kGy irradiation) if no stabilizer is added. In contrast, a stabilizer solution with different amino acids protected the biomolecule. Shown is the chemotactic activity of IL8 on human neutrophil granulocytes.

FIG. 25

An example is shown, where the vial itself is the carrier. First, the biomolecule was attached to the carrier by drying. Subsequently, the stabilizer solution was added and also dried. The biomolecule (here interleukin 8=IL8) loses most of its biological function during accelerated storage (45° C.) if no stabilizer is added. In contrast, a stabilizer solution with different amino acids protected the biomolecule. Shown is the chemotactic activity of IL8 on human neutrophil granulocytes.

FIG. 26

An example is shown, where the vial itself is the carrier. First, the biomolecule was attached to the carrier by drying. Subsequently, the stabilizer solution was added and also dried. The biomolecule (here ds-DNA) loses part of its biological function during subsequent sterilisation (25 kGy irradiation) if no stabilizer is added. In contrast, a stabilizer solution with different amino acids protected the biomolecule. Shown is the detectable DNA amount in percent of starting value.

FIG. 27

An example is shown, where the stabilizer itself is the carrier. The biomolecule and the stabilizer solution were added and dried together. The biomolecule (here interleukin 8=IL8) loses most of its biological function during subsequent sterilisation (25 kGy irradiation) if no stabilizer is added. In contrast, a stabilizer solution with different amino acids protected the biomolecule. Shown is the chemotactic activity of IL8 on human neutrophil granulocytes.

FIG. 28

An example is shown, where the stabilizer itself is the carrier. The biomolecule and the stabilizer solution were added and dried together. The biomolecule (here an anti-mouse IgG antibody) loses most of its biological function during subsequent storage and or sterilisation (25 kGy irradiation) if no stabilizer is added. In contrast, a stabilizer solution with different amino acids protected the biomolecule. Shown is the specific binding to the antigen.

FIG. 29

Influence of different desorption solutions on the biological activity of a biomolecule (here an anti-mouse IgG antibody). With the exception of 0.5 M H2SO4 none of the other desorption solutions tested in this experiment had a significant influence on the biological activity of the biomolecule. Shown is the specific binding to the antigen.

FIG. 30

The desorption of a biomolecule (here an anti-mouse IgG antibody) is tested after the biomolecule was attached to an open porous polyurethane foam (supplier A, large pores). While citrate buffer pH 4.75 and 1 M NaCl only desorbed small amounts of the biomolecule, significantly more biomolecule could be desorbed with 1M NaCl+0.02 M imidazole and phosphate buffered saline, respectively. Shown is the specific binding to the antigen.

FIG. 31

The desorption of a biomolecule (here an anti-mouse IgG antibody) is tested after the biomolecule was attached to an open porous polyurethane foam (supplier B, smaller pores). Citrate buffer pH 4.75 and phosphate buffered saline desorbed a little bit better than 1 M NaCl with or without 0.02 M imidazole. Shown is the specific binding to the antigen.

FIG. 32

The desorption of a biomolecule (here an anti-mouse IgG antibody) is tested after the biomolecule was attached to an open porous polyurethane foam (supplier Smith&Nephews, small pores). The biomolecule (here an anti-mouse IgG antibody) loses most of its biological function during subsequent storage and or sterilisation (25 kGy irradiation) if no stabilizer is added. In contrast a stabilizer solution with different amino acids protected the biomolecule. The recovery of the antibody is almost 100% (5 µg/mL). Shown is the specific binding to the antigen.

FIG. 33

The desorption of a biomolecule (here an anti-mouse IgG antibody) is tested after the biomolecule was attached to an PVA-hydrogel. The biomolecule loses most of its biological function during subsequent storage and or sterilisation (25 kGy irradiation) if no stabilizer is added. In contrast, a stabilizer solution with different amino acids protected the biomolecule. The recovery of the eluted antibody is very high. Shown is the specific binding to the antigen.

FIG. 34

Chemical Structures of examples for cleavable linkers

EXAMPLES

The examples illustrate the invention.

Materials & Methods

All experiments were based on the same basic ELISA assay design.

Adsorption of LO-MM-3 to an ELISA Plate and Application of Postcoatings

A monoclonal antibody LO-MM-3 (anti-mouse-IgM, Acris, SM1495P) was adsorbed to the surface of a 96 well ELISA plate (Greiner Bio-one, 655061). LO-MM-3 was diluted in PBS (without $Ca^{2+}/Mg^{2+}$, PAA, H15-002) to a concentration of 2 µg/mL. 100 µL of the antibody solution was pipetted to each well and incubated over night at 5° C. The plate was washed 2 times with washing buffer (25× concentrate, Invitrogen, WB02).

200 µL of each assayed stabilizing composition (postcoating) were pipetted per well. At least 4 wells were treated identically with the same postcoating to calculate means and standard deviations in the following analysis. The plate was incubated with the postcoating solutions for 1 hour at ambient temperature. The postcoatings were discarded and the plate was dried at ambient temperature for at least 1 hour.

Amino acids used for postcoatings: L-alanine (Sigma-Aldrich, A7627), L-arginine (Sigma-Aldrich, A5131), L-asparagine (Sigma-Aldrich, A0884), L-aspartate (Sigma-Aldrich, A9256), L-cysteine (Sigma-Aldrich, 1276), L-glutamine (AppliChem, A1420), L-glutamate (Sigma-Aldrich, G1251), glycine (Merck, 1042010), L-histidine (Sigma-Aldrich, H8125), L-isoleucine (Sigma-Aldrich, I2752), L-leucine (Sigma-Aldrich, L8000), L-lysine (Sigma-Aldrich, L5626), L-methionine (Sigma-Aldrich, M9625), L-phenylalanine (Sigma-Aldrich, P2126), L-proline (Sigma-Aldrich, P0380), L-serine (Sigma-Aldrich, S4500), L-threonine (Sigma-Aldrich, T8625), L-tryptophan (Sigma-Aldrich, T0254), L-tyrosine (Sigma-Aldrich, T3754), L-valine (Sigma-Aldrich, V0500)

Stress Exposure of the Coated Surface

Three identically treated plates were exposed to different environmental conditions. One plate was sterilized by irradiation (beta, 25 kGy). The irradiation was conducted at Beta-Gamma-Service, Bruchsal, Germany. One plate was treated with an accelerated aging procedure (7 days at 45° C.). Based on a simplification of the Arrhenius equation it is assumed that by increasing the storage temperature by 10° C., the speed of reaction, i.e. aging, is doubled (Hemmerich, 1998: *General Aging Theory and Simplified Protocol for Accelerated Aging of Medical Devices*). This implies that an accelerated aging for 7 days at 45° C. equals a real time aging of 16 weeks of cooled storage (5° C.).

An identical plate without stress exposition served as a control in each experiment. The protective effect was calculated as the remaining antibody functionality after stress conditions compared to the untreated control.

$$\text{functionality}(\%) = \frac{\text{stressed plate} \cdot 100}{\text{control plate}}$$

ELISA Detection of LO-MM-3 Functionality

The dried postcoatings were removed from the wells by washing the plate 3 times. The ELISA plate was blocked by pipetting 300 µL blocking solution (10 g/L albumin in PBS) to each well and incubating for 1 hour at ambient temperature. The plate was washed 3 times.

The antigen to LO-MM-3, CH11 (mouse IgM, MBL, SY001), was diluted to 125 ng/mL and 200 µL of the antigen solution was pipetted to each well. The plate was incubated for 1 hour at ambient temperature and washed 3 times.

The bound antigen was detected by a detection antibody LO-MM-9 (biotinylated anti-mouse-IgM, AbD serotec, MCA199B), which was diluted with PBS to 50 ng/mL. To each well 200 µL were added and incubated for 1 hour at ambient temperature. The plate was washed 3 times.

Streptavidin (Horseradish peroxidase (HRP) labeled, Pierce, 21126) was diluted with PBS to 100 ng/mL. 200 µL were added to each well and incubated for 1 hour at ambient temperature. The plate was washed 3 times.

A ready-to-use ELISA substrate solution for HRP (TMB=tetramethylbenzidine, Invitrogen, 00-2023) was diluted 1:2 with aqua dest. and 200 µL were pipetted to each well. The plate was incubated for 20 minutes at ambient temperature and protected from light. To stop the colour reaction, to each well 50 µL of $H_2SO_4$ (diluted 1:5 with aqua dest., Merck, 1007311000) were added. The resulting yellow color was detected by measuring the absorption at a wavelength of 450 nm (Fusion Photometer A153601, PerkinElmer).

Example 1: Postcoatings Consisting of at Least 5 Amino Acids Show a Maximal Protection Against Stress Experiment:

The amino acids were dissolved either in 0.5 M NaOH (Merck, 106482) or 0.5 M HCl (Merck, 100319) to obtain stock solutions with a maximal concentration. The amino acid stock solutions were mixed together to get a total amino acid concentration of 200 mM in the postcoating solution. The amino acids were used in equimolar ratio (2 amino acids: 2×100 mM; 3 amino acids: 3×67 mM; 4 amino acids: 4×50 mM, 5×40 mM; etc.)

The pH of the amino acid mixtures was set to approx. 7.0; and the mixtures were further diluted in PBS to get the final concentration of 200 mM.

Adsorption of LO-MM-3 to the plate and application of the postcoating; sterilization and accelerated aging; as well as the general ELISA procedure were conducted as described in the Materials & Methods section.

Figure 2:
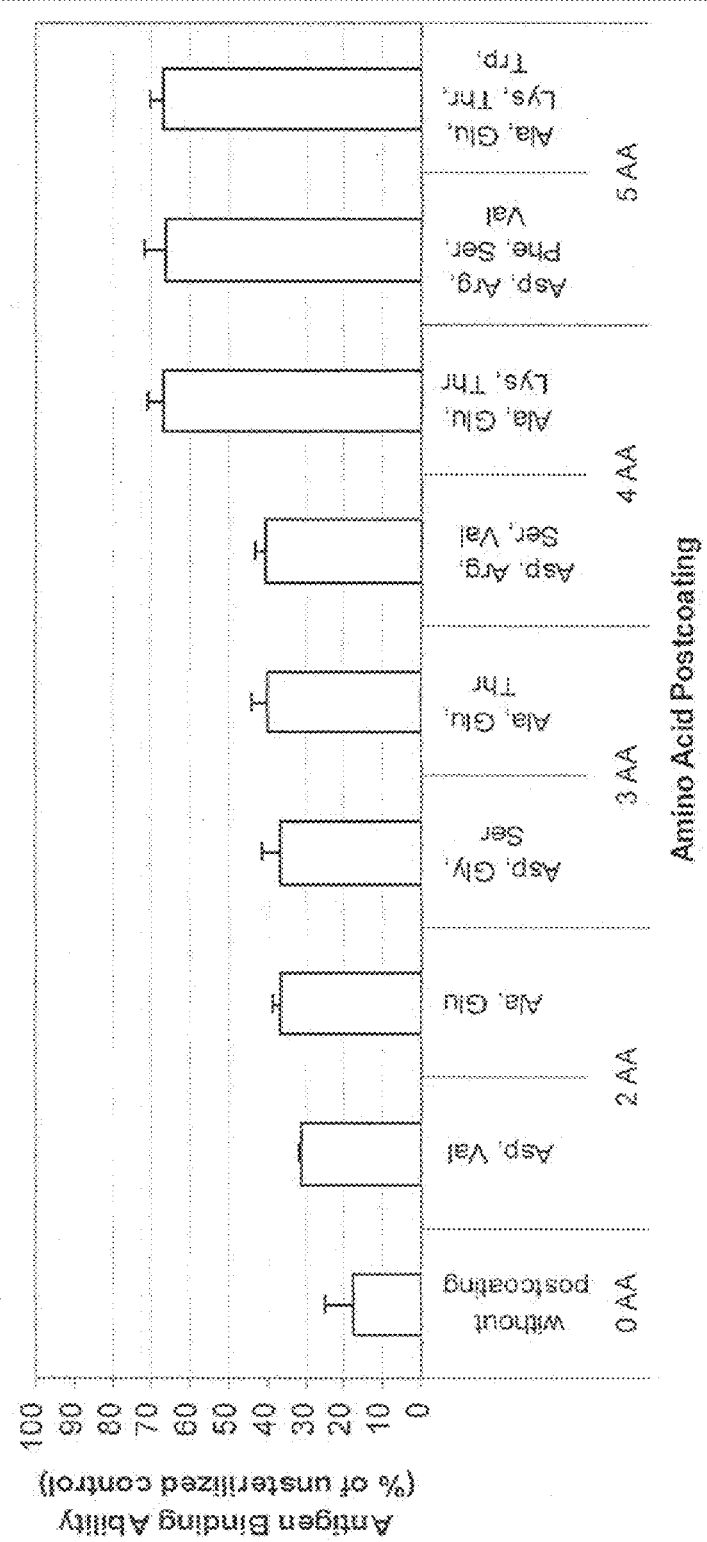
FIGS. 2 and 3: The protective effect of amino acid postcoatings increases with the number of different amino acids used (independent of the amino acid). The amino acids were selected as representatives of the following groups: amino acids with aromatic/positively charged/negatively charged/polar non-charged/non polar aliphatic side-chain.
Figure 3:
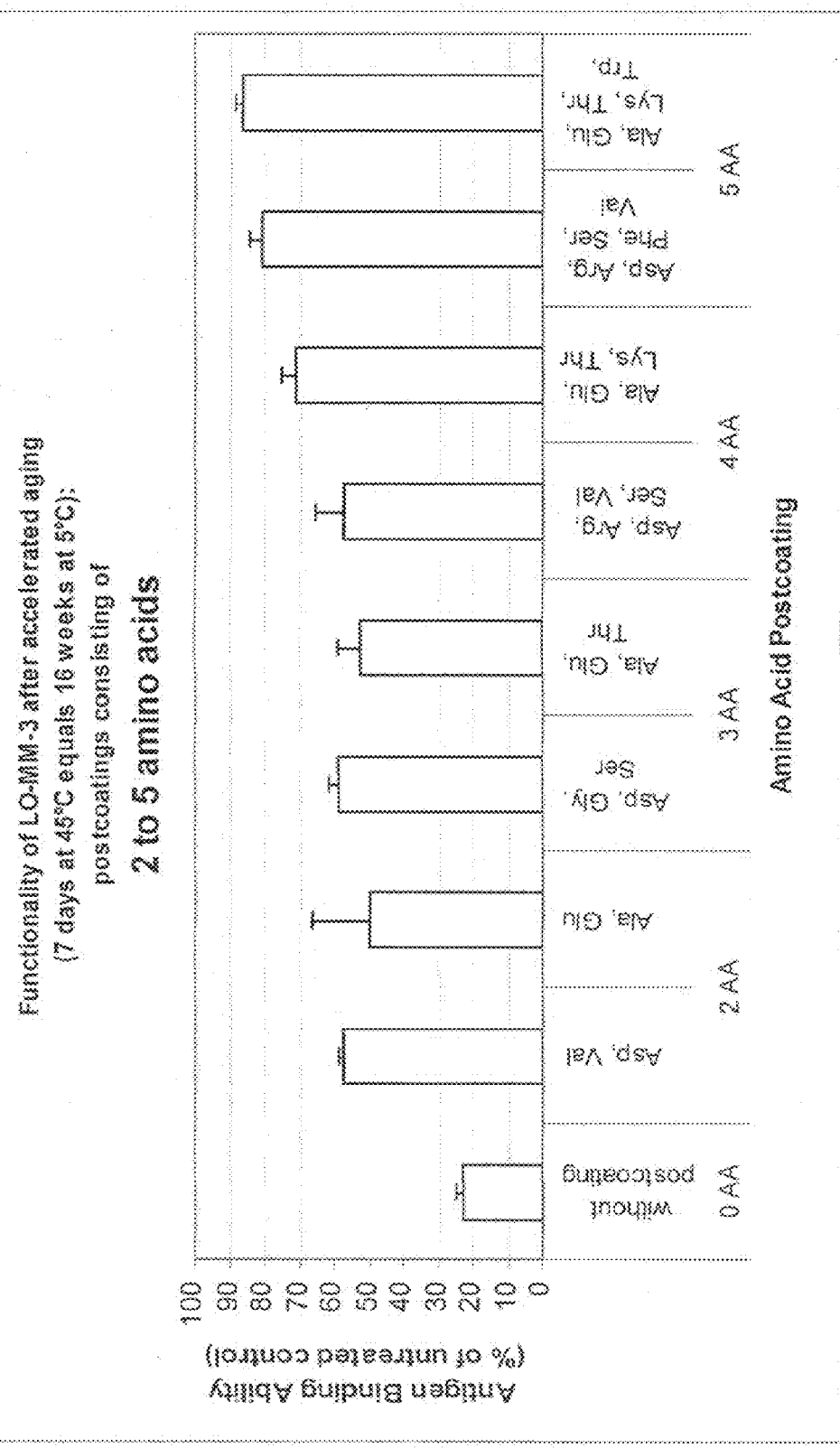

Results:

As shown in FIGS. 2 and 3, the protective effect of amino acid postcoatings increases with the number of different amino acids used. The amino acids were selected as representatives of the following groups: amino acids with aromatic/positively charged/negatively charged/polar non-charged/non polar aliphatic side-chain. It is not essential to use particular amino acids; they can be substituted with a different amino acid from the same group, or with similar characteristics respectively (Taylor, 1985: *The Classification of Amino Acid Conservation*).

Figure 1:
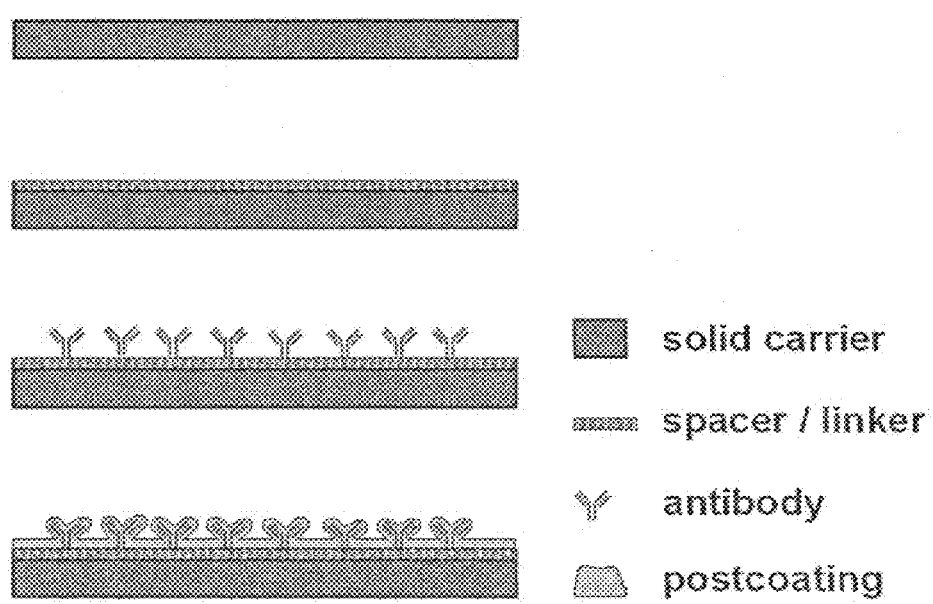
FIG. 1: A biomolecule, e.g. an antibody is attached to a solid carrier, preferably by use of spacer or linker molecules. The antibody is embedded by the postcoating solution and thereby protected of stress influences like irradiation.

With postcoatings consisting of 5 different amino acids after irradiation with 25 kGy approx. 65% of the antigen binding ability compared to the non-irradiated control is maintained (FIG. 1); after accelerated aging procedure (7 days at 45° C.) approx. 85% of the antigen binding ability compared to the untreated control is maintained (FIG. 2).

The protective effect of amino acid postcoatings cannot be further enhanced by increasing the number of amino acids above 5. As shown in FIGS. 4 and 5, postcoatings with 8, 10 or even 18 amino acids have virtually the same effect.

Example 2: The Combination of Amino Acids Reveals a Protective Effect not Attributed to One Particular Single Amino Acid Experiment:

The amino acids were dissolved either in 0.5 M NaOH (Merck, 106482) or 0.5 M HCl (Merck, 100319) to obtain stock solutions with a maximal concentration. The amino acid stock solutions were mixed together to get a total amino acid concentration of 200 mM in the postcoating solution. The amino acids were used in equimolar ratio (4 amino acids: 4×50 mM; 8 amino acids: 8×25 mM). For the single amino acid solutions the amino acids were dissolved in aqua dest. at the maximal soluble concentration, if possible 400 mM. The pH of all postcoating solutions was set to approx. 7.0. Concentrations of the single amino acids: Ala 400 mM, Glu 100 mM, Lys 400 mM, Thr 400 mM, Asn 200 mM, Asp 100 mM, His 300 mM, Pro 400 mM, Ser 400 mM, Trp 60 mM, Val 400 mM.

Adsorption of LO-MM-3 to the plate and application of the postcoating; sterilization and accelerated aging; as well as the general ELISA procedure were conducted as described in the Materials & Methods section.

Result:

As can be seen in FIGS. 6 and 7, the protective effect of an amino acid mixture cannot be attributed to a protective effect of one single amino acid of the mixture.

The combination of amino acids shows a protective effect of 65% (4 amino acids) and 85% (8 amino acids), whereas the average effect of the single amino acids of those mixtures is 22% (4 amino acids) and 33% (8 amino acids) antigen binding as ability compared to the unsterilized control. The maximal effect of single amino acids is at 28% (4 amino acids) and 55% (8 amino acids).

Example 3: The Addition of Glycyrrhizic Acid to the Solution Further Increases the Protective Effect of Amino Acid Postcoatings Experiment:

The amino acids were dissolved either in 0.5 M NaOH (Merck, 106482) or 0.5 M HCl (Merck, 100319) to obtain stock solutions with a maximal concentration. The amino acid stock solutions were mixed together to get a total amino acid concentration of 200 mM in the postcoating solution. The amino acids were used in equimolar ratio (2 amino acids: 2×100 mM; 3 amino acids: 3×67 mM; 4 amino acids: 4×50 mM; etc.). Glycyrrhizic acid (ammonium salt, Fluka, 50531) was dissolved in 50% ethanol (absolute, Sigma-Aldrich, 32205) to obtain a 25 mM stock solution. Glycyrrhizic acid was diluted 1:25 to obtain a concentration of 1 mM in the postcoating solutions.

The pH of the amino acid mixtures was set to approx. 7.0; and the mixtures were further diluted in PBS to get the final amino acid concentration of 200 mM.

Adsorption of LO-MM-3 to the plate and application of the postcoating; sterilization and accelerated aging; as well as the general ELISA procedure were conducted as described in the Materials & Methods section.

Results:

The addition of glycyrrhizic acid to different amino acid postcoatings enhances the protective effect of all postcoatings to a maximum value of 75-80% (antigen binding ability compared to unirradiated control) as shown in FIG. 8. Glyzyrrhizic acid alone does not have a protective effect as a postcoating.

Example 4: Amino Acid Postcoatings Provide a Protection Against Stress Conditions at Least Comparable to Postcoatings Containing Conventional Protecting Substances Like Albumin and Mannitol Experiment:

The amino acid postcoating was prepared as described in example 3. Human albumin was used at a concentration of 20 g/L and mannitol at 10 g/L, diluted in PBS.

Adsorption of LO-MM-3 to the plate and application of the postcoating; sterilization and accelerated aging; as well as the general ELISA procedure were conducted as described in the Materials & Methods section.

Results:

As depicted in FIG. 9, amino acid postcoatings provide a protective effect comparable to or even better than postcoatings based on albumin and mannitol, depending on the form of stress applied.

An amino acid postcoating consisting of five different amino acids (200 mM) and 1 mM glycyrrhizic acid shows a protective effect of 80% antigen binding ability compared to the untreated control after irradiation (25 kGy) and 85% after accelerated aging procedure, respectively. The postcoating consisting of albumin and mannitol shows 65% activity of the untreated control after irradiation (25 kGy). After accelerated aging for 7 days at 45° C. there is almost no activity remaining with albumin and mannitol, similar to the controls without any postcoating.

Example 5: Amino Acid Mixtures Block Unspecific Binding, e.g. to ELISA Plates Experiment:

LO-MM-3 was adsorbed to an ELISA plate as described in material & methods. The plate surface was blocked by incubating the wells with 300 µL blocking solution for 1 h at ambient temperature. As blocking either 10 g/L human albumin in PBS or 20 g/L of a mixture of 18 amino acids in PBS were used. The following ELISA procedure was conducted as described in the Materials & Methods section.

Figure 10:
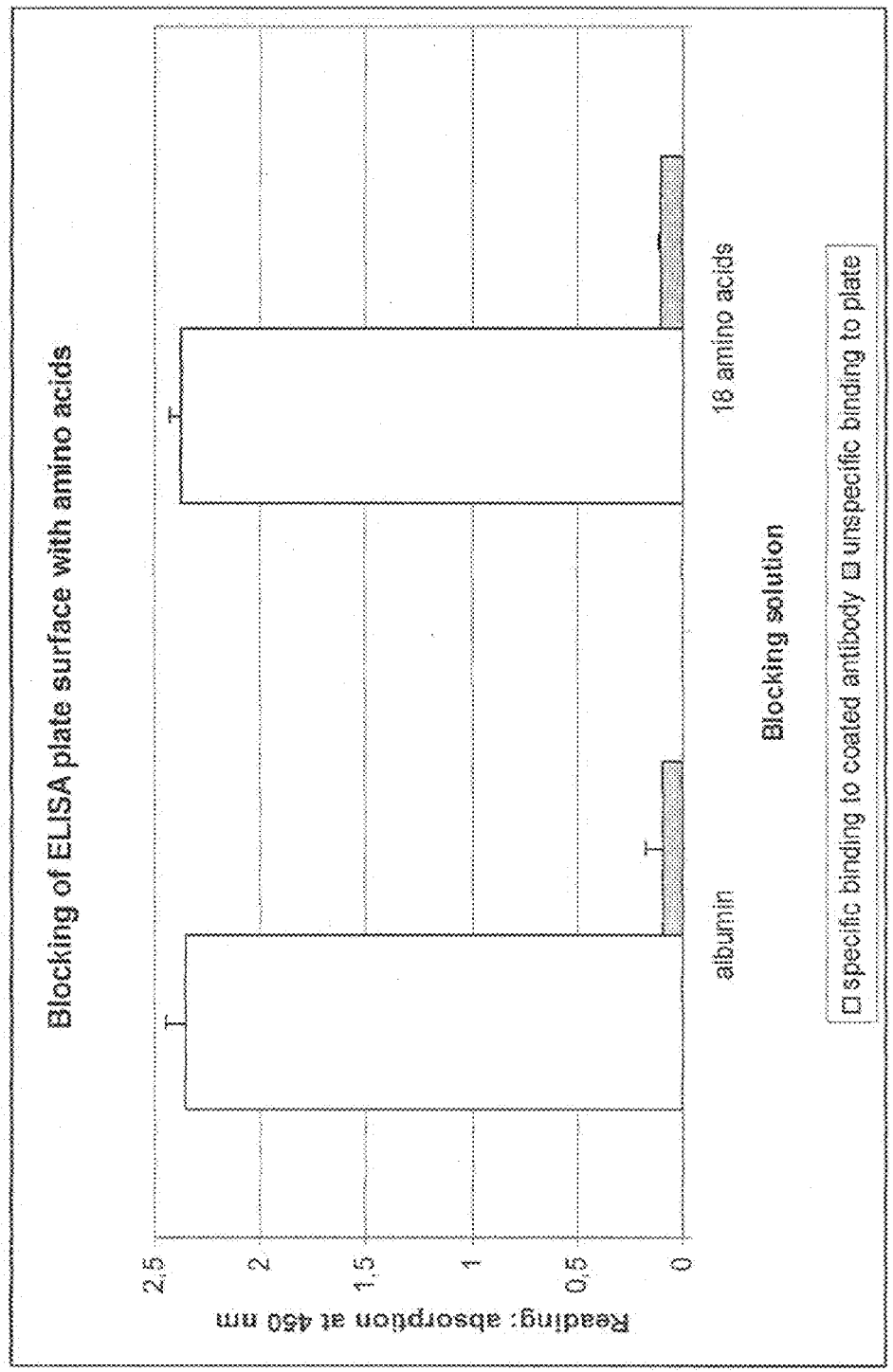

Results:

Amino acid mixtures can also block unspecific binding to surfaces, as shown in FIG. 10. A mixture of 18 amino acids blocks unspecific binding to an ELISA plate without inhibiting specific antigen-antibody interactions. The blocking efficiency is comparable to standard albumin blockings.

Example 6: Amino Acid Mixtures Provide Protection Against Stress for Enzymes Like DNAse Experiment:

Adsorption of DNAse to an ELISA Plate and Application of Postcoatings

The enzyme DNAse (Sigma Aldrich, DN25) was adsorbed to the surface of a 96 well ELISA plate (Greiner Bio-one, 655061). DNAse was diluted in PBS (without $Ca^{2+}/Mg^{2+}$, PAA, H15-002) to a concentration of 1 mg/mL. 100 µL of the enzyme solution was pipetted to each well and incubated over night at 5° C. The plate was washed 2 times with $PBS^{-/-}$.

Four wells were treated identically to calculate means and standard deviations in the following analysis. Unspecific binding to the plate was blocked with 200 µL blocking solution per well and incubated for 1 hour at ambient temperature. The plate was washed 2 times with $PBS^{-/-}$. 200 µL of each postcoating were pipetted per well. The plate was incubated with the postcoating solutions for 1 hour at ambient temperature. The postcoatings were discarded and the plate was dried at ambient temperature.

Blocking and Postcoating Solutions:
Blocking:
  20 g/L human albumin (Biotest Pharma) in $PBS^{-/-}$
Postcoating:
  20 g/L human albumin+10 g/L mannitol (Serag Wiesner, 219675) in $PBS^{-/-}$
Blocking:
  20 g/L amino acids (Ala, Asp, Arg, Gln, Glu, Gly, His, Ile, Leu, Lys, Met, Phe, Pro, Ser, Thr, Trp, Tyr, Val) in $PBS^{-/-}$
Postcoating:
  20 g/L amino acids (Ala, Asp, Arg, Gln, Glu, Gly, His, Ile, Leu, Lys, Met, Phe, Pro, Ser, Thr, Trp, Tyr, Val)+0.25 mM glycyrrhizic acid (ammonium salt, Fluke, 50531) in $PBS^{-/-}$ Stress Exposure of the Coated Surface One plate was sterilized by irradiation (beta, 25 kGy). The irradiation was conducted at Beta-Gamma-Service, Bruchsal, Germany.

An identical plate without stress exposure served as a control. The protective effect was calculated as the remaining DNAse functionality after stress conditions compared to the untreated control.

$$\text{functionality}(\%) = \frac{\text{stressed plate} \cdot 100}{\text{control plate}}$$

Detection of DNAse Functionality

The plate was washed 3 times with $PBS^{-/-}$. Ds-DNA Standard (Sigma Aldrich, D1501) was diluted to 1 µg/mL in PBS (with $Ca^{2+}/Mg^{2+}$, Hyclone, SH3026401). To each well 50 µL of the DNA-solution were added and incubated for 1 hour at 37° C. The fluorescent DNA-dye Picogreen (Molecular Probes, P7581) was diluted 1:1000 (PBS) and 150 µL of the dye were added to the DNA-solution in each well.

The picogreen fluorescence was measured, the excitation filter was set to 485 nm and the emission was detected at 530 nm (Fusion Photometer A153601, PerkinElmer). The fluorescence signal correlates to the DNA concentration. DNAse activity was determined as the reduction of DNA, i.e. fluorescence signal.

Figure 11:
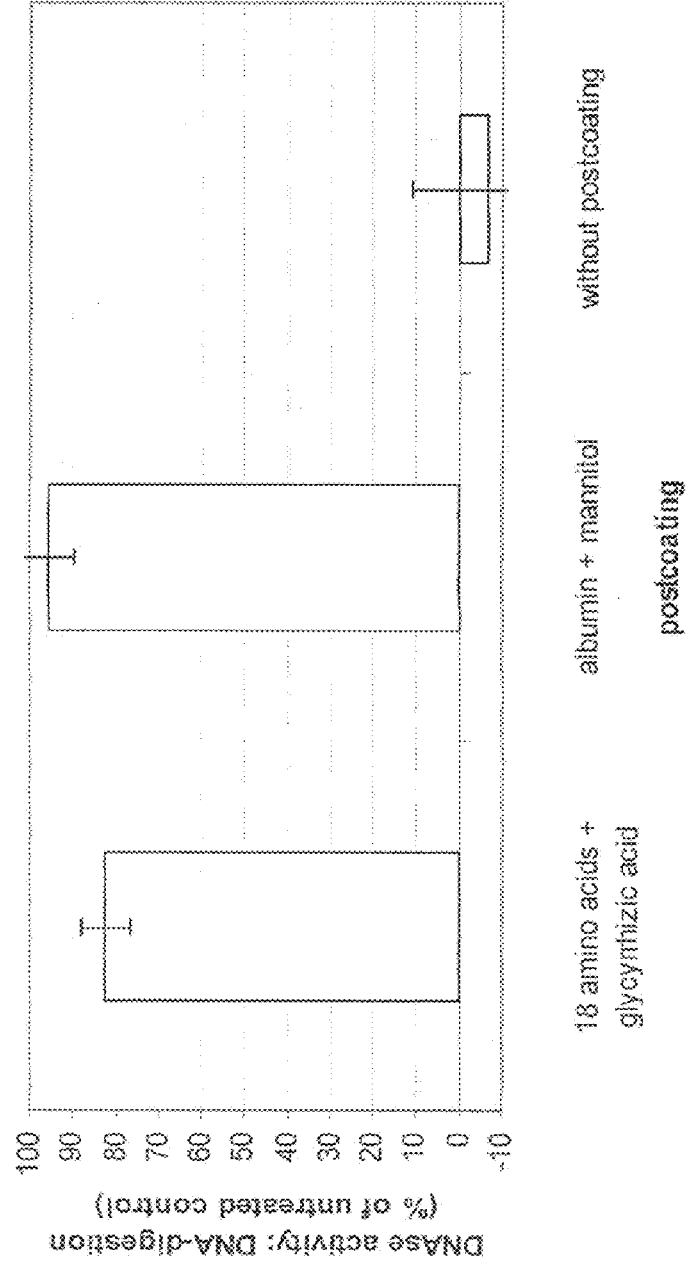

Results:

As depicted in FIG. 11, amino acid postcoatings provide a protective effect against stress (irradiation) also for enzymes like DNAse. The protection is comparable to that of poscoatings based on albumin and mannitol An amino acid postcoating consisting of 18 different amino acids (20 g/L) and 0.25 mM glycyrrhizic acid shows a protective effect of 83% DNAse activity compared to the untreated control after irradiation (25 kGy). The postcoating consisting of albumin and mannitol shows 95% activity of the untreated control after irradiation (25 kGy).

Example 7: Amino Acid Postcoatings Provide a Protection Against Stress Conditions for Therapeutic Antibodies Like IgG Infliximab Experiment:

The therapeutic antibody Infliximab (humanized IgG, anti-Human-TNF-α, Centocor, DD7701504) was adsorbed to the ELISA plate surface. Infliximab was diluted with PBS-/- to a concentration of 1 µg/mL and 100 µL of the solution was pipetted to each well. The plate was incubated over night at 5° C. and washed 2× with washing buffer.

Application of the postcoating; sterilization and accelerated aging were conducted as described in the Materials & Methods section.

ELISA Detection of Infliximab Functionality

The dried postcoatings were removed from the wells by washing the plate 3 times. The ELISA plate was blocked by pipetting 300 µL blocking solution (10 g/L albumin in PBS) to each well and incubating for 1 hour at ambient temperature. The plate was washed 3 times.

The antigen to Infliximab, TNF-α (recombinant human, R&D, Cat 210-TA), was diluted to 1 ng/mL and 200 µL of the antigen solution was pipetted to each well. The plate was incubated for 1 hour at ambient temperature and washed 3 times.

The bound antigen was detected by a detection antibody (HRP labelled anti-human-TNF-α, R&D, Cat DTA00C). The ready-to-use-solution of the detection antibody was diluted 1:2 with PBS. To each well 200 µL were added and incubated for 1 hour at ambient temperature. The plate was washed 3 times.

200 µL of a ready-to-use ELISA substrate solution for HRP (TMB=tetramethylbenzidine) were pipetted to each well. The plate was incubated for 20 minutes at ambient temperature and protected from light. To stop the color reaction, to each well 50 µL of $H_2SO_4$ (diluted 1:5 with aqua dest.) were added. The resulting yellow colour was detected by measuring the absorption at a wavelength of 450 nm.

Figure 12:
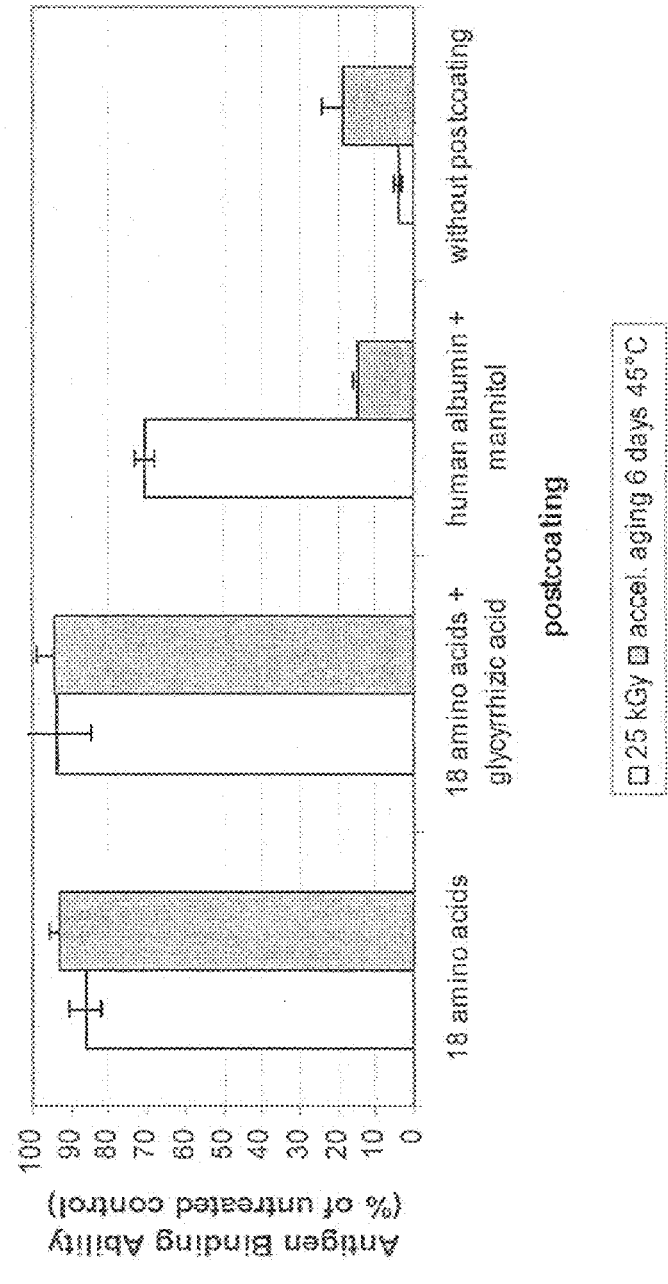

Results:

As depicted in FIG. 12, amino acid postcoatings with or without glycyrrhizic acid provide a protective effect comparable to or even better than poscoatings based on albumin and mannitol, depending on the form of stress applied.

An amino acid postcoating consisting of 18 different amino acids (20 g/L in PBS) shows a protective effect of 85% antigen binding ability compared to the untreated control after irradiation (25 kGy) and 90% after accelerated aging procedure, respectively. With the addition of 1 mM glycyrrhizic acid to the amino acid postcoating the protective effect is 92% antigen binding ability compared to the untreated control after irradiation (25 kGy) and 95% after accelerated aging procedure, respectively. The postcoating consisting of albumin and mannitol shows 72% activity of the untreated control after irradiation (25 kGy). After accelerated aging for 6 days at 45° C. there is only 15% activity remaining with albumin and mannitol, similar to the controls without any postcoating.

Example 8: Amino Acid Postcoatings Provide a Protection Against Stress Conditions for Nucleic Acids (dsDNA)

Experiment:

Ds-DNA (Sigma, D1501) was adsorbed to the ELISA plate surface. The DNA was dissolved in $PBS^{-/-}$. (1 mg/mL) with 1 mM EDTA (Fluka, 50531) to inhibit possible DNAse activity. The DNA was diluted with PBS 1:64 to 15 µg/mL and 100 µL of the solution was pipetted to each well. The plate was incubated over night at 5° C. and washed 2× with $PBS^{-/-}$.

Application of the postcoating and sterilization were conducted as described in the Materials & Methods section.

Detection of Intact Ds-DNA with Picogreen

The dried postcoatings were removed from the wells by washing the plate 3 times. To each well 100 µL Picogreen dye (diluted 1:1000 in $PBS^{-/-}$, Molecular Probes, P7581) were added. The picogreen fluorescence was measured immediately, the excitation filter was set to 485 nm and the emission was detected at 530 nm (Fusion Photometer A153601, PerkinElmer). The fluorescence signal correlates to the concentration of intact ds-DNA.

Figure 13:
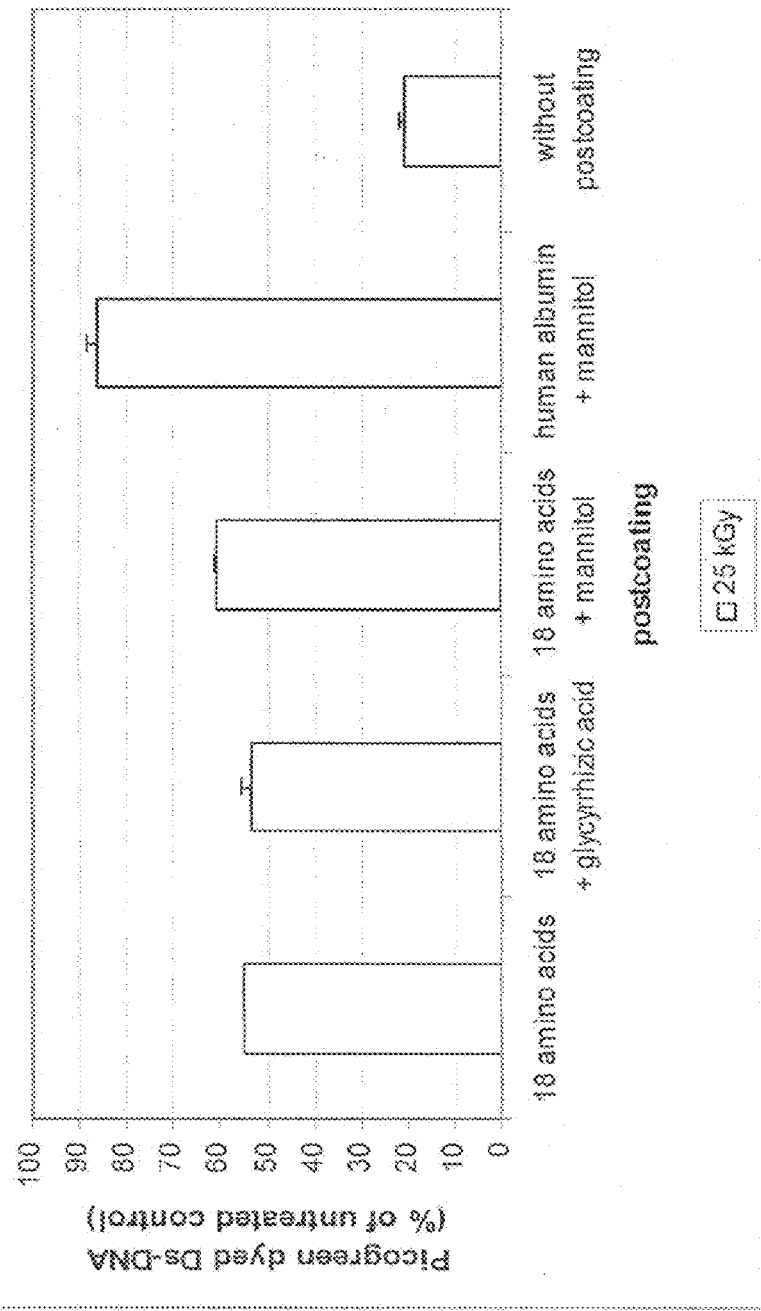

Results:

As depicted in FIG. 13, amino acid postcoatings with provide a protective effect of 55-60%, independent of the addition of glyzyrrhizic acid or mannitol. Without postcoating, the amount of intact ds-DNA is reduced to 20% when irradiated with 25 kGy. Conventional stabilizing substances like albumin and mannitol provide a protection of about 85%.

Example 9: Protective Effect of a Specific Amino Acid Composition 20 mg human anti-Hepatitis A antibody (Beriglobin (human IgG, AK), CSL Behring) and 40 mg of a protective composition were dissolved in water to a total volume of 525 µL per sample and lyophilized. Afterwards, the samples were dissolved in 1 mL water and tested for functionality using an HAV (Hepatitis A virus) IgG ELISA.

Composition:

20 g Arginine 20 g Histidine 20 g Lysine 3 g Glutamic acid 2 g Tryptophane 20 g Glycine 15 g Alanine 0.2 g Tween 80

1 g Glycyrrhizic acid ammonium salt

The pH was adjusted to about 7.2 using NaOH and/or NaCl. Afterwards, the solutions were subjected to sterile filtration.

400 µL of solution (corresponding to 40 mg solid compounds) were mixed with 125 µL Beriglobin (corresponding to 20 mg antibody)

Lyophilisation:

Lyophilisation was carried out as follows:

initial freezing temperature −40° C.;

start of vacuum of 0.1 mBar after 3 h freezing time;

temperature rise of about 1.5° C./h for 23 h;

6 h drying over night at 6° C. and 0.004 mBar.

Sterilisation:

The lyophilized samples were irradiated with 25 kGy and one with 50 kGy Beta-radiation.

Figure 14:
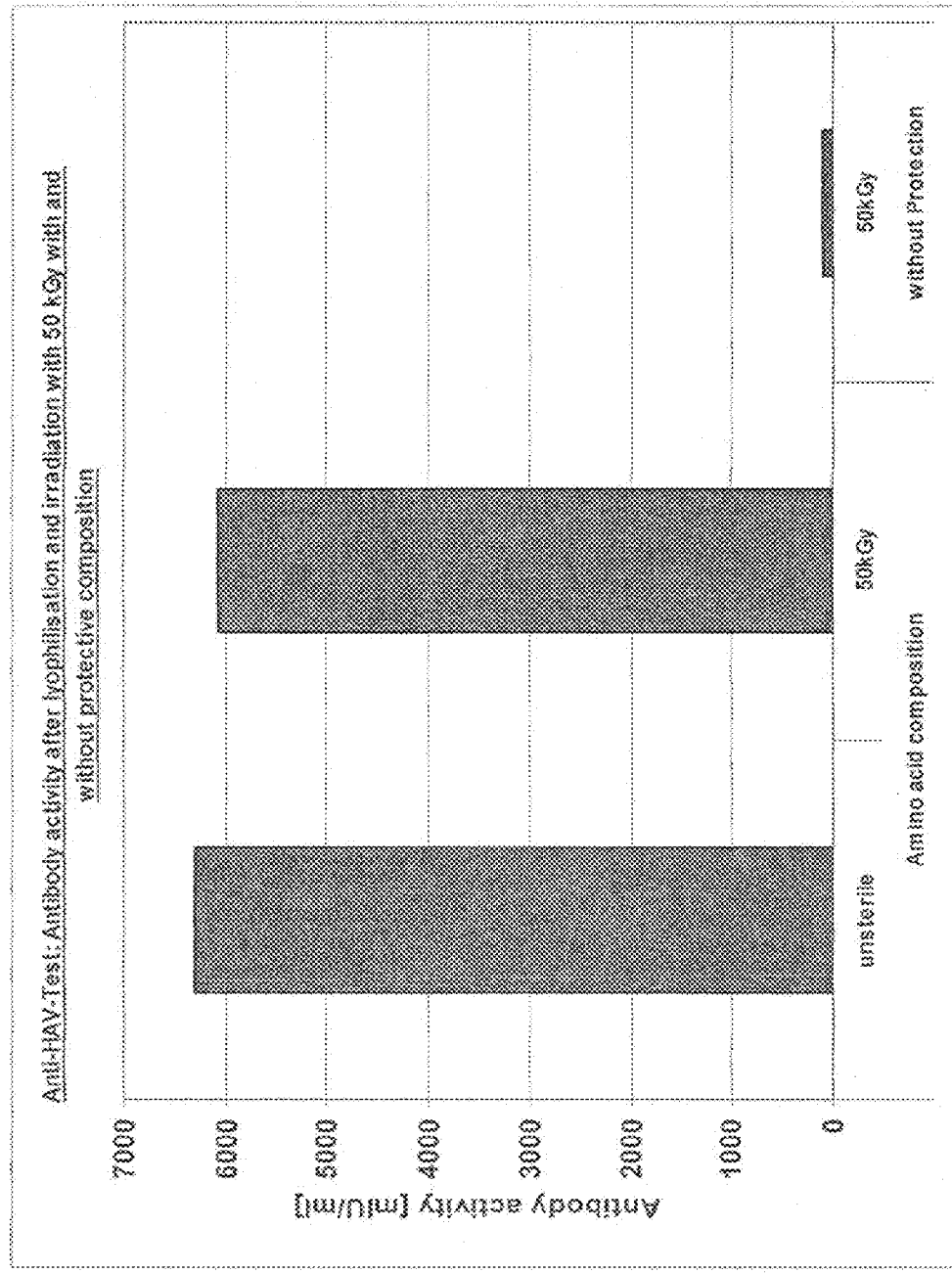

Results:

The results of the HAV-ELISA are depicted in FIG. 14.

After drying and sterilization white, non-odorant, inherently stable cakes were obtained. 1 mL water was added to each sample and the dissolution behaviour was monitored. Dissolution took place within less than 30 seconds and was free of aggregates. Even after 24 h neither macroscopic nor microscopic aggregation was detectable.

Conclusion:

Application of the composition resulted in only little loss of the Hepatitis A antibody portion of Beriglobin as compared to the not irradiated control.

Example 10: Test of Different Saponins as Stabilizing Compounds. The Structural Class of Saponins has a Stabilizing Effect on Antibodies Materials & Methods All experiments were based on the same basic ELISA assay design. (see above)

Adsorption of LO-MM-3 to an ELISA plate and application of postcoatings
Stress exposure of the coated surface
ELISA detection of LO-MM-3 functionality Experiment:

Adsorption of LO-MM-3 to the plate and application of the postcoating and sterilization; as well as the general ELISA procedure were conducted as described in the Materials & Methods section. The irradiation dose (electron beam) was 50 kGy.

Figure 15:
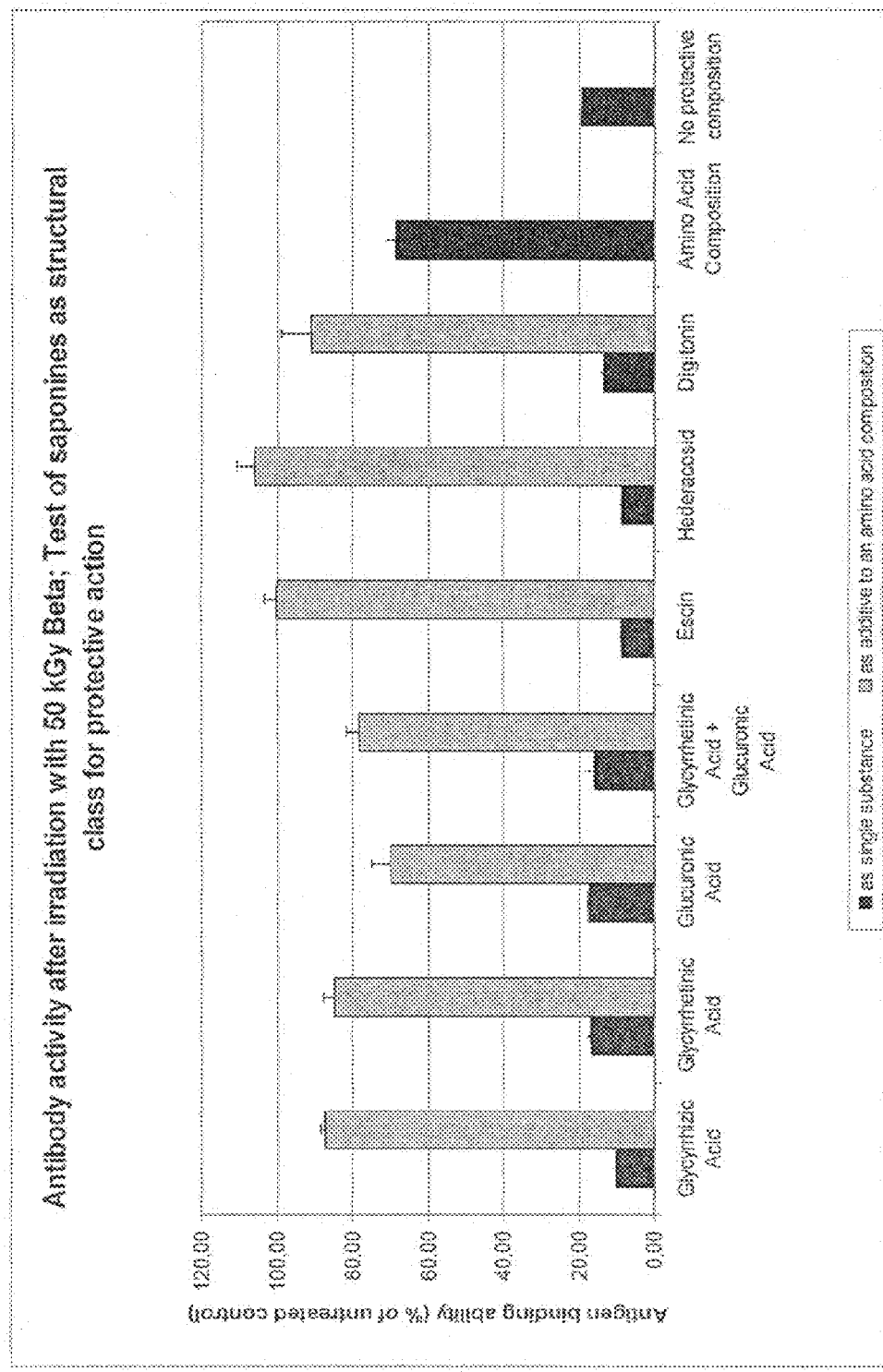

Results:

The results of the experiment are depicted in FIG. 15. The structural class of saponins has the potential to enhance the protective effect of amino acid combinations. Preferred is the use of the saponin glycyrrhizic acid.

Example 11: Stabilizing Compositions Comprising at Least 3 Different Amino Acids or at Least Two Different Amino Acids and a Saponin Such Glycyrrhizic Acid Provide Very Good Protection Materials & Methods All experiments were based on the same basic ELISA assay design. (see above)

Adsorption of LO-MM-3 to an ELISA plate and application of postcoatings
Stress exposure of the coated surface
ELISA detection of LO-MM-3 functionality Experiment:

The amino acids were dissolved either in 0.5 M NaOH (Merck, 106482) or 0.5 M HCl (Merck, 100319) to obtain stock solutions with a maximal concentration. The amino acid stock solutions were mixed together in different combinations to get total amino acid concentrations of 20 g/L in the postcoating solutions.

The pH of the amino acid mixtures was set to approx. 7.0.

Adsorption of LO-MM-3 to the plate and application of the postcoating and sterilization; as well as the general ELISA procedure were conducted as described in the Materials & Methods section. The irradiation dose (electron beam) was 50 kGy.

Figure 16:
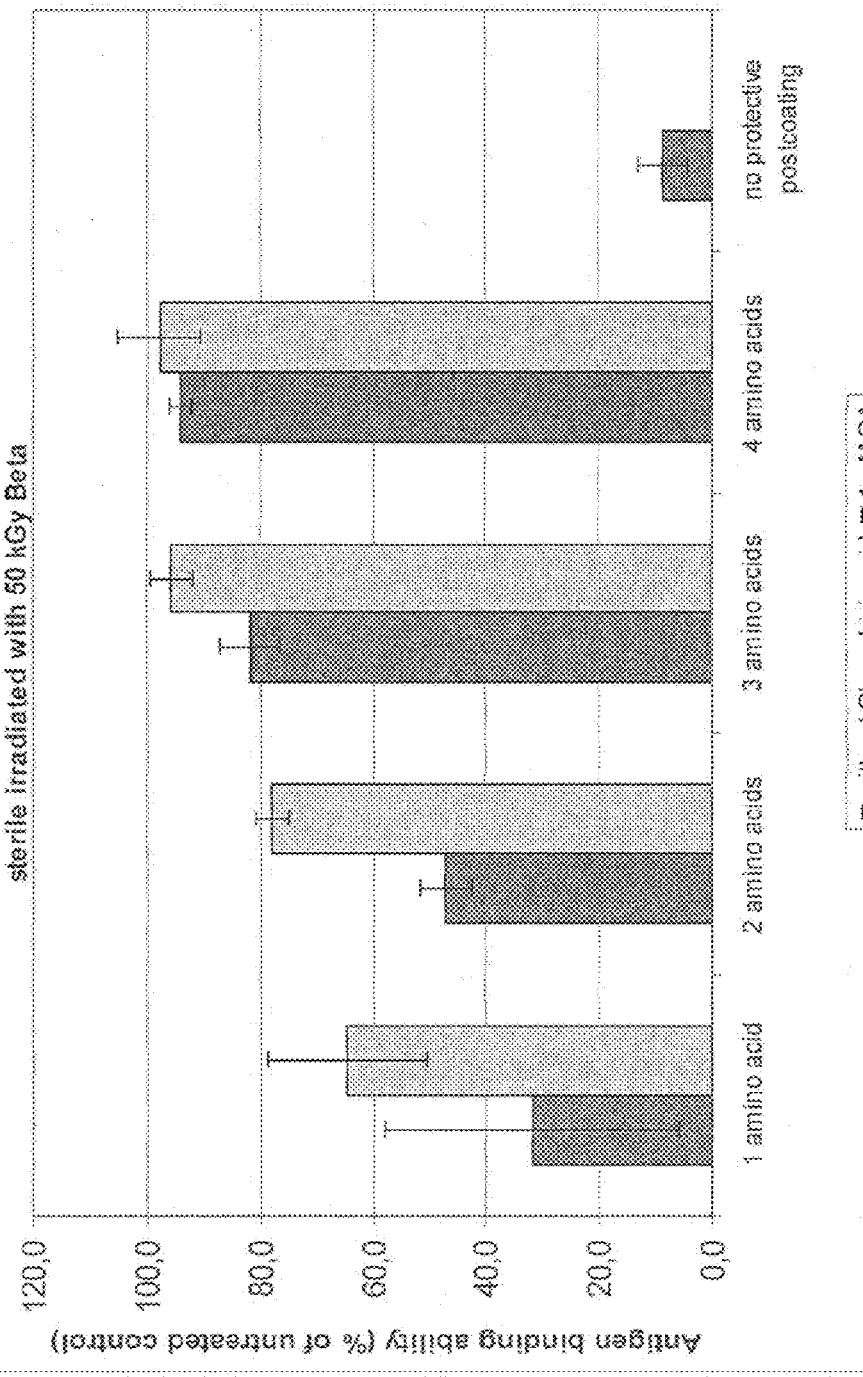

Results:

The results of the experiment are depicted in FIG. 16. Combinations of at least 3 amino acids and combinations of 2 amino acids with the addition of glycyrrhizic acid provide a maximal protection (more than 75%) of an immobilized antibody when sterilized with 50 kGy beta irradiation.

Example 12: A Preferred Amino Acid Composition Provides Protection Under Different Stress Conditions Materials & Methods All experiments were based on the same basic ELISA assay design. (see above)
Adsorption of LO-MM-3 to an ELISA Plate and Application of Postcoatings
Stress Exposure of the Coated Surface
ELISA Detection of LO-MM-3 Functionality Experiment:
Compositions Used:
Protective Composition A (Compound Per Liter)
20 g Arginine
20 g Histidine
20 g Lysine
3 g Glutamine
2 g Tryptophan
20 g Glycine
15 g Alanine
0.2 g Tween 80
1 g Glycyrrhizic acid ammonium salt The pH was adjusted to about 7.2 using NaOH and/or HCl. Afterwards, the solutions were subjected to sterile filtration.

Adsorption of LO-MM-3 to the plate and application of the postcoating and sterilization; as well as the general ELISA procedure were conducted as described in the Materials & Methods section.

Figure 17:
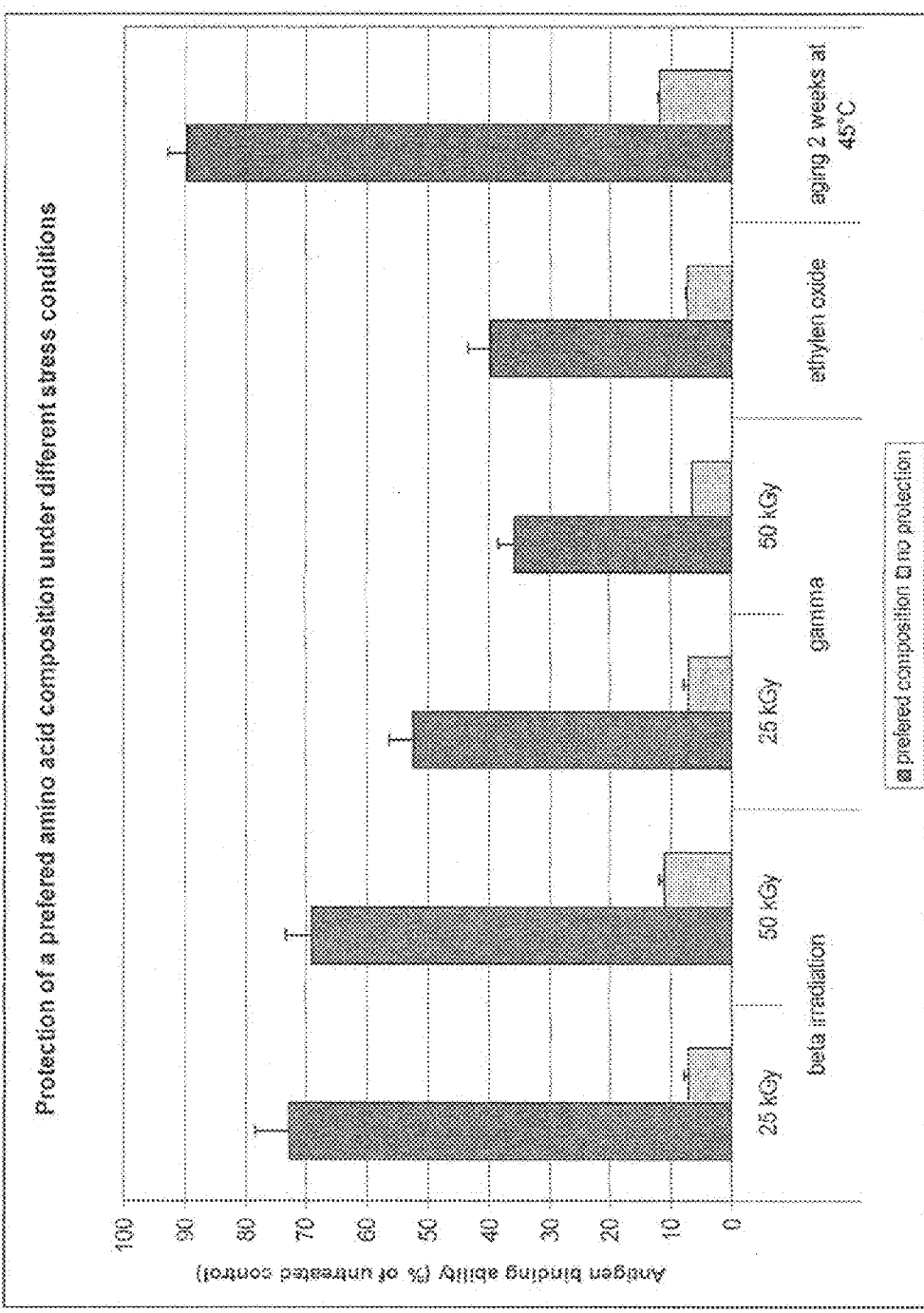
Figure 18:
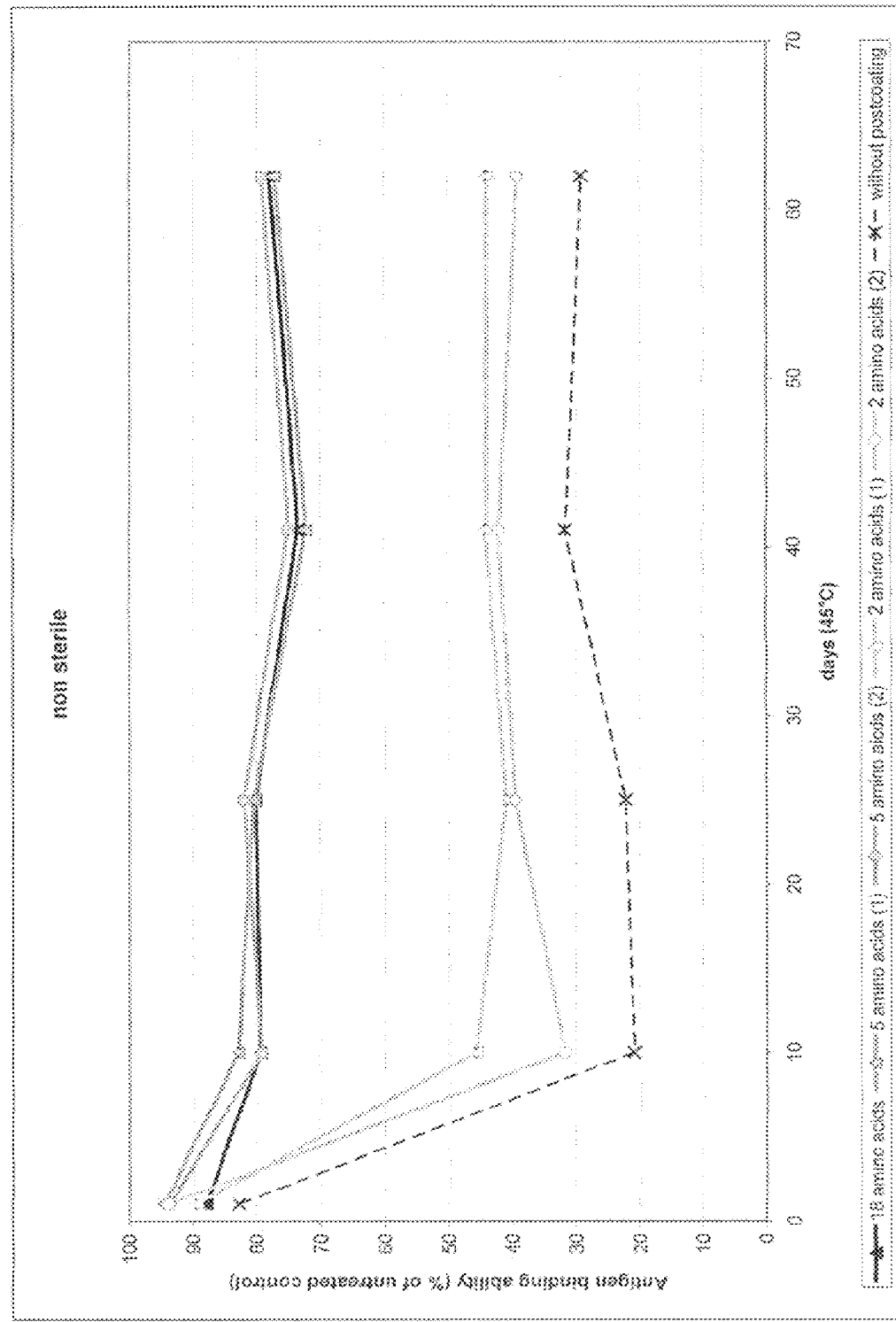
Figure 19:
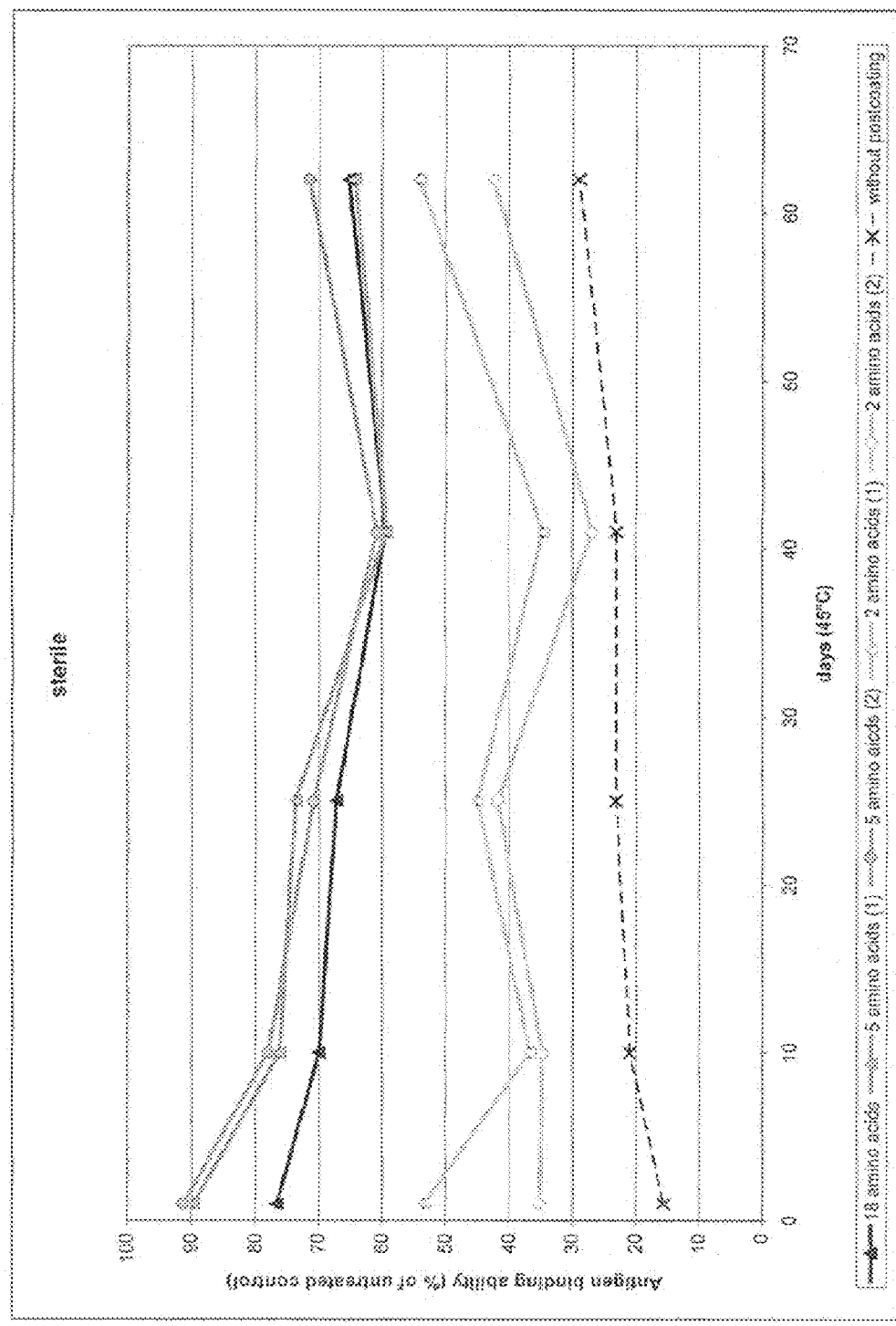
Figure 20:
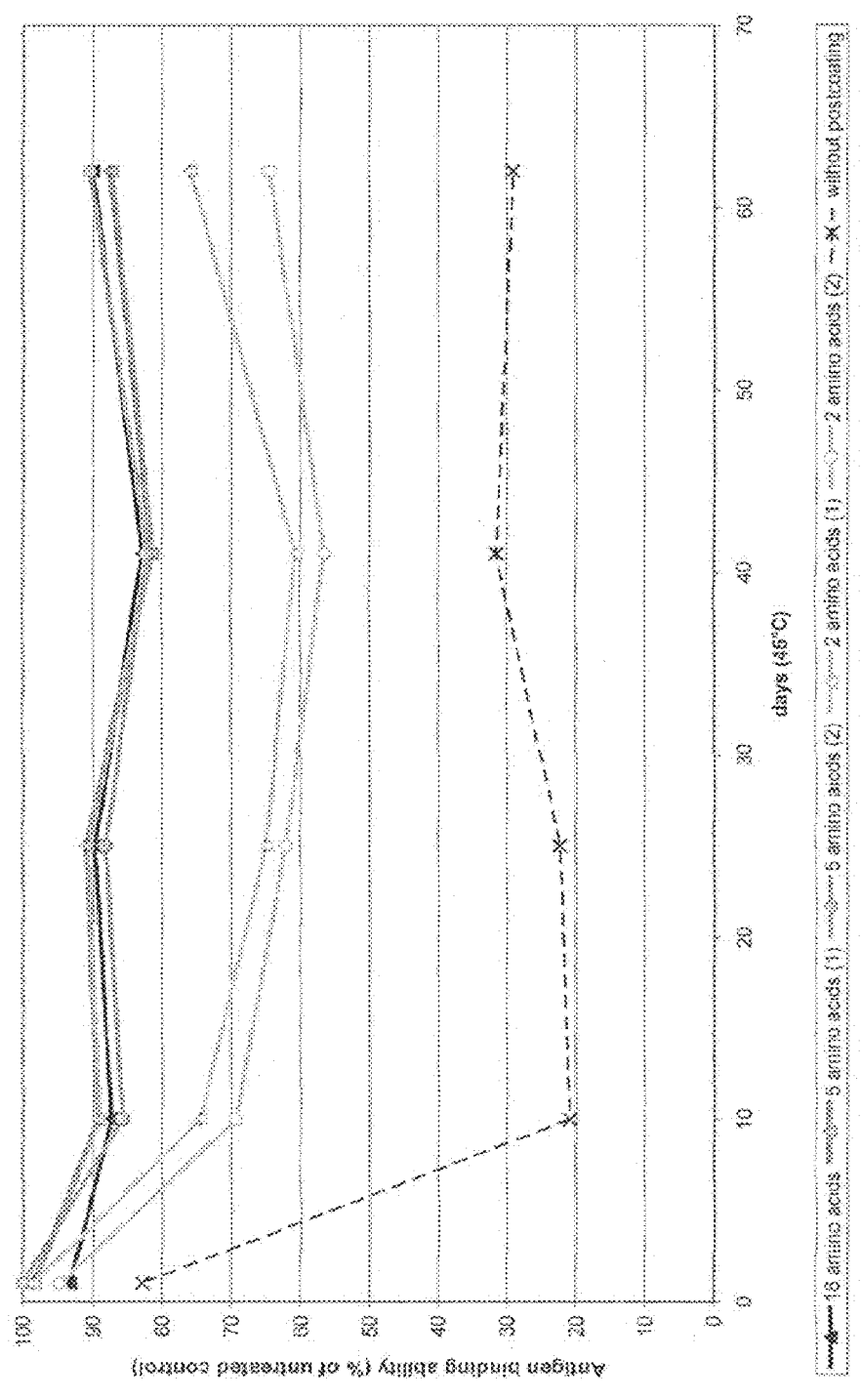
Figure 21:
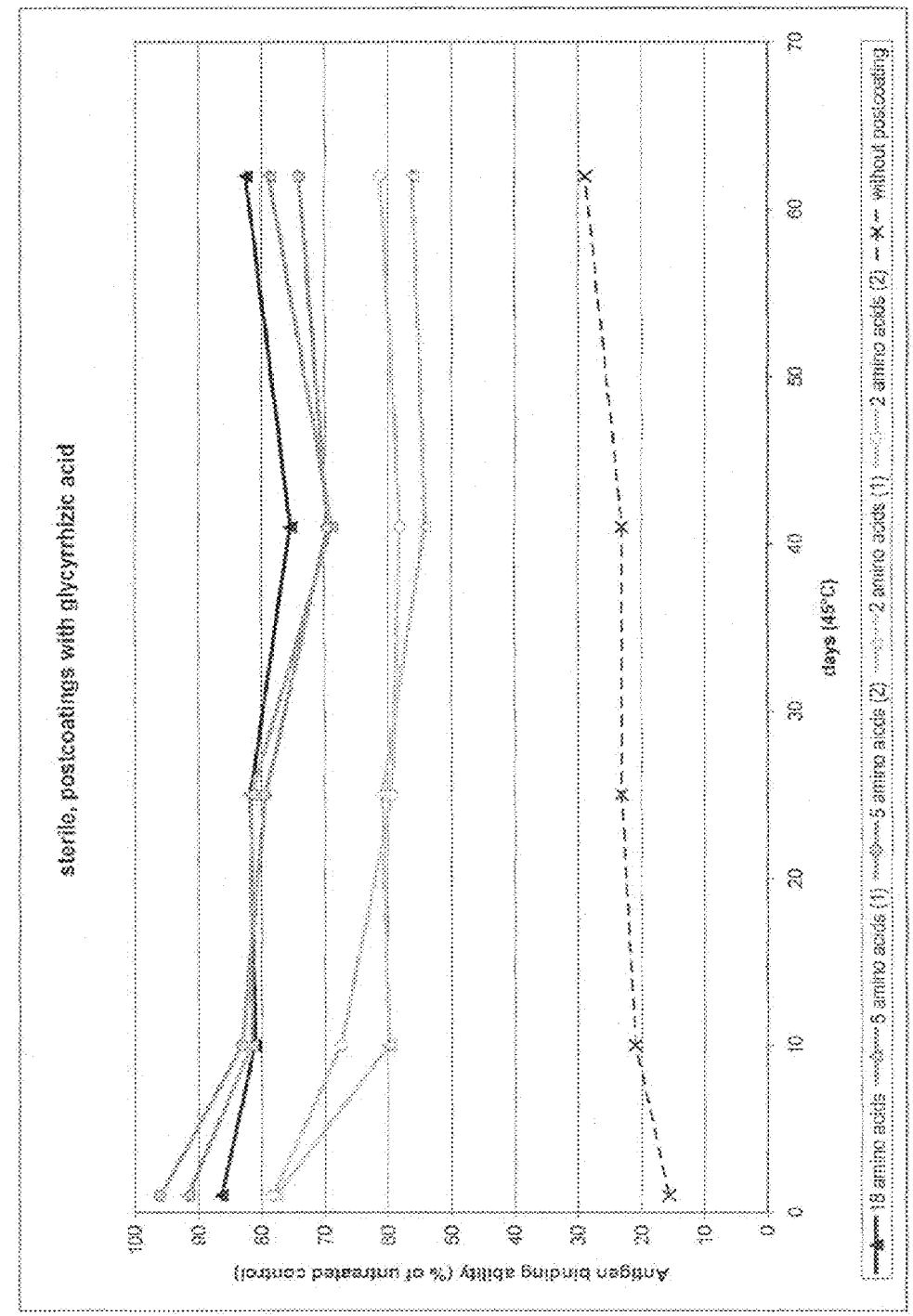
Figure 22:
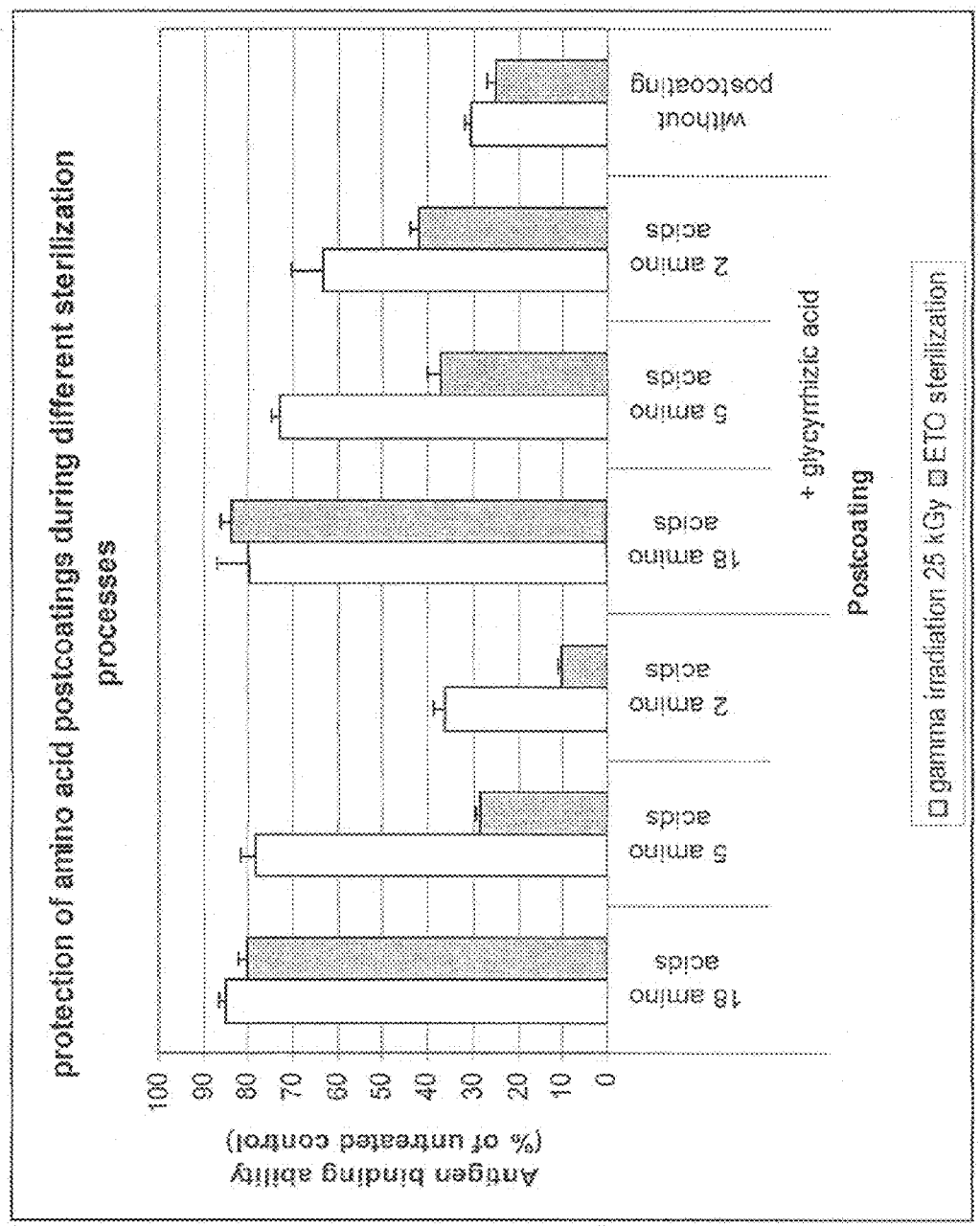
Figure 23:
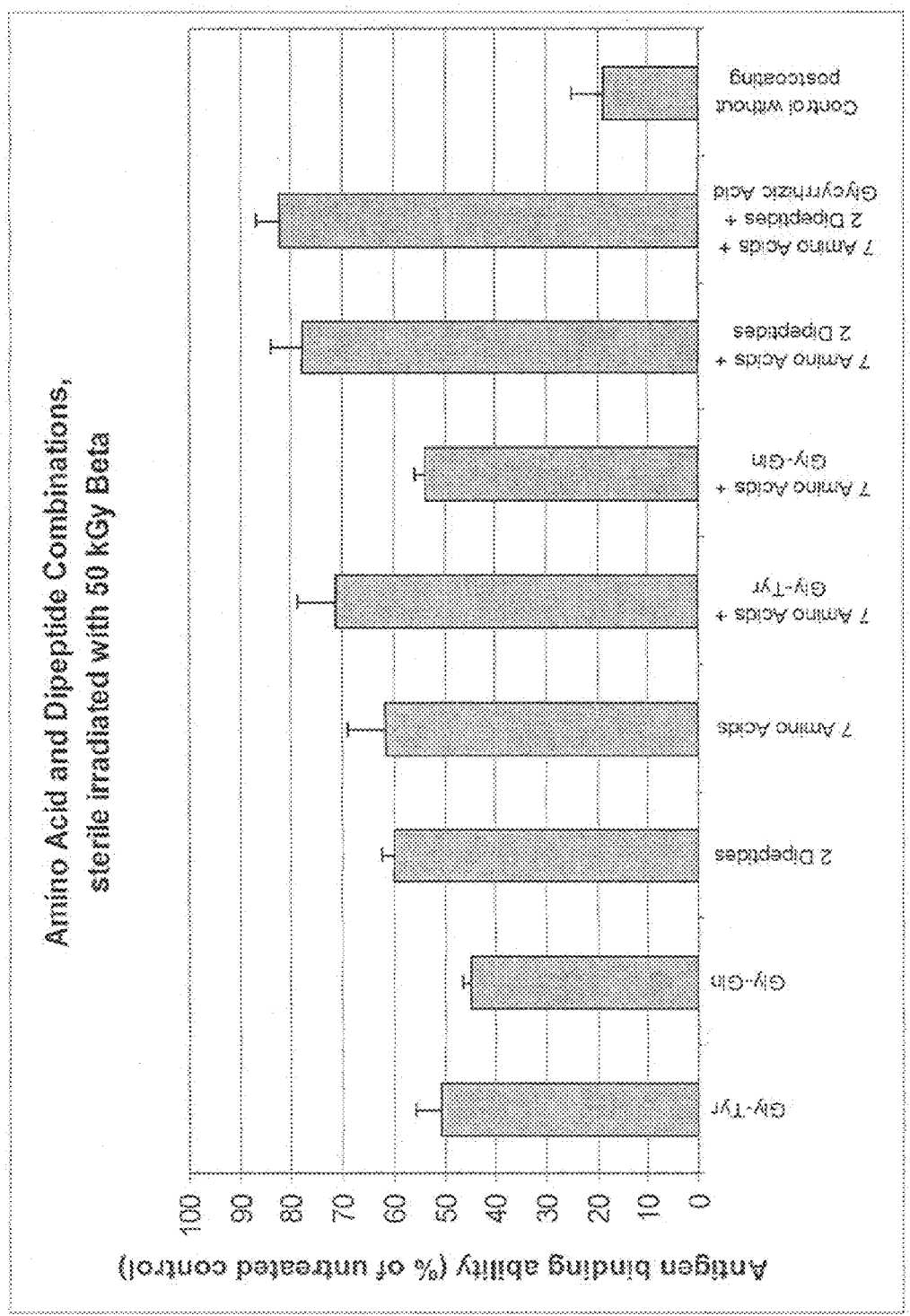
Figure 24:
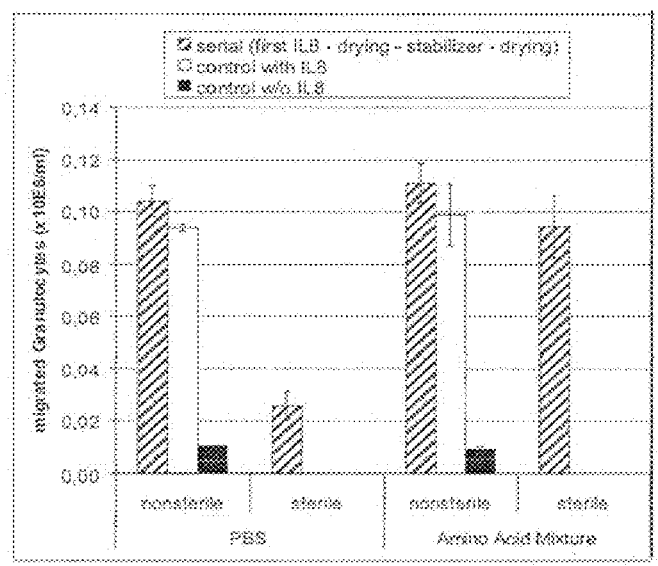
Figure 25:
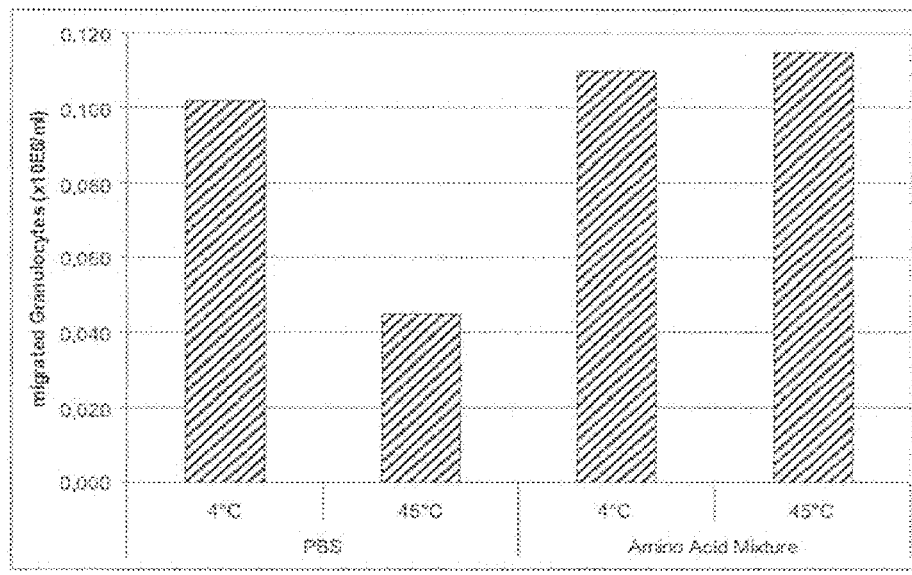

Results:

The results of the experiment are depicted in FIG. 17. The amino acid composition provides protection under different stress conditions. The best protection is provided for beta irradiation with different doses and artificial aging under elevated temperature. The protection for gamma irradiation or ethylene oxide sterilisation is less but still relevant.

Example 13: Amino Acid Postcoatings Provide Protection During Long-Time Storage

Experiment:

The amino acids were dissolved either in 0.5 M NaOH (Merck, 106482) or 0.5 M HCl (Merck, 100319) to obtain stock solutions with a maximal concentration. The amino acid stock solutions were mixed together to get a total amino acid concentration of 200 mM in the postcoating solution. The amino acids were used in equimolar ratio.

18 amino acids: Ala, Arg, Asp, Gln, Glu, Gly, His, Ile, Leu, Lys, Met, Phe, Pro, Ser, Thr, Trp, Tyr, Val
5 amino acids (1): Asp, Arg, Phe, Ser, Val
5 amino acids (2): Ala, Glu, Lys, Thr, Trp
2 amino acids (1): Asp, Val
2 amino acids (2): Ala, Glu The pH of the amino acid mixtures was set to approx. 7.0; and the mixtures were further diluted in PBS to get the final concentration of 200 mM.

Adsorption of LO-MM-3 to the plate and application of the postcoating and sterilization; as well as the general ELISA procedure were conducted as described in the Materials & Methods section. Long-time storage was simulated by an accelerated aging procedure. The plates were stored at 45° C. and antibody activity was determined after 0, 10, 25, 41 and 62 days of storage. This equals real time aging at 5° C. of 0, 6, 12, 24 and 36 months.

Results:

Amino acid postcoatings containing at least 5 amino acids provide protection during long time storage. For the non-sterilized samples, after 62 days at 45° C. about 80% of the antigen binding ability is perservered. Sterilized samples (beta, 25 kGy) maintain about 70% of their antigen binding ability after 62 days at 45° C. Amino acid postcoatings containing only 2 amino acids maintain only about 40% antigen binding ability during the storage process, regardless of sterilization. The addition of 1 mM glycyrrhizic acid to the postcoating solutions enforces the protecting effect: For the non-sterilized samples containing at least 5 amino acids and glycyrrhizic acid, after 62 days at 45° C. about 90% of the antigen binding ability is preserved. Sterilized samples (beta, 25 kGy) maintain about 80% of their antigen binding ability after 62 days at 45° C. Amino acid postcoatings containing 2 amino acids and glycyrrhizic acid maintain about 70% antigen binding ability during the storage process.

Example 14: Amino Acid Postcoatings Provide Protection During Different Sterilization Processes Experiment:
The amino acids were dissolved either in 0.5 M NaOH (Merck, 106482) or 0.5 M HCl (Merck, 100319) to obtain stock solutions with a maximal concentration. The amino acid stock solutions were mixed together to get a total amino acid concentration of 200 mM in the postcoating solution. The amino acids were used in equimolar ratio.
18 amino acids: Ala, Arg, Asp, Gln, Glu, Gly, His, Ile, Leu, Lys, Met, Phe, Pro, Ser, Thr, Trp, Tyr, Val
5 amino acids: Asp, Arg, Phe, Ser, Val
2 amino acids: Asp, Val
The pH of the amino acid mixtures was set to approx. 7.0; and the mixtures were further diluted in PBS to get the final concentration of 200 mM.
Adsorption of LO-MM-3 to the plate and application of the postcoating and sterilization; as well as the general ELISA procedure were conducted as described in the Materials & Methods section. One plate was irradiated (gamma, 25 kGy). The irradiation was conducted at Beta-Gamma-Service, Bruchsal, Germany. Another plate was sterilized by EO (ETO BO1 cycle); the sterilization was conducted at Rose GmbH, Trier, Germany.
Results:
Samples sterilized with gamma irradiation maintain about 85% activity when protected with an amino acid postcoating containing 18 amino acids; this effect is not further enhanced with glycyrrhizic acid; with 5 amino acids the remaining activity is 75%; with 2 amino acids only 40% are maintained. The protection with 2 amino acids is improved by the addition of glyccyrhizic acid; here the remaining activity is 65%. Samples sterilized with ETO maintain about 85% activity when protected with an amino acid postcoating containing 18 amino acids; this effect is not further enhanced with glycyrrhizic acid. Postcoatings containing 5 or 2 amino acids have only little protecting effect; the addition of glycyrrhizic acid enhances the protection marginally.

Example 15: Postcoatings Consisting of Amino Acids and Dipeptides Provide Protection Against High Irradiation Doses Materials & Methods
All experiments were based on the same basic ELISA assay design. (see above)
Adsorption of LO-MM-3 to an ELISA plate and application of postcoatings
Stress exposure of the coated surface
ELISA detection of LO-MM-3 functionality
Experiment:
The amino acids were dissolved either in 0.5 M NaOH (Merck, 106482) or 0.5 M HCl (Merck, 100319) to obtain stock solutions with a maximum concentration. The amino acid stock solutions were mixed together to get a total amino acid concentration of 20 g/L in the postcoating solution. The dipeptides alone were used with a concentration of 10 g/L and in combination with amino acids with 2 g/L.

7 amino acids: Arg, His, Lys, Glu, Trp, Gly, Ala
2 dipeptides: Gly-Tyr, Gly-Gln
The pH of the amino acid mixtures was set to approx. 7.0.
Adsorption of LO-MM-3 to the plate and application of the postcoating and sterilization; as well as the general ELISA procedure were conducted as described in the Materials & Methods section. The irradiation dose (electron beam) was 50 kGy.
Results:
Samples sterilized with 50 kGy beta irradiation maintain about 60% activity when protected with an amino acid postcoating containing only 7 amino acids; this effect is further enhanced with the addition of dipeptides such as Gly-Tyr or dipeptide combinations. Glycyrrhizic Acid does not enhance the protective effect of the amino acid dipeptide combination further.

Figure 26:
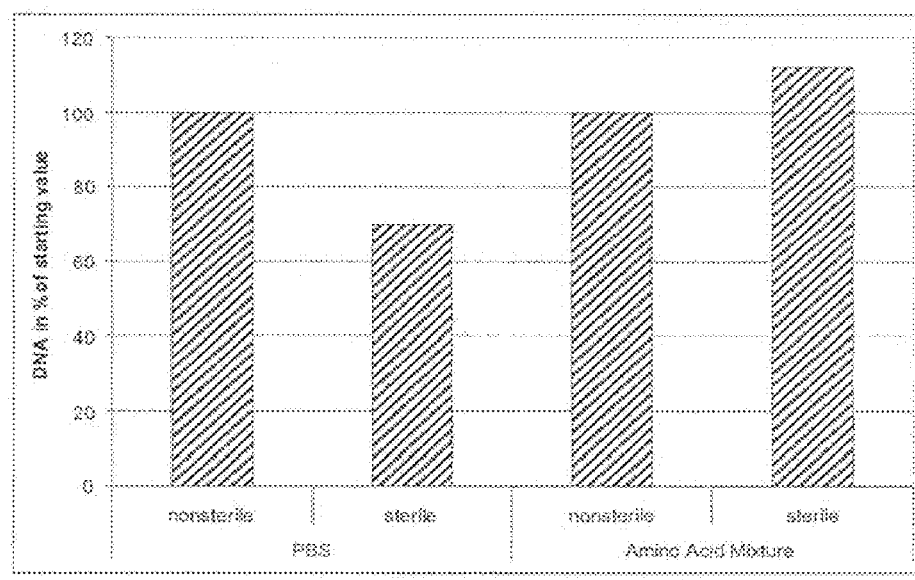
Figure 27:
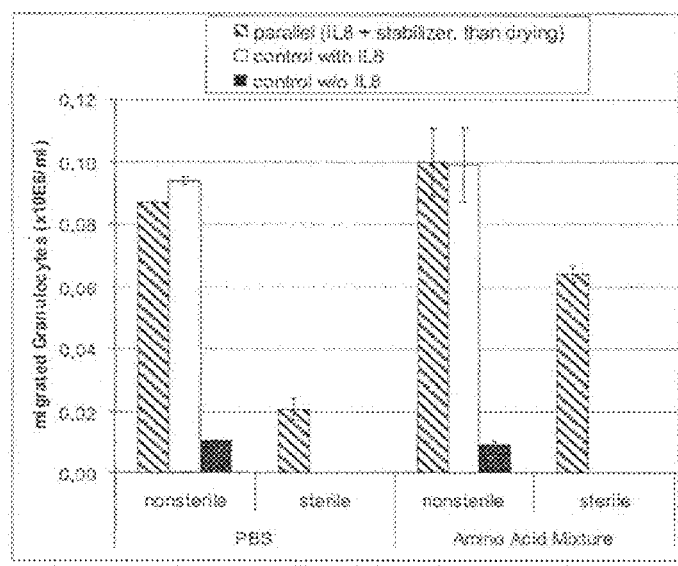
Figure 28:
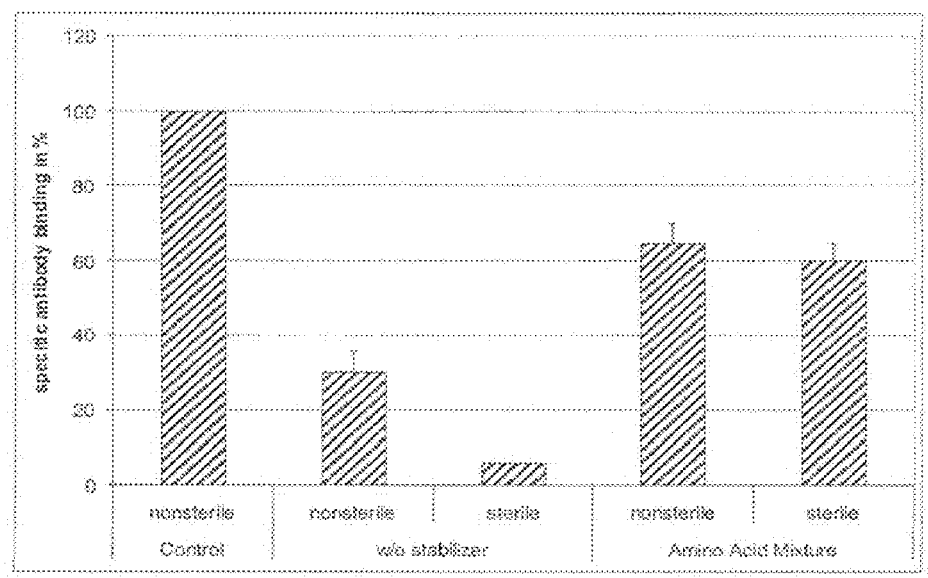

Example 16: Interleukin-8 in Glass-Vials was Sterilized, the Vial Itself is the Carrier Experiment:
Interleukin-8 (IL-8, R&D, 208-IL) was diluted in PBS (without $Ca^{2+}/Mg^{2+}$, PAA, H15-002) to 10 μg/mL. 5 μL of the solution (50 ng IL-8) were added to glass vials and rotated for 4 hours until dried. 25 μL of a stabilizing solution (20 g/L amino acid mixture and 1 mM glyzyrrhizic acid (ammonium salt, Fluke, 50531)) were added and rotated/dried overnight.
The vials were sterilized with 25 kGy (beta irradiation). Unsterilized controls were stored under cool conditions.
Assay:
Neutrophile granulocytes were isolated from 10% ACDA whole blood. 20 mL ACDA blood (10%) were sedimented with 2 mL HES (Grifols 662650). The supernatant was pipetted to 7 mL Percoll (L6143) and centrifuged 20 min at 2000×g. The isolated granulocytes were resuspended in 1% autologous serum and set to a cell count of $0.5 \times 10^6$/mL.
As positive controls 5 μL IL-8-solution (50 ng) were dissolved in 25 μL of the stabilizing solution (A and B). To each sterile vial 1 mL PBS (with $Ca^{2+}/Mg^{2+}$, Hyclone, SH3026401) (with 1% autologous serum) were added to dissolve the dried film.
To detect the chemotactic activity of the samples, the complete IL-8 solutions from the sterile and non-sterile vials and the controls were pipetted into 12-well-plates. Migration filters (3 μm, Corning, 3462) were inserted and 500 μL of the granulocyte suspension was pipetted into the filters. The plates were incubated for 30 min at 37° C. The number of migrated cells was detected by counting the cells in each well via FACS and counting beads (Invitrogen, C36950).
Results:
see FIG. 26
The biomolecule (here interleukin 8=IL8) loses most of its biological function during subsequent sterilisation (25 kGy irradiation) if no stabilizer is added. In contrast, a with different amino acids protected the biomolecule. Shown is the chemotactic activity of IL8 on human neutrophil granulocytes.

Example 17: Interleukin-8 in Glass-Vials was Sterilized, the Stabilizer Itself is the Carrier Experiment:
Interleukin-8 (IL-8) was diluted in PBS (without $Ca^{2+}/Mg^{2+}$, PAA, H15-002) to 10 μg/mL. 5 μL of the solution (50 ng IL-8) and 25 μL of a stabilizing solution (20 g/L amino acid mixture and 1 mM glyzyrrhizic acid (ammonium salt, Fluke, 50531)) were mixed and pipetted into glass vials. The vials were rotated/dried over night.

The vials were sterilized by irradiation with 25 kGy. Unsterilized controls were stored under cool conditions.

Assay:

Neutrophile granulocytes were isolated from 10% ACDA whole blood. 20 mL ACDA blood (10%) were sedimented with 2 mL HES (Grifols 662650). The supernatant was pipetted to 7 mL Percoll (L6143) and centrifuged 20 min at 2000×g. The isolated granulocytes were resuspended in 1% autologous serum and set to a cell count of $0.5 \times 10^6$/mL.

As positive controls 5 µL IL-8-solution (50 ng) were dissolved in 25 µL of a stabilizing solution (A and B). To each sterile vial 1 mL PBS (with $Ca^{2+}/Mg^{2+}$, Hyclone, SH3026401) (with 1% autologous serum) were added to dissolve the dried film.

To detect the chemotactic activity of the samples, the complete IL-8-solutions from the sterile and non-sterile vials and the controls were pipetted into 12-well-plates. Migration filters (3 µm) were inserted and 500 µL of the granulocyte suspension was pipetted into the filters. The plates were incubated 30 min at 37° C. The number of migrated cells was detected by counting the cells in each well (via FACS and counting beads).

Figure 29:
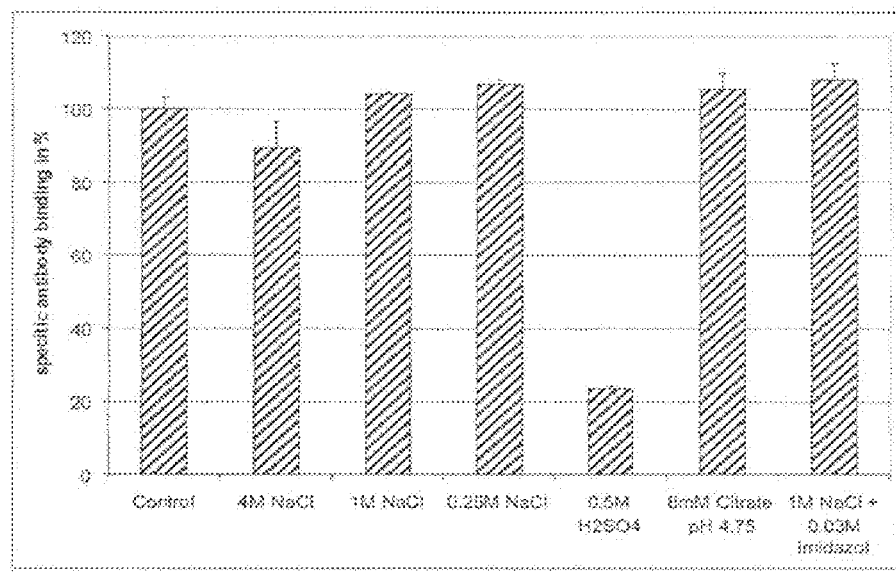

Results:

see FIG. 29

The biomolecule (here interleukin 8=IL8) loses most of its biological function during subsequent sterilisation (25 kGy irradiation) if no stabilizer is added. In contrast, a stabilizer solution with different amino acids protected the biomolecule. Shown is the chemotactic activity of IL8 on human neutrophil granulocytes.

Example 18: Anti-Mouse-IgG in Glass-Vials was Sterilized, the Stabilizer Itself is the Carrier Experiment:

Anti-Mouse-IgG (biotinylated, Jackson ImmunoResearch, 115-065-003) was diluted in PBS (without $Ca^{2+}/Mg^{2+}$, PAA, H15-002) to 4 µg/mL. 25 µL (100 ng) of the antibody solution and 25 µL of a 2× concentrated stabilizing solution (20 g/L amino acid mixture and 1 mM glyzyrrhizic acid (ammonium salt, Fluke, 50531)) were mixed and pipetted into glass vials. The vials were rotated/dried overnight.

The vials were sterilized by irradiation with 25 kGy. Unsterilized controls were stored under cool conditions.

Assay:

An ELISA plate (Greiner Bio-one, 655061) was coated with the antigen (mouse IgG, Innovativ Research, Ir-Ms-Gf): the antigen was diluted to 1 µg/mL, 100 µL were pipetted to each well and incubated over night at 4° C. The plate was washed twice with washing buffer (25× concentrate, Invitrogen, W802). The plate was blocked with Albumin (5%) and washed again 3 times.

To all sample vials 200 µL PBS were added to dissolve the dried film (theoretically 5 µg/mL). The samples were diluted to 10 ng/mL with PBS. To calculate the antibody concentration a serial dilution of fresh antibody was prepared.

The samples and standard were pipetted to the ELISA plate (2×200 µL each) an incubated 1 h at ambient temperature. The plate was washed 3×. To each well 200 µL Streptavidin solution (Horseradish peroxidase (HRP) labeled, Pierce, 21126, diluted to 0.1 µg/mL in PBS) were added and incubated 1 h at ambient temperature. The plate was washed 3×. HRP chromogenic substrate TMB (TMB=tetramethylbenzidine, Invitrogen, 00-2023) was diluted 1:2 in H2O and 200 µL were added to each well. The plate was incubated 15 min at ambient temperature and was protected from light. To stop the color reaction 50 µL diluted H2SO4 (diluted 1:5 with aqua dest., Merck, 1007311000) were added. The absorption of the plate was detected at 450 nm (Fusion Photometer A153601, PerkinElmer).

Figure 30:
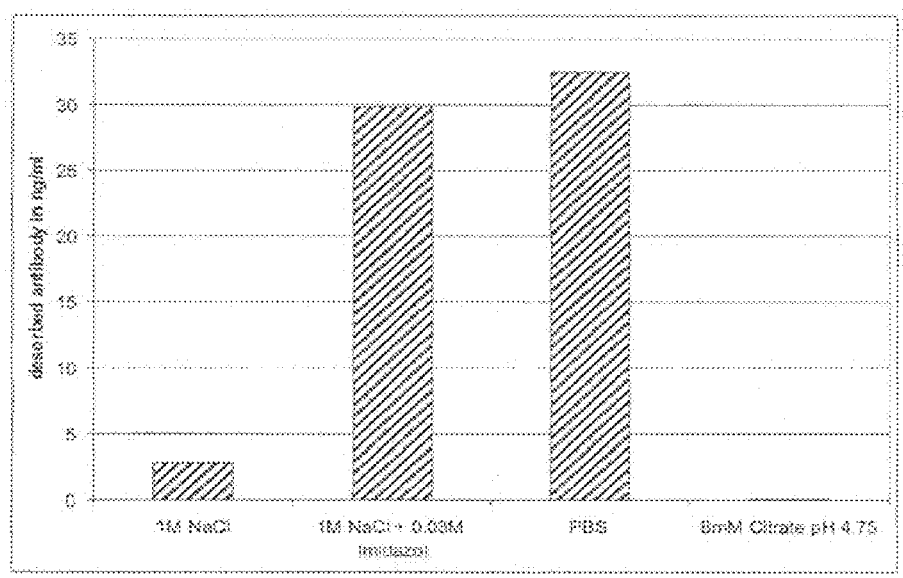
Figure 31:
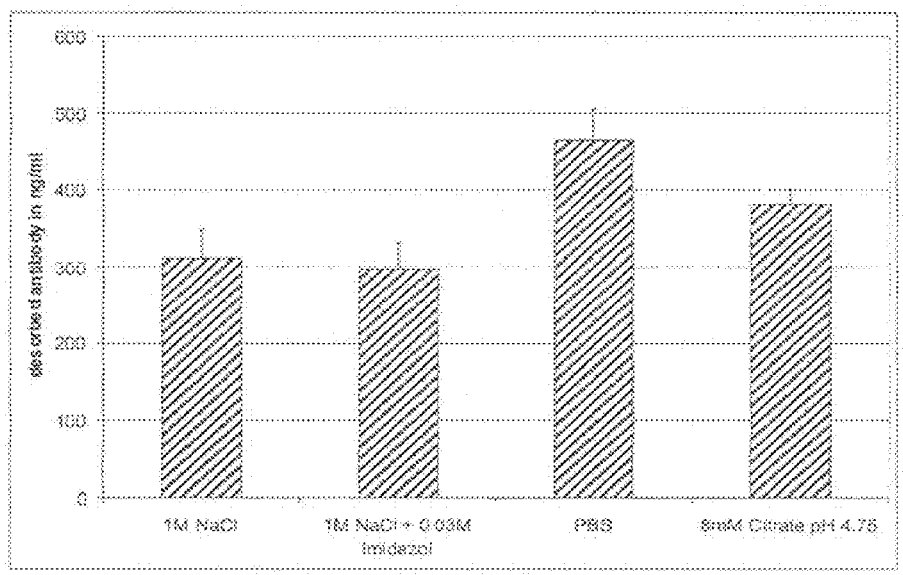
Figure 32:
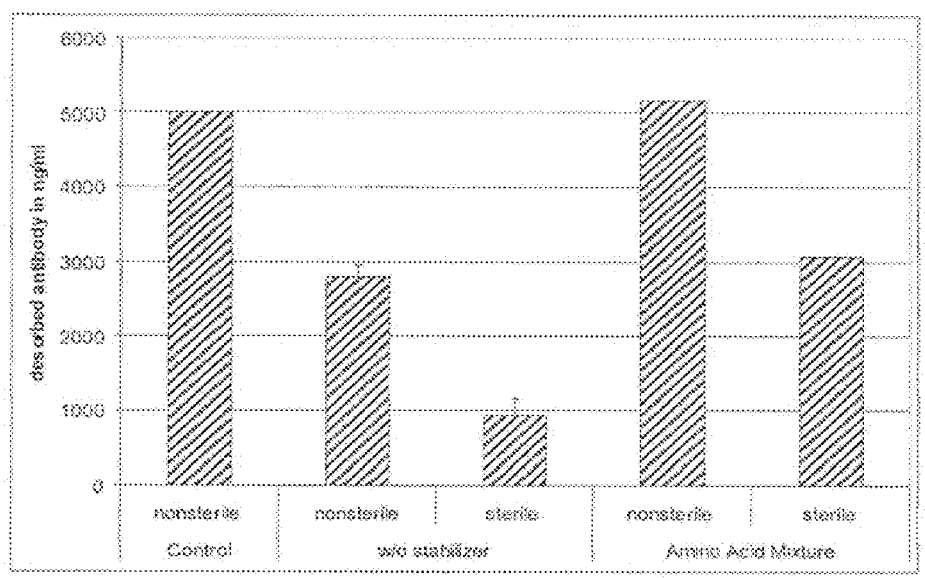
Figure 33:
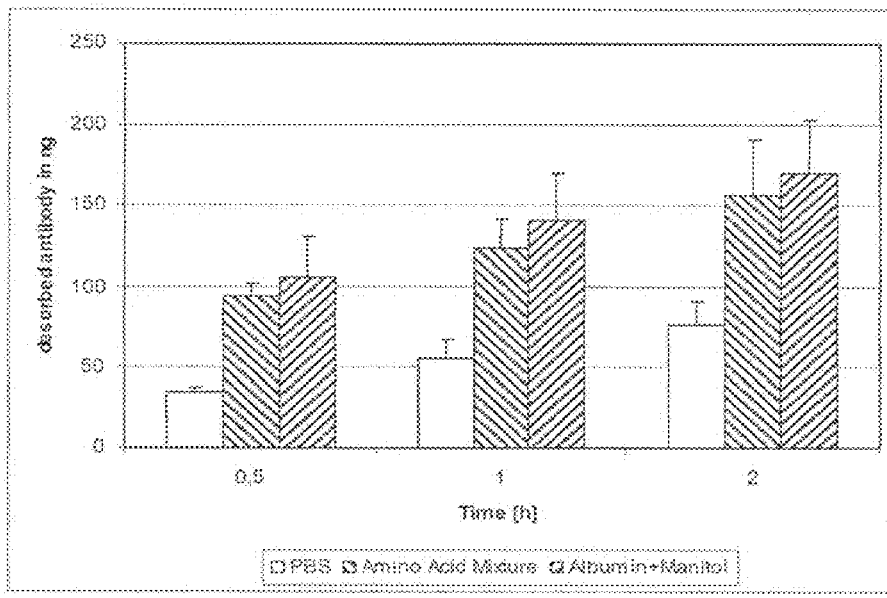

Results:

see FIG. 30

The biomolecule (here an anti-mouse IgG antibody) loses most of its biological function during subsequent storage and or sterilisation (25 kGy irradiation) if no stabilizer is added. In contrast, a stabilizer solution with different amino acids protected the biomolecule. Shown is the specific binding to the antigen.

Example 19: Anti-Mouse-IgG was Sterilized, the Carrier is an Polyurethane Foam

Experiment:

From a fine porous polyurethan (PU) foam (Smith&Nephew, 66012608) samples with a defined diameter (1 cm) were punched. Anti-Mouse-IgG (biotinylated, Jackson ImmunoResearch, 115-065-003) was attached to the samples: the antibody was diluted to 5 µg/mL either in PBS (without $Ca^{2+}/Mg^{2+}$, PAA, H15-002) or in a stabilizing solution (20 g/L amino acid mixture and 1 mM glyzyrrhizic acid (ammonium salt, Fluke, 50531)) and the PU samples were covered with antibody solutions. The samples were incubated 1 h at 37° C.

The antibody solution was removed and the PU samples were air dried for 2 h. The samples were sterilized via beta irradiation (25 kGy) and unsterile controls were stored under cool conditions.

Assay:

An ELISA plate (Greiner Bio-one, 655061) was coated with the antigen (mouse IgG, Innovativ Research, Ir-Ms-Gf): the antigen was diluted to 1 µg/mL, 100 µL were pipetted to each well and incubated over night at 4° C. The plate was washed 2× with washing buffer (25× concentrate, Invitrogen, W802). The plate was blocked with Albumin (5%) and washed again 3×.

The PU samples were covered with PBS and incubated 1 h at ambient temperature. The sample solutions were collected and diluted 1:20 and further serial diluted 1:4 with PBS. To calculate the antibody concentration of the samples a serial dilution of fresh antibody was prepared.

The samples and standard were pipetted to the ELISA plate (2×200 µL each) an incubated 1 h at ambient temperature. The plate was washed 3×. To each well 200 µL Streptavidin solution (Horseradish peroxidase (HRP) labeled, Pierce, 21126, diluted to 0.1 µg/mL in PBS) were added and incubated 1 h at ambient temperature. The plate was washed 3×. HRP cromogenic substrate TMB (TMB=tetramethylbenzidine, Invitrogen, 00-2023) was diluted 1:2 in H2O and 200 µL were added to each well. The plate was incubated 15 min at ambient temperature and was protected from light. To stop the color reaction 50 µL diluted H2SO4 (diluted 1:5 with aqua dest., Merck, 1007311000) were added. The absorption of the plate was detected at 450 nm (Fusion Photometer A153601, PerkinElmer).

Results:

The biomolecule (here an anti-mouse IgG antibody) loses most of its biological function during subsequent storage and or sterilisation (25 kGy irradiation) if no stabilizer is added. In contrast a stabilizer solution protected the biomolecule. The recovery of the antibody is almost 100% (5 μg/mL). Shown is the specific binding to the antigen.

Example 20: Anti-Mouse-IgG was Sterilized, the Carrier is an PVA Hydrogel

Experiment:

A 7% (m/v) solution of polyvinylalcohol (PVA, Sigma, 341584-25G) in water (heated to 85° C.) was prepared. The solution was cooled down to ambient temperature. Anti mouse IgG (biotinylated, Jackson ImmunoResearch, 115-065-003) was diluted to 200 μg/mL in PBS.

The hydrogel mixture was composed as follows:
6.75 mL PVA solution (7%)
4.5 μL anti mouse IgG (200 μg/mL)
2.25 either PBS or stabilizing solution ((20 g/L amino acid mixture and 1 mM glyzyrrhizic acid (ammonium salt, Fluke, 50531)) in PBS)

PVA hydrogels were poured into small petri dishes (diameter 35 mm, 2 mL solution). The hydrogel films were air dried for 48 h. The samples were sterilized via beta irradiation (25 kGy) and unsterile controls were stored under cool conditions.

Assay:

An ELISA plate (Greiner Bio-one, 655061) was coated with the antigen (mouse IgG, Innovativ Research, Ir-Ms-Gf): the antigen was diluted to 1 μg/mL, 100 μL were pipetted to each well and incubated over night at 4° C. The plate was washed 2× with washing buffer (25× concentrate, Invitrogen, W802). The plate was blocked with Albumin (5%) and washed again 3×.

The PVA hydrogels were placed in 6 well plates and covered with 2 mL PBS (without $Ca^{2+}/Mg^{2+}$, PAA, H15-002). After 30 min, 1 h and 2 h the PBS was collected and replaced with fresh PBS.

Serial dilutions of the samples and the standard were pipetted into the ELISA plate (2×200 μL each) and incubated for 1 h at ambient temperature. The plate was washed 3×. To each well 200 μL Streptavidin solution (Horseradish peroxidase (HRP) labeled, Pierce, 21126, diluted to 0.1 μg/mL in PBS) were added and incubated 1 h at ambient temperature. The plate was washed 3×. Chromogenic substrate TMB (TMB=tetramethylbenzidine, Invitrogen, 00-2023) was diluted 1:2 in H2O and 200 μL were added to each well. The plate was incubated 15 min at ambient temperature and was protected from light. To stop the color reaction 50 μL diluted H2SO4 (diluted 1:5 with aqua dest., Merck, 1007311000) were added. The absorption of the plate was detected at 450 nm (Fusion Photometer A153601, PerkinElmer).

Results:

The biomolecule (here an anti-mouse IgG antibody) loses most of its biological function during subsequent storage and or sterilisation (25 kGy irradiation) if no stabilizer is added. In contrast a stabilizer solution protected the biomolecule. The recovery of the eluted antibody is very high. Shown is the specific binding to the antigen.

The invention claimed is:

1. A method for producing stabilized biomolecules, comprising
    (a) reversibly attaching the biomolecules to a solid carrier; and
    (b) embedding the biomolecules in a composition selected from:
        (i) a composition comprising at least three different amino acids, or
        (ii) a composition comprising at least two different amino acids and a saponin,
    wherein the composition of (i) does not contain dipeptides or tripeptides.

2. The method of claim 1, wherein stabilizing biomolecules includes stabilizing the structure and/or activity of biomolecules, enhancing the shelf-life of biomolecules and/or protecting biomolecules against stress-mediated damage.

3. The method of claim 1, wherein the composition comprising at least 3 different amino acids comprises at least 4 or at least 5 different amino acids.

4. The method of claim 3, wherein the composition comprising at least 5 different amino acids comprises at least one amino acid of each group of,
    (a) an amino acid with non polar, aliphatic R groups;
    (b) an amino acid with polar, uncharged R groups;
    (c) an amino acid with positively charged R groups;
    (d) an amino acid with negatively charged R groups; and
    (e) an amino acid with aromatic R groups.

5. The method of claim 3, wherein the composition comprising at least 5 different amino acids comprises amino acids selected from
    (a) alanine, glutamate, lysine, threonine and tryptophan;
    (b) aspartate, arginine, phenylalanine, serine and valine;
    (c) proline, serine, asparagine, aspartate, threonine, and phenylalanine;
    (d) tyrosine, isoleucine, leucine, threonine, and valine; or
    (e) arginine, glycine, histidine, alanine, glutamate, lysine, and tryptophan.

6. The method of claim 1, wherein the composition comprising at least three different amino acids, or the composition comprising at least two different amino acids and a saponin, comprises less than 1% by dry weight cysteine.

7. The method of claim 1, wherein the composition comprising at least three different amino acids, or the composition comprising at least two different amino acids and a saponin, further comprises less than 1% Tween.

8. The method of claim 1, wherein the saponin is glycyrrhizic acid or a derivative thereof.

9. A method of producing a solid carrier having biomolecules attached thereto, comprising the steps of
    (a) reversibly attaching the biomolecules to the solid carrier; and
    (b) incubating the carrier of step (a) in a composition selected from:
        (i) a composition comprising at least three different amino acids, or
        (ii) a composition comprising at least two different amino acids and a saponin,
    wherein the composition of (i) does not contain dipeptides or tripeptides.

10. The method according to claim 1 or 9, further comprising sterilizing the solid carrier after step (b).

11. The method according to claim 10 wherein the sterilization of the carrier is effected by ethylene oxide, beta radiation, gamma radiation, X-ray, heat inactivation, autoclaving or plasma sterilization.

12. The method of claim 1, wherein the biomolecules are reversibly attached to the solid carrier via a cleavable linker, and wherein the biomolecule can be released from the solid carrier by using a means for cleaving the linker.

13. The method of claim 12, wherein the cleavable linker is selected from the group consisting of ethylene glycol bis(succinimidylsuccinate), bis[2-(succinimidooxycarbonyloxy)ethyl]sulfone, dithiobis(succinimidylpropionate), disuccinimidyl tartarate, succinimidyl 2-([4,4'-azipentanamido]ethyl)-1,3'-dithiproprionate, and sulfosuccinimidyl-2-(m-azido-o-nitrobenzamido)-ethyl-1,3'-proprionate.

14. The method according to claim 1 or 9 further comprising
   (c) subjecting the solid carrier to drying.

15. A solid carrier produced by the method of claim 9.

16. The solid carrier of claim 15, wherein the biomolecules are proteins, peptides, nucleic acids, carbohydrates, lipids, fatty acids, polyalcohols and combinations or modifications thereof, wherein the proteins preferably are antibodies, enzymes, receptors, cytokines, hormones, membrane proteins, growth factors, albumins, globulins, transport proteins or blood coagulation factors.

17. The solid carrier of claim 15, wherein the biomolecules specifically bind to a marker protein indicative for a disease, a non-cellular pathogen, a cell or a toxin.

18. A method of preparing a medical device comprising the solid carrier of claim 15, wherein the medical device is selected from the group consisting of an implant, a tubing, a catheter, a stent, a tubing, a wound dressing and a medical device used in extracorporeal circulation.

19. A method for diagnosing a disease comprising the steps of:
   (a) contacting a sample obtained from a patient with a solid carrier according to claim 16 under suitable conditions to allow specific binding of the biomolecules attached to the carrier to said marker protein indicative for a disease, said non-cellular pathogen, said cell or said toxin; and
   (b) detecting whether said marker protein indicative for the disease, said non-cellular pathogen, said cell or said toxin has been bound to the biomolecules.

20. A method for producing stabilized biomolecules, comprising
   (a) adsorbing biomolecules directly to the surface of a solid carrier, and
   (b) covering the biomolecules in a composition selected from:
      (i) a composition comprising at least three different amino acids, or
      (ii) a composition comprising at least two different amino acids and a saponin,
      wherein the composition of (i) does not contain dipeptides or tripeptides,
   so that the biomolecules are partially or completely covered by the composition comprising at least three different amino acids, or the composition comprising at least two different amino acids and a saponin, wherein the covered biomolecules can be released from the carrier by adding a liquid to solubilize/dissolve the covered biomolecules.

21. The method of claim 20, further comprising:
   sterilizing the covered biomolecules; and
   releasing the sterilized covered biomolecules from the carrier.

* * * * *